(12) United States Patent
Attree et al.

(10) Patent No.: US 6,340,594 B1
(45) Date of Patent: Jan. 22, 2002

(54) PRODUCTION OF DESICCATION-TOLERANT GYMNOSPERM EMBRYOS

(75) Inventors: Stephen M. Attree; Lawrence C. Fowke, both of Victoria (CA)

(73) Assignee: CellFor, Inc., Victoria (CA)

(*) Notice: Subject to any disclaimer, the term of this patent is extended or adjusted under 35 U.S.C. 154(b) by 0 days.

(21) Appl. No.: 08/985,788

(22) Filed: Dec. 5, 1997

Related U.S. Application Data

(63) Continuation of application No. 08/244,725, filed as application No. PCT/CA92/00549 on Dec. 18, 1992, now Pat. No. 5,985,667, and a continuation-in-part of application No. 08/159,693, filed on Dec. 1, 1993, now Pat. No. 5,464,769, which is a continuation of application No. 07/810,171, filed on Dec. 19, 1991, now abandoned.

(51) Int. Cl.[7] .............................................. C12N 5/07
(52) U.S. Cl. ....................... 435/422; 435/410; 435/418; 435/430
(58) Field of Search ................................ 435/422, 410, 435/418, 430

(56) References Cited

U.S. PATENT DOCUMENTS

| | | |
|---|---|---|
| 3,920,436 A | 11/1975 | Janssen |
| 4,217,730 A | 8/1980 | Abo El-Nil |
| 4,241,537 A | 12/1980 | Wood |
| 4,245,432 A | 1/1981 | Dannelly |
| 4,249,343 A | 2/1981 | Dannelly |
| 4,251,952 A | 2/1981 | Porter et al. |
| 4,352,883 A | 10/1982 | Lim |
| 4,353,184 A | 10/1982 | Abo El-Nil |
| 4,425,178 A | 1/1984 | Grendon |
| 4,467,560 A | 8/1984 | Simäk |
| 4,534,781 A | 8/1985 | Wu et al. |
| 4,562,663 A | 1/1986 | Redenbaugh |
| 4,615,141 A | 10/1986 | Janick et al. |
| 4,714,697 A | 12/1987 | Krul |
| 4,715,143 A | 12/1987 | Redenbaugh et al. |
| 4,777,762 A | 10/1988 | Redenbaugh et al. |
| 4,957,866 A | 9/1990 | Gupta et al. |
| 5,034,326 A | 7/1991 | Pullman et al. |
| 5,036,007 A | 7/1991 | Gupta et al. |
| 5,041,382 A | 8/1991 | Gupta et al. |
| 5,119,588 A | 6/1992 | Timmis et al. .................. 47/58 |
| 5,183,757 A | 2/1993 | Roberts ................. 435/240.49 |
| 5,187,092 A | 2/1993 | Uddin ................... 435/240.45 |
| 5,236,469 A | 8/1993 | Carlson et al. .............. 47/57.6 |
| 5,236,841 A | 8/1993 | Gupta et al. ........... 435/240.45 |
| 5,238,835 A | 8/1993 | McKersie et al. ..... 435/240.45 |
| 5,284,765 A | 2/1994 | Bryan et al. ............. 435/240.4 |
| 5,294,549 A | 3/1994 | Pullman et al. ........ 435/240.45 |
| 5,427,593 A | 6/1995 | Carlson et al. .............. 47/57.6 |
| 5,451,241 A | 9/1995 | Carlson et al. .............. 47/57.6 |
| 5,482,857 A | 1/1996 | Gupta et al. ........... 435/240.45 |
| 5,486,218 A | 1/1996 | Carlson et al. .............. 47/57.6 |
| 5,563,061 A | 10/1996 | Gupta ................... 435/240.45 |
| 5,564,224 A | 10/1996 | Carlson et al. .............. 47/57.6 |

FOREIGN PATENT DOCUMENTS

| | | |
|---|---|---|
| CA | 2013821 A1 | 4/1990 |
| CA | 2017417 A1 | 5/1990 |
| CA | 2020572 A1 | 7/1990 |
| CA | 2075135 A1 | 7/1992 |
| EP | 293 598 A2 | 12/1988 |
| EP | 300 730 A1 | 1/1989 |
| WO | WO 87/02701 | 5/1987 |
| WO | WO 89/05575 | 6/1989 |
| WO | WO 90/00002 | 1/1990 |
| WO | WO 90/01058 | 2/1990 |
| WO | WO 91/00781 | 1/1991 |
| WO | WO 91/01629 | 2/1991 |
| WO | WO 93/19585 | 10/1993 |

OTHER PUBLICATIONS

Somments Submitted on Behalf of the Applicant Regarding the Informal Protest filed on Jun. 11, 1999 by Barrigar Intellectual Property Group.

Further Protest regarding opposition to Canadian Application No. 2,125,410, submitted by Kirby Eades Gale and Barker by Edwin J. Gale, protesters's reference No. 41695, May 10, 1999.

Further Prior Art Statement and Protest regarding opposition to Canadian Application No. 2,125,410, submitted by Kirby Eades Gale and Baker by Edwin J. Gale, protester's reference No. 41695, Jun. 11, 1999.

Informal comments regarding opposition to Canadian Application No. 2,125,410, submitted by Barrigar & Moss, filed May 10, 1999.

Kermode and Bewley, "The Role of Maturation Drying in the Transition from Seed Development to Germination," *Journal of Experimental Botany* 36(173):1916–1927, 1985.

Carman, "Improved somatic embryogenesis in wheat by partial simulation of the in–ovulo oxygen, growth–regulator and desiccation environments," *Plant Cell Reports* 175417–424, 1988.

(List continued on next page.)

*Primary Examiner*—Leon B. Lankford, Jr.
(74) *Attorney, Agent, or Firm*—Michael Best & Friedrich LLC

(57) ABSTRACT

Desiccated mature gymnosperm somatic embryos, preferably coniferous somatic embryos having a moisture content of less than about 55%, are prepared by water stressing immature embryos in a medium comprising a metabolizable carbon source and a suitable growth regulator influencing embryo development, for a period of time and under conditions sufficient to yield mature viable somatic embryos having a moisture content in the specified range. The water stressing should may be environmental, as by controlled declining relative humidity. Or a suitable osmotic or non-osmotic water stress agent can be used. The use of a non-permeating osmotic water stress agent such as polyethylene glycol of molecular weight at least about 1,000 is preferred, in which case the water stress should simulate a non-osmotic water stress. An example of a suitable preferred growth regulator is abscisic acid.

249 Claims, 9 Drawing Sheets

OTHER PUBLICATIONS

Compton et al., "Plant Recovery from Maize Somatic Embryos Subjected to Controlled Relative Humidity Dehydration," *In Vitro Cell. Dev. Biol.* 38P:197–201, 1992.

Kim and Janick, "Synthetic Seed Technology: Improving Desiccation Tolerance of Somatic Embryos of Celery," *Acta Horticulture* 280:23–28, 1990.

Xu and Bewley, "The role of abscisic acid in germination, storage protein synthesis and desciccation tolerance in alfalfa (*Medicago sativa* L.) seeds, as shown by inhibition of its synthesis by fluridone during development," *Journal of Experimental Botany* 46(287):687–694, 1995.

Lawlor, "Absorption of Polyethylene Glycols by Plants and their Effects on Plant Growth," *New Phytol.* 69:501–513, 1970.

Oishi and Bewley, "Premature Drying, Fluridone–Treatment, and Embryo Isolation During Development of Maize Kernels (*Zea mays* L.) Induce Germination, but the Protein Synthetic Responses are Different. Potential Regulation of Germination and Protein Synthesis by Abscisic Acid," *Journal of Experimental Botany* 43(251):759–767, 1992.

Mexal et al., "Oxygen Availability in Polyethylene Glycol Solutions and Its Implications in Plant–Water Relations," *Plat Physiol* 55:20–24, 1975.

Meurs et al., "Role of Abscisic Acid in the Induction of Desiccation Tolerance in Developing Seeds on *Arabidopsis thaliana*," *Plant Physiol.* 98:1484–1493, 1991.

Adams and Rinne, "Moisture Content as a Controlling Factor in Seed Development and Germination," *International Review of Cytology* 68:1–8, 1980.

Tsukahara and Hirosawa, "Simple dehydration treatment promotes plantlet regeneration of rice (*Oryza sativa* L.) callus," *Plant Cell Reports* 11:550–553, 1992.

Senaratna, "Artificial Seeds," *Biotech Adv.* 10:379–392, 1992.

Gray and Purohit, "Somatic Embryogenesis and Development of Synthetic Seed Technology," *Critical Reviews in Plant Sciences* 10(1):33–61, 1991.

Slade et al., "Artificial Seeds: A Method for the Encapsulation of Somatic Embryos," *Journal of Tissue Culture Methods* 12(4):179–183, 1989.

Xu and Bewley, "Sensitivity to Abscisic Acid and Osmoticum Changes During Embryogenesis of Alfa (*Medicago sativa*)," *Journal of Experimental Botany* 42(239):821–826, 1991.

Xu et al., "Morphological stages and storage protein accumulation in developing alfalfa (*Medicago sative* L.) seeds," *Seed Science Research* 1:119–125, 1991.

Liu et al., "Dry type of carrot (*Daucus carota* L.) artificial seeds," *Scientia Horticulturae* 51:1–11, 1992.

Parrott et al., "Optimization of Somatic Embryogenesis and Embryo Germination in Soybean," *In Vitro Cellular & Developmental Biology* 24(8):817–820, 1988.

Janick et al., "Production of Synthetic Seed by Desiccation and Encapsulation," *In Vitro Cell. Dev. Biol.* 25:1167–1172, 1989.

Kim and Janick, "Abscisic acid and proline improve desiccation tolerance and increase fatty acid content of celery somatic embryos," *Plant Cell. Tissue and Organ Culture* 24:83–89, 1991.

Morris et al., "Changes in water relations and endogenous abscisic acid content of wheat and barley grains and embryos during development," *Plant. Cell and Environment* 14:443–446, 1991.

Marsolais et al., "Somatic embryogenesis and artificial seed production in Zonal (*Pelagonium* X *hortorum*) and Regal (*Pelargonium* x *domesticum*) geranium," *Can. J. Bot.* 69:1188–1193, 1991.

Tsuji et al., "Encapsulation of Somatic Embryos of Carrot and Promotive Effects on the Growth of Plantlets in vitro," *JARQ* 27(2):116–121, 1993.

Bapat and Rao, "Plantlet Regeneration from Encapsulated and Non–encapsulated Desiccated Somatic Embryos of a Forest Tree: Sandalwood (*Santalum album* L.)," *J. Plant Biochemistry & Biotechnology* 1:109–113, 1992.

Shigeta, "Germination and Growth of Encapsulated Somatic Embryos of Carrot for Mass Propagation," *Biotechnology Techniques* 9(10):771–776, 1995.

Redenbaugh, "Application of Artificial Seed to Tropical Crops," *Hortscience* 25(3):251–255, 1990.

Wake et al., "Enhanced germination of artificial seeds by marine cyanobacterial extract," *Appl Microbiol Biotechnol* 36:684–688, 1992.

Sakamoto et al., "Development of Encapsulation Technology for Synthetic Seeds," *Acta Horticulture* 319:71–76, 1992.

Poncelet et al., "Production of alginate beads by emulsification/internal gelation. I. Methodology," *Applied Microbiol Biotechnol* 38:39–45, 1992.

Bapat and Rao, "Sandalwood plantlets from 'Synthetic seeds'," *Plant Cell Reports* 7:434–436, 1988.

Denchev et al., "Somatic embryo production in bioreactors," *Journal of Biotechnology* 26: 99–109, 1992.

Wake et al., "Promotion of plantlet formation from somatic embryos of carrot treated with a high molecular weight extract from a marine cyanobacterium," *Plant Cell Reports* 11:62–65, 1992.

Finkelstein and Crouch, "Hormonal and Osmotic Effects on Developmental Potential of Maturing Rapeseed," *Hortscience* 22(5):797–800, 1987.

Stuart et al., "Biorector Production of Alfalfa Somatic Embryos," *HortScience* 22(5): 800–803, 1987.

Redenbaugh et al., "Encapsulation of Somatic Embryos in Synthetic Seed Coats," *Hortscience* 22(5): 803–809, 1987.

Gray, "Quiescence in Monocotyledonous and Dicotyledonous Somatic Embryos Induced by Dehydration," *Hortscience* 22(5): 810–814, 1987.

Kitto and Janick, "Production of Synthetic Seeds by Ecapsulating Asexual Embryos of Carrot," *J. Amer. Soc. Hort. Sci.* 110(2):277–282, 1985.

Taylor et al., "Storage–protein regulation and lipid accumulation in microspore embryos of *Brassica napus* L.," *Planta* 181:18–26, 1990.

Wiberg et al., "The microspore–derived embryo of *Brassica napus* L. as a tool for studying embryo–specific lipid biogenesis and regulation of oil quality," *Theor Appl Genet* 82:515–520, 1991.

Pence, "Abscisic Acid and the Maturation of Cacao Embryos in Vitro," *Plant Physiol.* 98: 1391–1395, 1992.

Krochko et al., "Contrasting Storage Protein Synthesis and Messenger RNA Accumulation during Development of Zygotic and Somatic Embryos of Alfalfa (*Medicago sativa* L.)," *Plant Physiol.* 99:46–53, 1992.

Homma et al., "Improvement in Production and Regeneration of Somatic Embryos from Mature Seed of Melon (*Cucumis melo* L.) on Solid Media," *Japan. J. Breed.* 41:543–551, 1991.

Noriega and Söndahl, "Somatic Embryogenesis in Hybrid Tea Roses," *Bio/Technology* 9: 991–993, 1991.

Frey et al., "Somatic Embryogenesis in Carnation," *Hortscience* 27(1):63–65, 1992.

Cvikrovä et al., "Phenylalanine ammonia–lyase, phenolic acids and ethylene in alfalfa (*Medicago sativa* L.) cell cultures in relation to their embryogenic ability," *Plant Cell Reports* 10:251–255, 1991.

Faure et al., "Polyamine Pattern and Biosynthesis in Zygotic and Somatic Embryo Stages of *Vitis vinifera*," *J. Plant Physiol.* 138:545–549, 1991.

Büter et al., "Effects of L–proline and post–plating temperature on Maize (*Zea mays* L.) anther culture," *Plant Cell Reports* 10:325–328, 1991.

Qureshi et al., "Modulation of somatic embryogenesis in early and late–stage embryos of wheat (*Triticum aestivum* L.) under the influence of (±)–abscisic acid and its analogs," *Plant Cell, Tissue and Organ Culture* 18:55–69, 1989.

Bueno et al., "Plant regeneration through somatic embryogenesis in *Quercus suber*," *Physiologia Plantarum* 85:30–34, 1992.

Creelman and Mullet, "Water deficit modulates gene expression in growing zones of soybean seedlings. Analysis of differentially expressed cDNAs, a newβ–tubulin gene, and expression of genes encoding cell wall proteins," *Plant Molecular Biology* 17:591–608, 1991.

Komamine et al., "Mechanisms of Somatic Embryogenesis in Cell Cultures: Physiology, Biochemistry, and Molecular Biology," *In Vitro Cell. Dev. Biol.* 28P:11–14, 1992.

Kiyosue et al., "Endogenous Levels of Abscisic Acid in Embryogenic Cells, Non–embryogenic Cells and Somatic Embryos of Carrot (*Daucus carota* L.)," *Biochem. Physiol. Pflanzen* 188:343–347, 1992.

Haccius, "Question of Unicellular Origin of Non–Zygotic Embryos in Callus Cultures," *Phytomorphology* 28:74–81, 1978.

Takahata et al, "A Dry Artfificial Seed System for Brassica Crops," *Acta Horticulturae* 319:317–322, 1992.

Belefant and Fong, "Abscisic acid biosynthesis in *Zea mays* embryos: influence of tetcyclacis and regulation by osmotic potential," *Plant Science* 78:19–25, 1991.

Nichol et al., "Effect of organic acid pretreatment on the regeneration and development (conversion) of whole plants form callus cultures of alfalfa, *Medicago sativa* L.," *Plant Science* 79:181–192, 1991.

Kreuger and Holst, "Arabinogalactan proteins are essential in somatic embryogenesis of *Daucus carota* L.," *Planta* 189:243–248, 1993.

Chalupa, "Plant regeneration by somatic embryogenesis from cultured immature embryos of oak (*Quercus robur* L.) and linden (*Tilia cordata* Mill.)," *Plant Cell Reports* 9:398–401, 1990.

Engelmann, "In vitro conservation of tropical plant germplasm—a review," *Euphytica* 57: 227–243, 1991.

Kishor, "Energy and Osmotic Requirement for High Frequency Regeneration of Rice Plants from Long–Term Cultures," *Plant Science* 48:189–194, 1987.

Nakumura et al., "Studies on Somatic Embryogenesis of Coffee by Scanning Electron Microscope," *Jpn. J. Crop Sci.* 61(3):476–486, 1992.

Chern and Sung, "Prevention of injury during imbibition in shrunken–2–corn seeds by osmotic control of water uptake," *Seed Sci. & Technol.* 19:469–476, 1991.

Prado and Berville, "Induction of Somatic Embryo Development By Liquid Culture in Sunflower (*Helianthus Annus* L.),"Plant Science 67:73–82, 1990.

Arnold et al., "Changes in germinability, ABA content and ABA embryonic sensitivity in developing seeds of *Sorghum bicolor* (L.) Moench. Induced by water stress during grain filling," *New Phytol.* 118:339–347, 1991.

Duncan and Widholm, "Proline Is Not the Primary Determinant of Chilling Tolerance Induced by Mannitol or Abscisic Acid in Regenerable Maize Callus Cultures," *Plant Physiol.* 95:1284–1287, 1991.

Weges et al., "Priming relieves dormancy in lettuce seeds independently of changes in osmotic constituents,"*Physiologia Planatarum* 81:527–533, 1991.

Rush, "Comparison of Seed Priming Techniques with Regard to Seedling Emergence and Phythium Damping–Off in Sugar Beet," *Phytopathology* 81:878–882, 1991.

Reinbothe et al., "Differential accumulation of methyl jasmonate–induced mRNAs in response to abscisic acid and desiccation in barley (*Hordeum vulgare*)," *Physiologia Planatarum* 86:49–56, 1992.

Goffner et al., "Effects of Abscisic Acid and Osmotica on Helianthinin Gene Expression in Sunflower Cotyledons In Vitro," *Plant Science* 66:211–219, 1990.

Galau et al., "The controls of late dicot embryogenesis and early germination," *Physiologia Planatarum* 81:280–288, 1991.

Finkelstein et al., "Role of ABA in Maturation of Rapeseed Embryos," *Plant Physiol.* 78: 630–636, 1985.

Hetherington and Quantro, "Tansley Review No. 31. Mechanisms of action of abscisic acid at the cellular level," *New Phytol.* 119:9–32, 1991.

Thomann et al., "Accumulation of Group 3 Late Embryogenesis Abundant Proteins in *Zea mays* Embryos," *Plant Physiol.* 99:607–614, 1992.

Woodstock and Tao, "Prevention of imbibitional injury in low vigor soybean embryonic axes by osmotic control of water uptake," *Physiol. Plant.* 51:133–139, 1981.

Meinke, "Perspectives on Genetic Analysis of Plant Embryogenesis," *The Plant Cell* 3:857–866, 1991.

Ni and Bradford, "Quantitative Models Characterizing Seed Germination Responses to Abscisic Acid and Osmoticum," *Plant Physiol.* 98:1057–1068, 1992.

Zeevaart, "Metabolism and Physiology of Abscisic Acid," *Ann. Rev. Plant Physiol. Plan Mol. Biol.* 39:439–473, 1988.

Finkelstein and Crouch, "Rapeseed Embryo Development in Culture on High Osmoticum Is Similar to That in Seeds," *Plant Physiol.* 81:907–912, 1986.

Brown et al., "Control of Embryogenesis and Organogenesis in Immature Wheat Embryo Callus Using Increased Medium Osmolarity and Abscisic Acid," *J. Plant Physiol.* 133:727–733, 1989.

Walbot, *Dormancy and Developmental Arrest*, Academic Press, Inc., 1978, Chapter 3, "Control Mechanisms for Plant Embryogeny," pp. 113–166.

Arnold et al., "Changes in dormancy level in *Sorghum halepense* seeds induced by water stress during seed development," *Functional Ecology* 6:596–605, 1992.

Kinnersley and Henderson, "Alternative carbohydrates promote differentiation of plant cells," *Plant Cell, Tissue and Organ Culture* 15:3–16, 1988.

Leopold, *Stress Responses in Plants: Adaption and Acclimation Mechanisms*, Wiley–Liss, Inc., 1990, Chapter 3, "Copin With Desiccation," pp. 37–56.

Redenbaugh et al., *Plant Tissue and Cell Culture*, Alan R. Liss, Inc., New York, 1987, "Scale Up: Artificial Seeds," pp. 473–493.

Anandarajah and McKersie, "Enhanced vigor of dry somatic embryos of *Medicago sativa* L. with increased sucrose," *Plant Science* 71:261–266, 1990.

Attree et al., "Regeneration of somatic embryos from protoplasts isolated from an embryogenic suspension culture of white spruce (*Picea glauca*)," *Plant Cell Reports* 6: 480–483, 1987.

Attree et al., "Initiation of embryogenic callus and suspension cultures, and improved embryo regeneration from protoplasts, of white spruce (*Picea glauca*)," *Can. J. Bot.* 67: 1790–1795, 1989.

Attree et al., *Biotechnology in Agriculture and Forestry*, vol. 16 Trees III (ed. by Y.P.S. Bajaj), Springer, Verlag Berlin Heidelberg, 1991, II.11 White Spruce [*Picea glauca* (Moench) Voss] and Black Spruce [*Picea mariana* (Mill) B.S.P.], pp. 423–445.

Attree and Fowke, *Biotechnology in Agriculture and Forestry*, vol. 17 High–Tech and Micropropagation I (ed. by Y.P.S. Bajaj), Springer, Verlag Berlin Heidelberg, 1991, "I.4 Micropropagation Through Somatic Embryogenesis in Conifers," pp. 53–70.

Avjioglu and Knox, "Storage Lipid Accumulation by Zygotic and Somatic Embryos in Culture," *Annals of Botany* 63: 409–420, 1989.

Barratt et al., "An Analysis of Seed Development in *Pisum sativum*," *Journal of Experimental Botany* 40(218): 1009–1014, 1989.

Bewley and Black, *Seeds Physiology of Development and Germination*, Plenum Press, New York, 1985, Chapter 3, "Storage, Imbition, and Germination", pp. 92–95.

Chang et al., "Clonal propagation of Virginia Pine (*Pinus virginiana* Mill.) by organogenesis," *Plant Cell Reports* 10: 131–134, 1991.

Chowdhury, "The Embroygeny Of Conifers: A Review," *Phytomorphology* 12: 313–338, 1962.

Dutta and Appleqvist, "The Effects Of Different Cultural Conditions On The Accumulation Of Depot Lipids Notable Petroselenic Acid During Somatic Embryogenesis In *Daucus Carota* L." *Plant Science* 64: 167–177, 1989.

Feirer et al., "Triglycerides in embryogenic conifer calli: a comparison with zygotic embryos," *Plant Cell Reports* 8: 207–209, 1989.

Flinn et al., "In Vitro control of caulogenesis by growth regulators and media components in embryogenic explants of eastern white pine (*Pinus strobus*)," *Can. J. Bot.* 64: 1948–1956, 1986.

Hakman et al., "The Development Of Somatic Embryos In Tissue Cultures Initiated From Immature Embryos Of *Picea Abies* (Norway Spruce)," *Plant Science* 38: 53–59, 1985.

Hakman and Arnold, "Plantlet Regeneration through Somatic Embryogenesis in *Picea abies* (Norway Spruce)," *J. Plant Physiol.* 121: 149–158, 1985.

Konar, "A Quantitative Survey Of Some Nitrogenous Substances And Fats In The Developing Embryos And Gametophytes Of *Pinus Roxburghii* Sar.," *Phytomorphology* 8: 174–176, 1958.

Laine et al., "Callus formation from cotyledon protoplasts of *Pinus oocarpa* and *Pinus patula*," *Physiologia Planatarum* 72: 374–377, 1988.

Lu et al., "Plantlet Regeneration From Cultured Embryos And Seedling Parts Of Red Spruce (Picea Rubens Sarg.)," *Bot. Gaz.* 152(1): 42–50, 1991.

Misra et al., "Maturation Drying As The "Switch" That Terminates Seed Development And Promotes Germination," in van Vloten–Doting et al. (eds.), *Molecular form and function of the plant genome*, NATO Scientific Affairs Division, Plenum Press, New York, London, 1985, pp. 113–128.

Mo et al., "Morphogenic and genetic stability in longterm embryogenic cultures and somatic embryos of Norway spruce (*Picea abies* [L.] Kars)," *Plant Cell Reports* 8: 375–378, 1989.

Patel et al., "Plantlet Formation In Pitch Pine (*Pinus Rigida* Mill.) By Tissue Culture Methods," *Forest Ecology and Management* 15: 147–160, 1986.

Pomeroy et al., "Fatty acid changes during development of zygotic and micropsore–derived embryos of *Brassica napus*," *Physiologia Plantarum* 81: 447–454, 1991.

Roberts et al., "Interactions between Maturation and High Relative Humidity Treatments and their Effects on Germination of Sitka Spruce Somatic Embryos," *J. Plant Physiol.* 138: 1–6, 1991.

Saranga and Janick, "Celery Somatic Embryo Production and Regeneration: Improved Protocols," *Hortscience* 26(10): 1335, 1991.

Saravitz et al., "In Vitro Propagation of Virginia Pine from Cotyledons," *J. Amer. Soc. Hort. Sci.* 116(2): 362–365, 1991.

Senaratna et al., "Desiccation Tolerance Of Alfalfa (*Medicago Sativa* L.) Somatic Embryoos. Influence Of Abscisic Acid, Stress Pretreatments And Drying Rates," *Plant Science* 65: 253–259, 1989.

Sotak et al., "Relation of the developmental stage of zygotic embryos of yellow–poplar to their somatic embryogenic potential," *Plant Cell Reports* 10: 175–178, 1991.

Tautorus et al., "Comparative studies of protoplast development in jack pine (*Pinus banksiana*)," *Can. J. Bot.* 68: 1774–1779, 1990.

Von Arnold and Eriksson, "In Vitro studies of adventitous shoot formation in *Pinus contorta*," *Can J. Bot.* 59: 870–874, 1981.

Webb et al., "Micropropagation of eastern white pine (*Pinus strobus* L.)," *Can. J. For. Res.* 18: 1570–1580, 1988.

Hohl and Schopfer, "Water Relations of Growing Maize Coleoptiles," *Plant Physiol.* 95:716–722, 1991.

Kim and Janick, "Origin of Somatic Embryos in Celery Tissue Culture," *Hortscience* 24(4):671–673, 1989.

Saranga et al., "Changes in Tolerance to Partial Desiccation and in Metabolite Content of Celery Somatic Embryos Induced by Reduced Osmotic Potential," *J. Amer. Soc. Hort. Sci.* 117(2):342–345, 1992.

Janick et al., "Developmental Changes in Seeds in Loblolly Pine," *J. Amer. Soc. Hort. Sci.* 116(2):297–301, 1991.

Kitto and Janick, "Production of Synthetic Seeds by Encapsulating Asexual Embryos of Carrot," *J. Amer. Soc. Hort. Sci.* 110(2):277–282, 1985.

Gray, "Quiescene in Monocytledonous and Dicotyledonous Somatic Embryos Induced by Dehydration," *Hortscience* 22(5):810–814, 1987.

Gray et al., "Desiccated Quiescent Somatic Embryos of Orchardgrass for use as Synthetic Seeds," *In Vitro Cellular & Developmental Biology* 23(1):29–33, 1987.

Anandarajah and McKersie, "Manipulating the desiccation tolerance and vigor of dry somatic embryos of *Medicago sativa* L. with sucrose, heat shock and abscisic acid," *Plant Cell Reports* 9:451–455, 1990.

Senaratna et al., "Desiccation of microspore derived embryos of oilseed rape (*Brasicca napus* L.)," *Plant Cell Reports* 10:342–344, 1991.

Anandarajah et al., "Inductioni of desiccation tolerance in microspore–derived embryos of *Brassica napus* L. by thermal stress," *Plant Science* 77:119–123, 1991.

Kriezek, "Methods of Inducing Water Stress in Plants," *Hortscience* 20(6):1028–1038, 1985.

Cress and Johnson, "The effect of three osmotic agents on free proline and amino acid pools in *Atriplex canescens* and *Hilaria jamesii*," *Can J. Bot.* 65:799–801, 1987.

Heyser and Nabors, "Growth, Water Content, and Solute Accumulation of Two Tobacco Cell Lines Cultured on Sodium Chloride, Dextran, and Polyethylene Glycol," *Plant Physiol.* 68:1454–1459, 1981.

Michel and Kaufmann, "The Osmotic Potential of Polyethylene GLycol 6000," *Plant Physiol.* 51:914–196, 1973.

Bodsworth and Bewley, "Osmotic priming of seeds of crop species with polyethylene glycol as a means of enhancing early and synchronous germination at cool temperatures," *Can. J. Bot.* 59:672–676, 1981.

Oertli, "The response of Plant Cells to Different Forms of Moisture Stress," *J. Plant Physiol.* 121:295–300, 1985.

Lu and Thorpe, "Somatic Embryogenesis and Plantlet Regeneration in Cultured Immature Embryos of *Picea glauca*," *J. Plant. Physiol.* 128:297–302, 1987.

Roberts et al., "Abscisic acid and indole–3–butyric acid regulation of maturation and accumulation of storage proteins in somatic embryos of interior spruce," *Physiologia Planatarum* 78:1–6, 1990.

Afele et al., "Somatic embyogenesis and plant regeneration from zygotic embryo culture in blue spruce (*Picea pungens* Engelman.)," *Plant Cell Reports* 11:299–303, 1992.

Roberts et al., "Synchronous and high frequency germination of interior spruce somatic embryos following partial drying at high relative humidity," *Can J. Bot.* 68:1086–1090, 1990.

Chalupa, "Plant Regeneration by Somatic Embryogenesis in Norway Spruce (*Picea Abies* /L./Karst.) and Sessile Oak (*Quercus Petraea*/Matt./Lielbl.)," *Communications Instituti Forestalis Cechoslovaca* 16:135–143, 1989.

Dunstan, "Prospects and progress in conifer biotechnology," *Canadian Journal of Forest Research* 18(12):1497–1506, 1988.

Denchev et al., "A new approach to direct somatic emyogenesis in Medicago," *Plant Cell Reports* 10:338–341, 1991.

Flinn et al., "Storage protein changes during zygotic embryogenesis in interior spruce," *Tree Physiology* 8:71–81, 1991.

Pammenter et al., "Homeohydrous (Recalcitrant) Seeds: Dehydration, the State of Water and Viability Characteristics in *Landolphia kirkii*," *Plant Physiol.* 96:1093–1098, 1991.

Gupta et al., "Development of an Embryogenic System for Automated Propagation of Forest Trees," in Indra K. Vasil (ed.), *Scale–Up And Automation In Plant Propagation*, Academic Press, Inc., 1991, 75–93.

Tautorus et al., "Bioreactor culture of *Picea mariana* Mill. (black spruce) and the species complex *Picea glauca–engelmanni* (interior spruce) somatic embryos. Growth parameters," *Applied Microbiology and Biotechnology* 38:46–51, 1992.

Saranga et al., "Changes in Amino Acid Composition Associated with Tolerance to Partial Desiccation of Celery Somatic Embryos," *J. Amer. Soc. Hort. Sci.* 117(2):337–341, 1992.

Kim and Janick, "Somatic Embyogenesis and Organogenesis in Cucumber," *Hortscience* 24(4):p. 702, 1989.

Kim and Janick, "ABA and Polyox–encapsulation or High Humidity Increases Survival of Desiccated Somatic Embryos of Celery," *Hortscience* 24(4):674–676, 1989.

Kermode and Bewley, "Developing Seeds of *Ricnius communis* L., When Detached and Maintained in an Atmosphere of High Relative Humidity, Switch to a Germinative Mode without the Requirement for Complete Desiccation," *Plant Physiol.* 90:702–707, 1989.

Jensen and Lixue, "Abies seed protein profile divergent from other Pinaceae," *Taxon* 40:435–440, 1991.

Hakman and Arnold, "Plantlet Regeneration through Somatic Embryogenesis in *Picea abies* (Norway Spruce)," *J. Plant Physiol.* 121:149–158, 1985.

Becwar et al., "A method for quantification of the level of somatic embyogenesis among Norway spruce callus lines," *Plant Cell Reports* 6:35–38, 1987.

Bonga, "In Vitro Propagation of conifers: Fidelity of the Clonal Offspring," in M. R. Ahuja (ed.), *Woody Plant Biotechnology*, Plenum Press, New York, 1991, pp. 13–21.

Fourré et al., "In Vitro Germination of Encapsulated Picea abies (L.) Karst. Somatic Embryos: Preliminary Result," *Med. Fac. Landbouww. Rijksuniv. Gent* 56(4a):1449–1451, 1991.

Jain et al., "Somatic Embryogenesis in Slash Pine (*Pinus Elliotti*) From Immature Embyos Cultured In Vitro," *Plant Science* 65:233–241, 1989.

Becwar et al., "Somatic embryo development and plant regeneration from embryogenic Norway spruce callus," *Tappi Journal* 60(4):155–160, 1987.

Webb et al., "Factors influencing the induction of embryogenic and caulogenic callus from embyos of *Picea glauca* and *P. engelmanii*," *Can. J. For. Res.* 19:1303–1308, 1989.

Gupta et al., "Plantlet Regeneration Via Somatic Embyogenesis From Subcultured Callus of Mature Embryos of *Picea Abies* (Norway Spruce)," *In Vitro Cellular & Developmental Biology* 22(11):685–688, 1986.

Budimir and Vujicic, "Benzyladenine induction of buds and somatic embryogenesis in *Picea omorika* (Pancic) Purk," *Plant Cell Tissue and Organ Culture* 31:89–94, 1992.

Hakman and Fowke, "Somatic embryogenesis in *Picea glauca* (white spruce) and *Picea mariana* (Black spruce)," *Can. J. Bot.* 65:656–659, 1987.

Mullin and Park, "Estimating genetic gains from alternative breeding strategies for clonal forestry," *Canadian Journal of Forest Research* 22(1):14–23, 1992.

Gates and Greenwood, "The Physical and Chemical Environment of the Developing Embryo of Pinus Resinosa," *American Journal of Botany* 78(7):1002–1009, 1991.

Tsang et al., "Toxicity of antibiotics on zygotic embryos of white spruce (*Picea glauca*) cultured in vitro," *Plant Cell Reports* 8:214–216, 1989.

Finer et al., "Initiation of embryogenic callus and suspension cultures of eastern white pine (*Pinus strobus* L.)," *Plant Cell Reports* 8:203–206, 1989.

Newton et al., "Vicilian–like storage proteins in the gymnosperm interior spruce (*Picea glauca/engelmanii*)," *Plant Molecular Biology* 20:315–322, 1992.

Lelu and Bornman, "Induction of somatic embyogenesis in excised cotyledons of *Picea glauca* and *Picea mariana*," *Plant Physiol. Biochem.* 28(6):785–791, 1990.

Aitken–Christie and Connett, "Micropropagation of Forest Trees," in Kurata and Kozai (eds.), *Transplant Production Systems*, Kluwer Academic Publishers, 1992, 163–194.

Chalupa, "Somatic Embryogenesis and Plant Regeneration in Picea, Quercus, Betula, Tilia, Robinia, Fagus, and Aesculus," *Communications Instituti Forestalis* 15:133–148, 1987.

Nagmani and Bonga, "Embryogenesis in subcultured callus of *Larix decidua*," *Can. J. For. Res.* 15:1088–1091, 1985.

Ruaud et al., "First evidence of somatic embyrogenesis from needles of 1–year–old *Picea abies* plants," *Plant Cell Reports* 11:563–566, 1992.

Pitel et al., "Changes in enzyme activity and protein patterns during the maturation phase of somatic embyogenesis in hybrid larch (*Larix xeurolepis*)," *Can. J. For. Res.* 22:553–560, 1992.

Chalupa, "Somatic Embryogenesis and Plantlet Regeneration from Cultured Immature and Mature Embryos of Picea Abies (L.) Karts," *Communications Instituti Forestalis* 14:57–63, 1985.

Chavez et al., "Somatic Embryogenesis From Leaf Callus of Mature Plants of the Gymnosperm *Ceratozamia Mexicana* Var. Robusta (Miq.) Dyer (Cycadales)," *In Vitro Cell Dev. Biol.* 28P:59–63, 1992.

Berceteche et al., "Efficient regeneration of plantlets from embryonic callus of *Picea abies* (L.) Karst after freezing in liquid nitrogen," *C. R. Acad. Sci. Paris* 310(Série III):357–363, 1990.

Newton et al., "Expression of an abscisic acid responsive promoter in *Picea abies* (L.) Karst. Following bombardment from an electric discharge particle accelerator," *Plant Cell Reports* 11:188–191, 1992.

Whitmore, "Stored messenger RNA and stratification in eastern white pine (*Pinus strobus* L.)," *Seed Sci. & Technol.* 19:341–346, 1991.

Lulsdorf et al., "Growth parameters of embryogenic suspension cultures of interior spruce (*Picea glauca–engelmanni* complex) and black spruce (*Picea mariana* Mill.)," *Plant Science* 82:227–234, 1992.

Kartha et al., "Induction of Somatic Embryos and Plantlets from Cryopreserved Cell Cultures of White Spruce (*Picea glauca*)," *J. Plant Physiol.* 132:529–539, 1988.

Schuller et al., "Somatic embryogenesis from seed explants of *Abies alba*," *Plant Cell. Tissue and Organ Culture* 17:53–58, 1989.

Jain et al., "Enhancement of somatic embryogenesis in Norway spruce (*Picea abies* L.)," *Theor Appl Genet* 76:501–506, 1988.

Chavez et al., "Somatic embryogenesis and organogenesis in *Zamia fischeri, Z. furfuracea* and *Z. pumila*," *Plant Cell, Tissue and Organ Culture* 30:99–105, 1992.

Hartmann et al., "Differentiation of somatic embryos from protoplasts isolated from embryonic suspension cultures of *Abies alba* L.," *Plant Cell Reports* 11:554–557, 1992.

Attree et al., "Somatic embryo maturation, germination, and soil establishment of plants of black and white spruce (*Picea mariana* and *Picea glauca*)," *Can. J. Bot.* 68:2583–2589, 1990.

Tautorus et al., "Somatic embryogenesis in conifers," *Can. J. Bot.* 69:1873–1899, 1991.

Nagmani et al., "Effect of Explaint and Media on Initiation, Maintenance," in M.R. Ahuja (ed.), *Woody Plant Biotechnology*, Plenum Press, 1991, 171–179.

Bellarosa et al., "The Influence of Auxin and Cytokin on Proliferation and Morphology of Somatic Embryos of *Picea abies* (L.) Karts," *Annals of Botany* 70:199–206, 1992.

Hakman and Fowke, "An embryogenic cell suspension culture of *Picea glauca* (White spruce)," *Plant Cell Reports* 6:20–22, 1987.

Kvaalen and von Arnold, "Effects of various partial pressures of oxygen and carbon dioxide on different stages of somatic embryogenesis in *Picea abies*," *Plant Cell, Tissue and Organ Culture* 27:49–57, 1991.

Ellis et al., "Expression of inducible angiosperm promoters in a gymsosperm, *Picea glauca* (white spruce),"*Plant Moleclar Biology* 17:19–27, 1991.

von Arnold, "Improved Efficiency of Somatic Embryogenesis in Mature Embryos of *Picea abies* (L.) Karts," *J. Plant. Physiol.* 128:233–244, 1987.

Gupta et al., "Somatic Proembryo Formation and Transient Expression of a Luciferase Gene in Douglas Fir and Loblolly Pine Protoplasts," *Plant Science* 58:85–92, 1988.

Becwar et al., "Initiation of embryogenic cultures and somatic embryo development in loblolly pine (*Pinus taeda*)," *Can. J. For. Res.* 20:810–817, 1990.

Salajova and Salaj, "Somatic embryogenesis in European black pine (*Pinus nigra* Arn.)," *Biologia Plantarum* 34:213–218, 1992.

Webster et al., "Propagation of interior spruce by somatic embryogenesis," *Can. J. For. Res.* 20:1759–1765, 1990.

Charest et al., "Transient expression of foreign chimeric genes in the gymnosperm hybrid larch following electroporation," *Can. J. Bot.* 69:1731–1736, 1991.

Lainéet al., "Recovery of plants from cryopreserved embryogenic cell suspension of *Pinus caribaea*," *Plant Cell Reports* 11:295–298, 1992.

Berlyn et al., "Caribbean Pine (*Pinus caribaea* Morelet)," *Biotechnology in Agriculture and Forestry* 16:256–266, 1991.

Wann et al., "Biochemical differences between embryogenic and nonembryogenic callus of *Picea abies* (L.) Karst," *Plant Cell Reports* 6:39–42, 1987.

Boulay et al., "Developmental of somatic embryos from cell suspension cultures of Norway spruce (*Picea abies* Karts.)," *Plant Cell Reports* 7:134–137, 1988.

von Arnold and Hakman, "Effect of Sucrose on Initiation of Embryogenic Callus Cultures from Mature Zygotic Embryos of *Picea abies* (L.) Karst. (Norway Spruce)," *J. Plant Physiol.* 122:261–265, 1986.

Allona et al., "Seed storage proteins from *Pinus pinaster* Ait.: homology of major components wiht 11S proteins from angiosperms," *Plant Science* 87:9–18, 1992.

Groome et al., "Hydrolysis of lipid and protein reserves in loblolly pine seeds in relation to protein electrophoretic patterns following imbibition," *Physiologia Plantarum* 83:99–106, 1991.

Krogstup, "Effect of culture densities on cell proliferation and regeneration from embryogenic cell suspensions of *Picea sitchensis*," *Plant Science* 72:115–123, 1990.

Jalonen and von Arnold, "Characterization of embryogenic cell lines of *Picea abies* in relation to their competence for maturation," *Plant Cell Reports* 10:384–387, 1991.

Gupta et al., "Somatic polyembryogenesis in embryogenic cell masses of *Picea abies* (Norway spruce) and *Pinus taeda* (loblolly pine) after thawing from liquid nitrogen," *Can. J. For. Res.* 17:1130–1134, 1987.

Dunstan et al., "Effects of Abscisic Acid and Analogues on the Maturation of White Spruce (*Picea Glauca*) Somatic Embryos," *Plant Science* 58:77–84, 1988.

Dunstan et al., "Metabolism of(+)–And (−)–Abscisic Acid by Somatic Embryo Suspension Cultures of White Spruce," *Phytochemistry* 31(5):1451–1454, 1992.

Duchesne and Charest, "Effect of promoter sequence on transient expression of the α–glucuronidase gene in embryogenic calli of *Larix x eurolepis* and *Picea mariana* following microprojection," *Can. J. Bot.* 70:175–180, 1992.

Hämäläinen and Jokinen, "Selection of Norway spruce somatic embryos by computer vision," *SPIE Proceedings* 1836:195–205, 1992.

Hakman and von Arnold, "Somatic embryogenesis and plant regeneration from suspension cultures of *Picea glauca* (White spruce)," *Physiologia Plantarum* 72:579–587, 1988.

von Arnold and Hakman, "Regulation of Somatic Embryo Development in *Picea abies* by Abscisic Acid (ABA)," *J. Plant Physiol.* 132:164–169, 1988.

Bekkaoui et al., "Transient gene expression in electroporated *Picea glauca* protoplasts," *Plant Cell Reports* 7:481–484, 1988.

Attree ete al., "Plantlet Regeneration From Embryogenic Protoplasts of White Spruce (*Picea Glauca*)," *Bio/Technology* 7:1060–1062, 1989.

Klimaszewska, "recovery of somatic embryos and plantlets from protoplast cultures of *Larix x eurolepis*," *Plant Cell Reports* 8:440–444, 1989.

Lang and Kohlenbach, "Cell differentiation in protoplast cultures from embryogenic callus of *Abies alba* L.," *Plant Cell Reports* 8:120–123, 1989.

Becwar et al., "Maturation, Germination, and Conversion of Norway Spruce (*Picea Abies* L.) Somatic Embryos to Plants," *In Vitro Cellular & Developmental Biology* 25(6):575–580, 1989.

Misra and Green, "Developmental gene expression in conifer embryogenesis and germination. II. Crystalloid protein synthesis in the developing embryo and megagametophyte of white spruce (*Picea glauca* [Moench] Voss.)," *Plant Science* 78:61–71, 1991.

Tautorus et al., "Factors affecting transient gene expression in electroporated black spruce (*Picea mariana*) and jack pine (*Pinus banksiana*) protoplasts," *Theor Appl Genet* 78:531–536, 1989.

Santanen and Simola, "Changes in Polyamine Metabolism during Somatic Embryogenesis in *Picea abies*," *J. Plant Physiol.* 140:475–480, 1992.

Bourgkard and Favre, "Somatic embryos from callus of *Sequioia sempervirens*," *Plant Cell Reports* 7:445–448, 1988.

Joy et al., "Long–term storage of somatic embryogenic white spruce tissue at ambient temperature," *Plant Cell, Tissue and Organ Culture* 25:53–60, 1991.

Simola and Honkanen, "Organogenesis and fine structure in megagemetophyte callus lines of *Picea abies*,"*Physiol. Plant.* 59:551–561, 1983.

von Arnold and Woodward, "Organogenesis and embryogenesis in mature zygotic embryos of *Picea sitchensis*," *Tree Physiology* 4:291–300, 1988.

Joy et al., "Development of White Spruce Somatic Embryos: I. Storage Product Deposition," *In Vitro Cell Dev. Biol.* 27P:32–41, 1991.

Ishii, "Somatice Embryo Formation and Plantlet Regeneration through Embryogenic Callus from Mature Zygotic Embryos of *Picea jezoensis*var. *Hondoensis, Picea jezoensis,* and *Picea glehnii*," *J. Jpn. For. Soc.* 73(1):24–28, 1991.

Kong and Yeung, "Development of White Spruce Somatic Embryos: II. Continual Shoot Meristem Development During Germination," *In Vitro Cell Dev. Biol.* 28P:125–131, 1992.

Krogstrup et al., "Somatic embryogenesis in Sitka spruce (*Picea sitchensis* (Bong.) Carr.)," *Plant Cell Reports* 7:594–597, 1988.

Stomp et al., "Transient expression from microprojectile–mediated DNA transfer in *Pinus taeda*," *Plant Cell Reports* 10:187–190, 1991.

Bozhkov et al., "A pronounced synergetic effect of abscisic acid and 6–benzyladenine on Norway spruce (*Picea abies* L. Karts) somatic embryo maturation," *Plant Cell Reports* 11:386–389, 1992.

Bekkaoui et al., "The isolation and culture of protoplasts form an embryogenic cell suspension culture of *Picea glauca* (Moench) Voss.," *Plant Cell Reports* 6:476–479, 1987.

Hakman et al., "Storage protein accumulation during zygotic and somatic embryo development in *Picea abies* (Norway spruce)," *Physiologia Plantarum* 80:441–445, 1990.

Hakman et al., "A Light and Electron Microscope Study of *Picea glauca* (White Spruce) Somatic Embryos," *Protoplasm* 140:100–109, 1987.

Laine and David, "Somatic Embryogenesis in Immature Embryos and Protoplasts of *Pinus Carbaea*," *Plant Science* 69:215–224, 1990.

Cheliak and Klimaszewska, "Genetic variation in somatic embryogenic response in open–pollinated families of black spruce," *Theor Appl Genet* 82:185–190, 1991.

Tremblay and Tremblay, "Effects of gelling agents, ammonium nitrate, and light on the development of *Picea mariana* (Mill) B.S.P. (black spruce) and *Picea rubens* Sarg. (red spruce) somatic embryos," *Plant Science* 77:233–242, 1991.

Klimaszewska, "Plantlet Development from Immature Zygotic Embryos of Hybrid Larch Through Somatic Embryogenesis," *Plant Science* 63:95–103, 1989.

Robertson et al., "Genetic transformation of Norway spruce (*Picea abies* (L.) Karst): somatic embryo explants by microprojectile bombardment," *Plant Molecular Biology* 19:925–935, 1992.

Norgaard and Krogstrup, "Cytokinin induced somatic embryogenesis from immature embryos of *Abies nordmanniana* Lk.," *Plant Cell Reports* 9:509–513, 1991.

Gifford, "An electrophoretic analysis of the seed proteins from *Pinus monticola* and eight other species of pine," *Can. J. Bot.* 6:1808–1812, 1988.

Hutchinson and Greenwood, "Molecular approaches to gene expression during conifer development and maturation," *Forest Ecology and Management* 43:273–286, 1991.

Norstog and Rhamstine, "Isolation and Culture of Haploid and Diploid Cycad Tissues," *Phytomorphology* 17:374–381, 1967.

Ching, "Compositional Changes of Douglas Fir Seeds During Germination," *Plant Physiol.* 41:1313–1315, 1965.

Bekkaoui and Dunstan, "Permeabilization of *Picea glauca* protoplasts to macromolecules," *Can. J. For. Res.* 19:1316–1321, 1989.

Norstog, "Induction of Apogamy in Megagametophytes of Zamia Integrifolia," *Amer. Jour. Bot.* 52(10):993–999, 1965.

Johnson et al., "Biochemical Changes Associated with Zygotic Pine Embryo Development," *Journal of Experimental Botany* 38(188):518–524, 1987.

Tremblay, "Somatic embryogenesis and plantlet regeneration from embryos isolated from stored seeds of *Picea glauca*," *Can. J. Bot.* 68:236–242, 1990.

Duchesne and Charest, "Transient expression of the β–glucuronidase gene in embryogenic callus of *Picea mariana* following microprojection," *Plant Cell Reports* 10:191–194, 1991.

Klimaszewska et al., Cryopreservation and Plant Regeneration from Embryonic Cultures of Larch (*Larix X eurolepis*) and Black Spruce (*Picea mariana*), *Journal of Experimental Botany* 43(246):73–79, 1992.

Lelu et al., "Somatic embryogenesis in cotyledons of *Picea abies* is enhanced by an adventitious bud–inducing treatment," *New Forests* 4:125–135, 1990.

Dunstan et al., "Racemic abscisic acid and abscisyl alcohol promote maturation of white spruce (*Picea glauca*) somatic embryos," *Plant Science* 76:219–228, 1991.

Verhagen and Wann, "Norway spruce somatic embryogenesis: high frequency initiation from light–cultured mature embryos," *Plant Cell, Tissue and Organ Culture* 16:103–111, 1989.

Kovach and Bradford, "Imbibitional Damage and Desiccation Tolerance of Wild Rice (*Zizania palustris*) Seeds," *Journal of Experimental Botany* 43(251):747–757, 1992.

Kermode, "Regulatory Mechanisms Involved in the Transition from Seed Development to Germination," *Critical Reviews in Plant Sciences* 9(2):155–195, 1990.

Skriver and Mundy, "Gene Expression in Response to Abscisic Acid and Osmotic Stress," *The Plant Cell* 2:503–512, 1990.

Gray and Purohit, "Quiescence and Dormancy in Somatic Embryos," *Biotechnology in Agriculture and Forestry* 17:382–394, 1991.

Shimonishi et al., "Cryopreservation of melaon somatic embryos by disiccation method," *Japan. J. Breed.* 41(2):347–351, 1991.

Xu et al., "Abscisic acid and osmoticum prevent germination of developing alfalfa embryos, but only osmoticum maintains the synthesis of developmental proteins," *Planta* 182:382–390, 1990.

Siddeswar and Kishor, "Plant Regeneration From Polytehyleneglycol Adapted Callus of Rice," *Current Science* 58(16):926–928, 1989.

Blackman et al., "Maturation Proteins Associated with Desiccation Tolerance in Soybean," *Plant Physiol.* 96:868–874, 1991.

Hammat and Davey, "Somatic Embryogenesis and Plant Regeneration from Cultured Zygotic Embryos of Soybean (*Glycine max* L. Merr.)," *J. Plant. Physiol.* 128:219–226, 1987.

Carpita et al., "Determination of the Pore Size of Cell Walls of Living Plant Cells," *Science* 205:1144–1147, 1979.

Berry and Bewley, "Seeds of tomato (*Lycopersicon esculentum* Mill.) which develop in a fully hydrated environment in the fruit switch from a developmental to a germinative mode without a requirement for desiccation," *Planta* 186:27–34, 1991.

Bruni and Leopold, "Glass Transitions in Soybean Seed. Relevance to Anhydrous Biology," *Plant Physiol.* 96:660–663, 1991.

PRODUCTION OF DESICCATION-TOLERANT GYMNOSPERM EMBRYOS

RELATED APPLICATIONS

This application is a continuation of U.S. patent application Ser. No. 08/244,725 filed on Aug. 18, 1994 now U.S. Pat. No. 5,985,667. That application was filed as PCT Application No. PCT/CA92/00549 filed on Dec. 18, 1992, and a CIP of U.S. patent application Ser. No. 08/159,693 filed Dec. 1, 1993 which issued as U.S. Pat. No. 5,464,769 which is a continuation of Ser. No. 07/810,171 filed Dec. 1, 1991, now abandoned. U.S. patent application Ser. No. 08/244,725 now abandoned and U.S. Pat. No. 5,464,769 are hereby incorporated by reference in their entirety.

FIELD OF THE INVENTION

The invention relates to somatic embryo production, particularly to methods for maturing and desiccating gymnosperm somatic embryos.

BACKGROUND OF THE INVENTION

Somatic embryogenesis offers the potential to produce clonally large numbers of low cost plants of many species. Somatic embryos develop without the surrounding nutritive tissues and protective seed coat, so considerable research has been devoted to causing somatic embryos to functionally mimic seeds with regard to efficient storage and handling qualities. The development of techniques for somatic embryogenesis in conifers has greatly improved the ability to culture conifer tissues in vitro and now offers the means to propagate clonally commercially valuable conifers of a number of species. However, all conifer species suffer from poor plantlet vigor.

It has been suggested to use abscisic acid (ABA) or osmoticum for enhancing storage levels in plant cells. For example, it was shown that somatic embryos of *Theobroma cacao* could be induced to accumulate fatty acids approaching the composition of commercial cocoa butter by increasing the sucrose concentration of the culture medium. Modifying the culture conditions by varying osmotic concentration and/or ABA content similarly improved lipid accumulation in *Brassica napus* L. somatic and microspore derived embryos as well as somatic embryos of carrot and celery. Also, the level of storage lipids in P. abies somatic embryos was improved by optimizing the ABA level to between 10–20 $\mu$m, but the somatic embryos contained about 4% of the lipid level obtained by zygotic embryos.

Also, Japanese laid-open patent publication No. 1-218520 describes a process for producing plant body regenerative tissue. The process includes a step of cultivating a plant body regenerative tissue in a medium containing ABA and having an osmotic pressure of 180 to 2500. In order to control the osmotic pressure within the specific range, a non-toxic substance such as sugar, alcohol, an amino acid or glycol is added.

Water stress plays an important role in maintaining embryos in a maturation state (Kermode 1990, Crit. Res. Plant Sci. 9, 155–194). Low water content rather than ABA prevents precocious germination during later stages of development. This is important because precocious germination of embryos during development in seeds would be lethal during desiccation.

A conventional way to water stress plant cells grown in vitro is to increase the osmotic concentration of the culture medium through the use of plasmolysing osmotica. For example, increased concentrations of plasmolysing osmotica such as sucrose have been used to promote somatic embryo maturation of many plant species. Sucrose at levels up to 6% was found to improve somatic embryo development of some conifers but a smaller increase in sucrose from 1 to 3% was previously considered optimal for the maturation of white and Norway spruce somatic embryos. It seems that a higher concentration generally led to repressed embryo development. 3% sucrose is the concentration most commonly used for conifer somatic embryo maturation. Mannitol had a similar effect on maturation of conifer somatic embryos (Roberts 1991). Low levels of mannitol (2–6%) led to a doubling of the number of mature embryos recovered at the end of the maturation period; however, the treatment could only be applied as a short pulse (1 week) as prolonged maturation treatment with mannitol became detrimental to further embryo maturation.

Poor response using sucrose and mannitol or other simple sugars and salts may be because such plasmolysing osmotica are absorbed by the symplast of plant cells. Such absorption facilitates adjustment of tissue osmotic potential (osmotic recovery) without lowering the tissue water content. Additionally, direct or indirect metabolic effects on specific plant metabolites can occur, due to utilization of the solute or its toxic effects.

Alternatives to plasmolysing osmotica are non-permeating high molecular weight compounds such as polyethylene glycol (PEG) or dextran. These compounds are usually available in a wide range of molecular weights. For example, PEG is available in molecular weights ranging from 200 to 35,000. However, only those with a molecular weight above 1000 to 3000 would be non-permeating (Carpita et al, 1979). This is because the large molecular size of these solutes excludes their passage through plant cell walls, so preventing entry into cells and plasmolysis, while still removing water. Consequently, their non-plasmolysing effect reduces tissue water content in a manner similar to the effects of water stress observed in cells of plants subjected to drought conditions. The effect is constant and cell turmor can only be restored by cells actively increasing their cellular solute concentrations. PEG has been most commonly used to apply water stress to whole plants, to osmotically prime whole seeds to synchronize germination and improve seedling vigor.

Embryo drying occurs naturally in most seeds, and has a role to play in the developmental transition between maturation and germination. Thus, desiccation led to enhanced germination of both zygotic and somatic embryos. Desiccation of whole somatic embryos is also an alternative method of germplasm storage. Somatic embryos produced continuously year-round could therefore be dried and stored until the appropriate planting season, or shipped to new locations.

A number of prior publications describe methods for the desiccation of angiosperm somatic embryos. Senaratna et al., in EP application 0300730, describe a method through which in vitro formed plant embryos are desiccated following the application of ABA or other types of environmental stress inducing desiccation tolerance. The angiosperm embryos are induced at the torpedo shaped stage with the source of ABA for a sufficient period of time to cause expression of desiccation tolerance. The induced embryos are then dried to provide stable, viable artificial seeds. In EP 0300730, Senaratna et al. emphasize on the importance of stimulating the embryo at the appropriate stage by the use of signals to develop tolerance to desiccation. It is stressed that if the signals are applied at the incorrect stage of development, the tissue will not respond properly. Angiosperm embryos can undergo maturation in the absence of ABA and it is suggested that ABA be supplied as late as possible during the maturation protocol and applied for a relatively short period of time. Hence, the timing and duration of ABA application seem to be critical.

Japanese laid-open patent publication No. 2-31624 discloses the use of ABA in plant cultures. ABA is used as part of a process for drying embryos prior to storage.

In published PCT specification No. WO 89/05575, a method for the production of synthetic seeds comprising dehydrated somatic embryos is described. The method, which is applicable to monocotyledonous and dicotyledonous embryos, comprises maintaining the somatic embryos in an atmosphere having a relative humidity (r.h.) of from about 30 to about 85% for a period of time sufficient to reduce the moisture content of the embryos from about 85 to 65% to about 4 to 15%. The use of osmotically active materials, once the embryos are matured, is suggested.

Senaratna et al., in 1989, Plant Science, 65, pp. 253–259, describe the induction of desiccation tolerance in alfalfa somatic embryos by exogenous application of ABA in the form of a short pulse. Embryos are then dried to 10 to 15% of their moisture content and stored for at least 3 weeks in the dry state. Senaratna et al. also describe a method by which tolerance to desiccation is induced by exposing the somatic embryos to sub-lethal levels of low temperature, water, nutrient or heat stress prior to desiccation. However, it was demonstrated that some of these stress pre-treatments had deleterious effects on embryo maturation and seedling vigor.

Hence, the prior literature on somatic embryos and artificial seeds shows that desiccation tolerance has been achieved in some angiosperm plant species such as alfalfa, geraniums, celery, brassica, carrots, corn, lettuce, orchardgrass and soybeans. Various methods have been suggested, which all appear to evolve around promoting desiccation tolerance by applying ABA and other stresses late in maturation and subsequently reducing the water content of the embryos. However, survival following desiccation of conifer somatic embryos has, at present, not been reported, as these methods are not applicable to conifers.

The creation of artificial seeds in which somatic embryos are encapsulated in a hydrated gel has also been described. The encapsulated embryos may then be planted using traditional seed planters. The major drawback of encapsulation in a hydrated gel is the fact that it allows only limited storage duration. The following are examples of hydrated gels for encapsulation.

Japanese laid-open patent publication No. 2-46240 discloses a method by which an oxygen supplying substance is used to coat a plant embryo. The document also refers to the possible use of a water-soluble polymeric substance together with the oxygen supplying compound. Preferred oxygen supplying compounds are calcium perchlorate or barium perchlorate. The water soluble polymeric substances referred to are hydrated gels of sodium alginate, gelatin, mannan, polyacrylamide and carboxymethyl cellulose.

In Japanese laid-open patent publication No. 63-133904, a method is described to coat plant embryos and nutrients with a water-soluble polymeric substance such as alginic acid and polyacrylamide. Polyethylene glycol is mentioned as an example of polymeric substance that can be used together with the water-soluble polymeric substances.

Japanese laid-open patent publication No. 61-40708 describes a technique through which an embryo is encapsulated with nutrients, an anti-bacterial agent and a water-soluble polymeric substance which may include cross-linked polyethylene glycol. The role of the water-soluble polymer appears to be to keep moisture during storage of the encapsulated embryo.

In U.S. Pat. No. 4,615,141, Janick and Kitto describe a method for encapsulating asexual plant embryos. In this method, the embryos are pre-treated by increasing the sucrose concentration of the maintenance medium from normal levels to high levels, or by applying ABA. The hydrated embryos are then encapsulated in a hydrated coating material. The coating material dries to form a thin, non-toxic film enclosing one or more embryos, protecting the embryos during storage but readily redissolving in an aqueous solution. The use of ABA and increased sucrose is suggested to improve survival of the encapsulated embryos. Once the embryos have been encapsulated, they are dried at a temperature ranging from 20 to 30° C. for a period of at least 5 hours.

In U.S. Pat. No. 4,777,762, Redenbaugh et al. describe a method for producing desiccated analogs of botanic seeds which are created by removing a portion of the water by slow or fast drying so that the plant tissue is no longer saturated with water. The method also involves encapsulating meristematic tissue in a hydrated gel or polymer and removing water by slow or fast drying. The formation of somatic embryos is induced and the embryos are then encapsulated in the gel or polymer followed by drying. Alternatively, the somatic embryos are desiccated to less than complete tissue saturation during, or at the end of, embryo development then encapsulated.

When the gels described above are used to encapsulate the somatic embryos either before or after dehydration, preferred gels are selected from hydrogels or polymers which contain water within the confines of the gel matrix but which can be dried as the plant tissue is being desiccated. One of the disadvantages of such a method is that controlled drying of the encapsulated embryos is difficult to achieve. In most instances double drying of embryos is necessary. Thus, desiccated embryos are encapsulated in the hydrogel, which leads to rehydration, then the embryos are redesiccated. Recently published data shows that somatic embryos encapsulated in hydrated gel without desiccation have a storage life restricted to a few months, even when refrigerated at above freezing temperatures.

In a 1991 review article concerning somatic embryogenesis and development of synthetic seed technology (Critical Reviews in Plant Sciences 10:33–61, 1991), Gray et al. mention that synthetic seed technology for the forest products industry would be extremely beneficial. This is because forest conifers can be propagated economically only from natural seed and since improvement via conventional breeding is extremely time consuming due to the long conifer life cycle.

There has been a trend for using increasingly higher concentrations of ABA to promote the maturation of conifer somatic embryos. This trend probably results from a need to inhibit precocious germination which has become more apparent following the increasingly longer maturation times being used. Thus ABA was first successfully used by Hakman and von Arnold 1988 (Physiol. Plant. 72:579–587) and von Arnold and Hakman 1988 (J. Plant Physiol. 132:164–169), at 7.6 $\mu$M. Dunstan et al. 1988 (Plant Sci. 58:77–84) subsequently found 12 $\mu$M ABA to be better. Shortly after, Attree et al. 1990 (Can. J. Bot. 68:2583–2589) reported that 16 $\mu$M was optimal. Roberts et al. 1990

(Physiologia Plantarum 78; 355–360) have shown that for some species of spruce, ABA at 30–40 μM could be used to promote maturation and yield mature embryos with storage protein polypeptides comparable to zygotic embryos. Such high levels were necessary to prevent precocious germination and allow maturation to proceed. Dunstan et al. 1991 (Plant Sci. 76:219–228) similarly found that high levels could permit embryo maturation. Unfortunately, high ABA levels also increased the frequency of developmentally abnormal embryos. In the above reports concerning conifers, increased osmoticum was not included with the ABA.

Conifer somatic embryos appear different to somatic embryos of monocotyledonous and dicotyledonous angiosperm species in that ABA should be supplied as early as possible in maturation protocols in order to promote embryo maturation. Merely reducing or eliminating auxin and cytokinin levels, as has been successful for maturation of somatic embryos of many angiosperm species (Ammirato 1983, Handbook of Plant Cell Culture, Vol. 1, pp. 82–123) led to infrequent or poor maturation in conifer embryos and more often resulted in browning and death of the immature somatic embryos. Furthermore, it appears that ABA should be applied for longer periods and at higher levels than generally applied to angiosperm somatic embryos.

In U.S. Pat. No. 5,036,382, Gupta et al. describe a method for developing tissue culture induced coniferous somatic embryos into well-developed cotyledonary embryos. The method comprises a multi-stage culturing process in which early stage embryos are cultured on a late stage medium comprising a significantly higher osmotic potential along with ABA and an absorbent material to gradually reduce the level of available ABA over time. A critical aspect of this method lies in the inclusion of the absorbent material in the embryo development medium. Absorbent materials suggested include activated charcoal and silicates. The absorbent is used to slowly reduce the ABA and remove metabolic waste products.

Gupta also suggests the use of osmoticants to control osmotic potential. A preferred osmoticant suggested is sucrose in amounts in the range of 2 to 3%. Another osmoticant that is suggested by Gupta et al. is PEG. Gupta et al. mention that PEG 8000 was evaluated and found to be a superior osmoticant, stating that the reasons for its superior performance compared with other materials is not entirely clear. Gupta et al. also suggest that polyethylene or polypropylene glycols of other molecular weights are believed to be equally useful. According to U.S. Pat. No. 5,036,007, the combination of osmoticants is to be modified at some point during the development stage. In fact, the osmotic concentration is gradually increased during development.

In U.S. Pat. Nos. 4,957,866 and 5,041,832, Gupta et al. describe a method for reproducing coniferous trees by somatic embryogenesis using plant tissue culture techniques. The method consists of placing coniferous somatic embryos in a maturation medium initially comprising no ABA and a low osmoticant concentration. ABA is then added and the levels of osmoticant are raised for the final stage of development. The osmoticants suggested by Gupta et al. are sugars such as sucrose, myo-inositol, sorbitol and mannitol.

In U.S. Pat. No. 5,034,326, Pulman et al. describe a method for reproducing coniferous plants by somatic embryogenesis using adsorbent materials in the development stage media. The adsorbent material (activated charcoal being a preferred embodiment) is used to gradually reduce the concentration of ABA present in the medium used in the development stage. The purpose of this reduction in ABA is to follow the natural tendency in embryo development. As development approaches completion, the presence of lesser amounts of ABA is required.

In PCT published specification WO 91/01629, Roberts describes a process for assisting germination of spruce somatic embryos that comprises partially drying the embryo at humidities of less than about 99.9%. Also described is a process to differentiate somatic embryos of conifers that comprises contacting embryogenic calli with a medium containing ABA. Roberts also suggests that a medium having a sucrose concentration of 2 or 3.4%t, which is used between the maturation treatments and the germination media, promotes root and shoot elongation. Roberts mentions that the humidity range that can be used for partial drying of somatic embryos without lethal effect is about 85 to 99.9% which results in only a very small (5–10%) moisture loss.

In a study published in Can. J. Bot., Vol. 68, 1990, pp. 1086–1090, Roberts et al. mention that conifer somatic embryos (interior spruce) do not survive desiccation at room humidity, but that partial drying at very high humidity promoted germination up to 90%. Roberts et al. also refer to the fact that drying embryos over a range of r.h. indicated that r.h. of 81% or lower was lethal to conifer embryos. This can be further visualized at Table 3 of the report where the effects of partial drying at different r.h. on germination are shown. It can be seen that very small levels of germination are obtained following drying at a r.h. of 90% and that no germination is observed when r.h. of 81% and 75% are used. Based on those results, Roberts concluded that only a mild drying of the somatic embryos was possible to permit normal germination and that the spruce somatic embryos did not tolerate desiccation to zygotic levels. Spruce somatic embryos did survive and undergo improved vigor following a partial drying treatment in an environment of very high humidity (over 95% humidity) during which time only 5% of moisture was removed.

Later, Roberts et al. (J. Plant Physiol., 138, pp. 1–6, 1991) emphasize that somatic embryos from a number of species, including spruce, are sensitive to severe water loss and show decreased survival following desiccation. In this paper, Roberts shows that Sitka spruce somatic embryos do not survive desiccation, even though high frequency and synchronized germination could be obtained following partial drying of the embryos.

Hence, despite attempts to desiccate conifer somatic embryos following ABA maturation, survival has not been described.

Desiccation of conifer somatic embryos would be desirable to enable somatic embryos to be stored for very long periods. Storage times of desiccated embryos may be further extended by storing frozen embryos. The ability to survive prolonged storage is important considering the long life cycles of conifers and the length of time required to evaluate in vitro produced trees. This would then be an alternative method of germplasm storage, from which somatic embryos could later be re-induced. Tissues able to survive freezing in liquid nitrogen are considered to be capable of survival following storage for indefinite periods.

For nearly all plant species, in vitro techniques are more costly in comparison to traditional methods of seeding. Somatic embryos also usually require pre-germination and greenhouse acclimatization prior to planting in the field. To overcome these problems, several methods have been suggested. Fluid drilling has been used for pre-germinated seeds. However, fluid drilling requires new planting techniques, specialized machinery and does not allow for precision at planting of embryos or plants.

In conclusion, the prior art would appear to suggest that currently available techniques have failed in providing strong conifer somatic embryos and desiccated conifer somatic embryos suitable for encapsulation. Conifer somatic embryos require particular plant growth regulator conditions in order to develop, and do not follow the developmental pattern of the more advanced angiosperms. Prior techniques involving short-term and transient application of ABA and osmotic treatments to developing embryos to achieve desiccation tolerance for conifers have not been satisfactory.

SUMMARY OF THE INVENTION

In accordance with the present invention, there is provided a method for producing desiccation-tolerant mature viable gymnosperm somatic embryos characterized by a moisture content of less than about 55%, by water stressing immature gymnosperm somatic embryos in the presence of (i) a metabolisable carbon source suitable for nourishing the immature embryos, and (ii) a selected growth regulator influencing embryo development. The rate of water loss of the embryos, the type and intensity of the water stressing, the length of time during which the water stressing occurs, and the type and concentration of the metabolizable carbon source and growth regulator are selected to reduce the moisture content of the embryos to a level of less than about 55%. Such embryos may have a dry weight and a per embryo lipid content higher than the lipid content and dry weight of corresponding zygotic embryos. The desiccation-tolerant embryos may also have substantially higher amounts of storage reserves than their zygotic counterparts. When used herein, the term "storage reserves" is intended to designate carbohydrates, proteins and lipids deposited by a maturing embryo for utilization during post-germinative growth.

The term "desiccated", when applied to gymnosperm somatic embryos, is intended to designate mature gymnosperm somatic embryos having a moisture content that is significantly lower (at least about 5% lower) than the moisture content of corresponding mature gymnosperm zygotic embryos from imbibed seed, which latter moisture content is usually greater than 60%. More specifically, desiccated somatic embryos obtained using the method of the present invention can be either "mildly" or "severely" desiccated. The "mildly desiccated" embryos are characterized by having a moisture content equal to or inferior to about 55%. With regard to the "severely desiccated" embryos, they are characterized by having either a moisture content which is equal to or less than the moisture content of corresponding zygotic embryos, or by being sufficiently devoid of free unbound water to permit the embryos to survive freezing. Usual water contents for "severely desiccated" embryos range from about 10% to about 36%.

While environmental water stressing and the use of non-osmotic water stress agents are optional in the practice of the invention, a preferred method according to the invention comprises applying a substantially non-plasmolyzing water stress to the embryos. Preferably, immature gymnosperm somatic embryos are developed (matured) in a medium comprising at least one non-permeating osmotic water stress agent, a metabolizable carbon source and a plant growth regulator having an influence on embryo development. Preferred gymnosperm somatic embryos produced according to the present invention are conifer somatic embryos. A preferred non-permeating osmotic water stress agent is polyethylene glycol of molecular weight at least about 1,000. When an osmotic water stress agent is used, the water stress should simulate a non-osmotic water stress. A preferred growth regulator is abscisic acid (ABA), but in contradistinction to prior teachings, the ABA concentration should preferably not decrease over the duration of the water stress treatment Once dessication-tolerant mature somatic embryos of reduced moisture content have been obtained, if it is desired to further desiccate the embryos, further osmotic stress may be applied, by increasing the concentration of the non-permeating water stress agent present in the medium or by drying the embryos by submitting them to at least one environment of low relative humidity to yield desiccated somatic embryos having a lower moisture content, preferably at least as low as about 45%. The moisture content may be substantially lower than the moisture content of corresponding zygotic embryos. Preferred moisture contents range between about 10 and 36%. Severe desiccation by drying can be achieved either through rapid drying or slow desiccation treatments in which the embryos are submitted to a series of environments having a decreasing relative humidity.

Also within the scope of the present invention is an optional method for encapsulating mature gymnosperm somatic embryos, zygotic embryos or desiccated somatic embryos. The method comprises coating the embryos with a non-hydrated water soluble compound having a melting point ranging between 20 and 70° C. The compound is then solidified to yield hardened capsules containing the embryo. This yields coated embryos having an enhanced resistance to attacks from organisms such as fungi and bacteria and animal pests.

The present invention has the advantage of increasing yields of mature embryos and of providing further maturation to somatic embryos, which in turn improves the vigor of the germinated plantlets. The enhanced maturation and desiccation methods of the present invention also provide increases in the amount of storage reserves of the matured or desiccated somatic embryos. The fact that the water content of the severely desiccated embryos is reduced to a lower level than that of mature dry seeds improves embryo quality and long-term storage. In fact, the water content is sufficiently reduced that the embryos can be stored for extended periods of time in the frozen state without damage due to ice formation.

Furthermore, reductions in water content allow long-term storage of germlines without need for complex cryopreservation equipment, whereby somatic embryogenesis may be recaptured from stored mature somatic embryos. Also, encapsulation of the desiccated embryos of the present invention in a non-hydrated polymer allows for machine handling of the coated embryos as the polymer coating enhances resistance to shock.

One of the important aspects of the present invention resides in the combined use of a non-permeating water stress agent and a plant growth regulator having an influence on embryo development such as ABA and/or analogs, precursors or derivatives thereof during at least a portion of the embryo maturation process to stimulate maturation frequencies and promote further maturation of the embryos, and to increase dry weight and lower moisture content. The following description specifically refers to the use of ABA and analogs, precursors and derivatives thereof as the plant growth regulator of choice to be combined with the non-permeating water stress agent to achieve maturation and mild desiccation of somatic embryos. The terms ABA analogs, ABA precursors and ABA derivatives are intended to designate compounds that mimic the action of ABA in plants without necessarily being structurally related to ABA. Examples of such compounds are found in Dunstan et al. (1991, Plant Science 76, 219–228 and 1992, Phytochemistry 31:1451–1454), the contents of which are hereby incorporated by reference. These compounds include abscisyl alcohol, acetylenic aldehyde and dihydroacetylenic alcohol.

It is to be appreciated that any plant growth regulator specifically associated with inducing stress, and hence having a positive influence on embryo development can be used in the context of the present invention. Examples of alternate stress regulators include compounds such as phaseic acid (PA), dihydrophaseic acid (DPA), 6'-hydroxymethyl abscisic acid (HM-ABA), beta-hydroxy abscisic acid, beta-methylglutaryl abscisic acid, beta-hydroxy-beta-methylglutaryl hydroxy abscisic acid, 4'-desoxy abscisic acid, abscisic acid beta-D-glucose ester and 2-2(2-p-chlorophenyl-trans-ethyl)cyclopropane carboxylic acid.

Also included is jasmonic acid or derivatives thereof. The influence of jasmonic acid and some of its derivatives on plant metabolism has been demonstrated by Reinbothe et al. in (1992) Journal Plant Growth Regulation 11:7–14 and by Parthier et al. in Proceedings of the 14th International Conference on Plant Growth Substances 1991, Kluwer Academic Publishers, pp. 277–286, both references being hereby incorporated by reference. It is also possible to complement the maturation medium by incorporating plant growth promoters having auxin-like and cytokinin-like activity.

When a non-permeating water stress agent is selected, its choice is also important. It is desirable that it contain at least one non-plasmolysing high molecular weight compound such as PEG having a molecular weight range over 1000 (e.g. PEG 4000) or other high molecular weight polymers such as dextran.

The present invention constitutes an unexpected advance in gymnosperm somatic embryo research, especially in conifer somatic embryo research, in view of the currently available technology which fails to teach simple and reliable methods to achieve effective somatic embryo maturation and desiccation. The use of a non-permeating water stress agent in combination with high concentrations of ABA, such as, for example, 12 to 60 $\mu$M, throughout the maturation stage has not only led to substantial increases in maturation frequencies, increased embryo dry weights and lowered moisture contents in gymnosperm somatic embryos and particularly conifer somatic embryos, but has also stimulated desiccation tolerance and enhanced accumulation of storage reserve compounds such as triacylglycerols (TAG) and proteins. In fact, when specifically using high molecular weight compounds as a non-permeating water stress agent, a threefold increase in storage proteins and a ninefold increase in storage lipids was noted for conifer somatic embryo. In contrast, the use of permeating water stress agents has provided substantially smaller increases in storage reserves. Furthermore, permeating water stress agents did not lead to successful desiccation as their use at effective concentrations for prolonged periods was lethal or detrimental to embryo development.

This summary is necessarily abbreviated; the full scope of the invention is as presented in the claims. The present invention will be more completely understood by referring to the following description. For convenience, the present method invention and a companion product invention are described together, and aspects of both or either may be referred to as "the invention".

IN THE DRAWINGS

Figure 4:

FIG. 4 shows the high frequency survival of cotyledonary stage white spruce somatic embryos following 8 weeks on maturation medium containing 16 $\mu$M ABA and 7.5 PEG, then desiccated by treatment in low relative humidity (r.h.).

Figure 5:
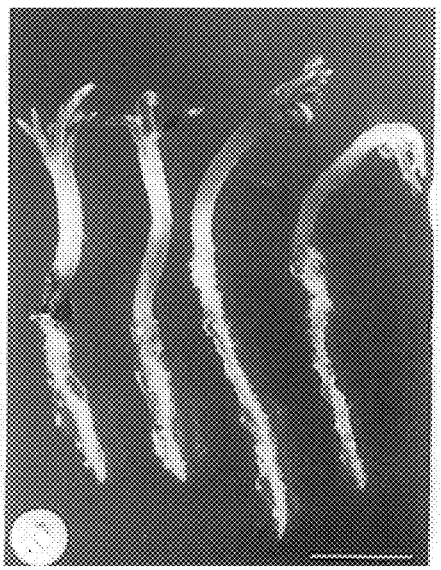

FIG. 5 shows three week old white spruce somatic plantlets regenerated from somatic embryos matured for 8 weeks on maturation medium containing 16 $\mu$M ABA and 7.5% PEG, then desiccated by treatment in low r.h.

Figure 6:

FIG. 6 shows three-week-old white spruce zygotic seedlings.

FIGS. 7–14 show sectioned material of white spruce. All electron micrographs are of cells adjacent to the shoot apical meristem.

Figure 7A:
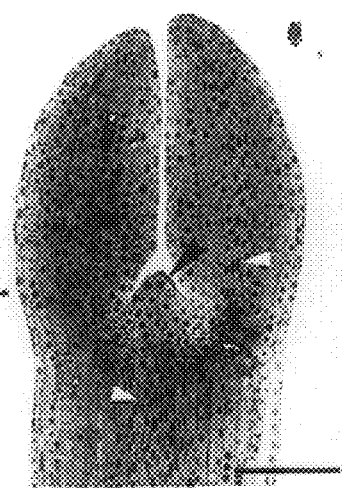

FIG. 7A is a light micrograph showing the shoot apical meristem (black arrow) and procambial cells (white arrows) of a mature zygotic embryo dissected from a seed imbibed for 16 hours.

Figure 7B:
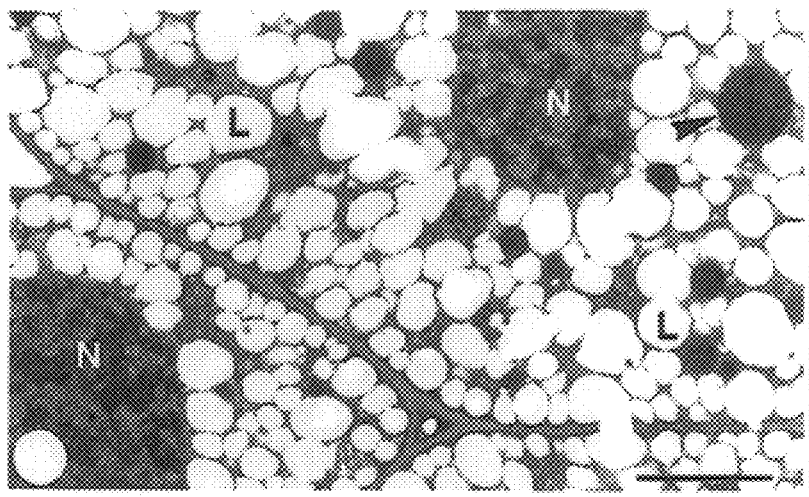

FIG. 7B is an electron micrograph of cells in the zygotic embryo shown in FIG. 7A.

Figure 8:
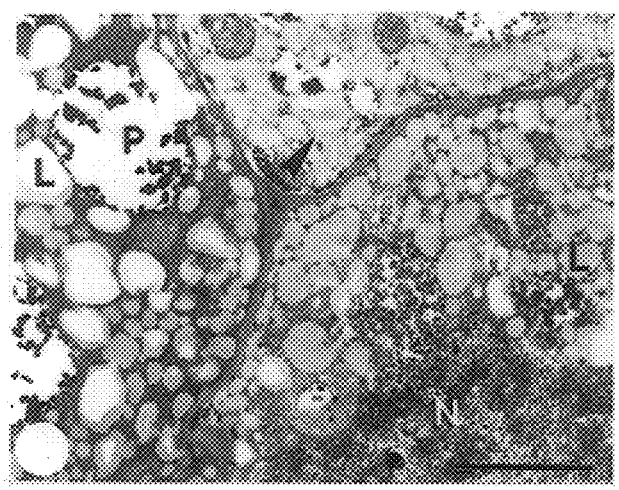

FIG. 8 is an electron micrograph of cells in a zygotic embryo dissected from a seed imbibed for 65 hours.

Figure 9:
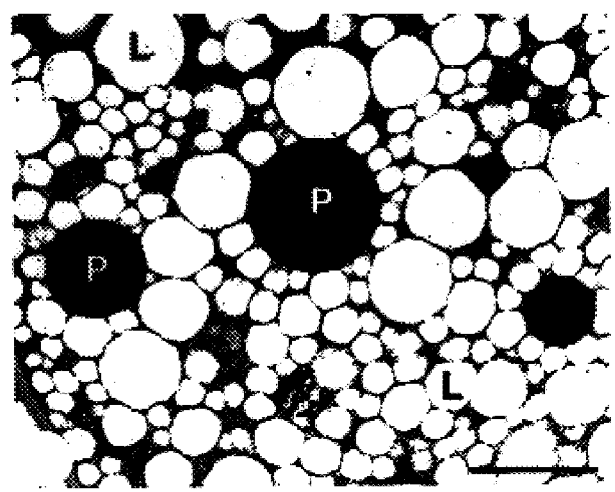

FIG. 9 is an electron micrograph of cells in a non-desiccated somatic embryo immediately following maturation for 8 weeks with 16 $\mu$M ABA and 7.5% PEG.

Figure 10A:
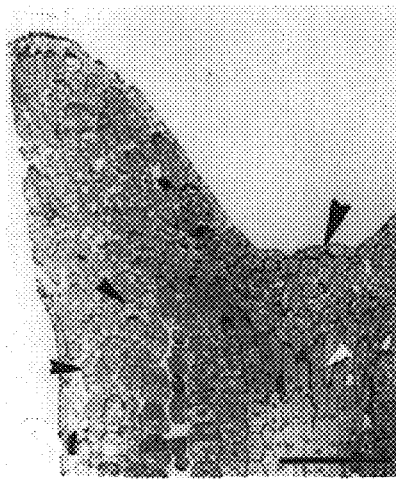

FIG. 10A is a light micrograph showing a median section through the shoot apical meristem of a 2 h imbibed somatic embryo following maturation for 8 weeks with 16 $\mu$M ABA and 7.5% PEG, then desiccation by treatment in low r.h.

Figure 10B:
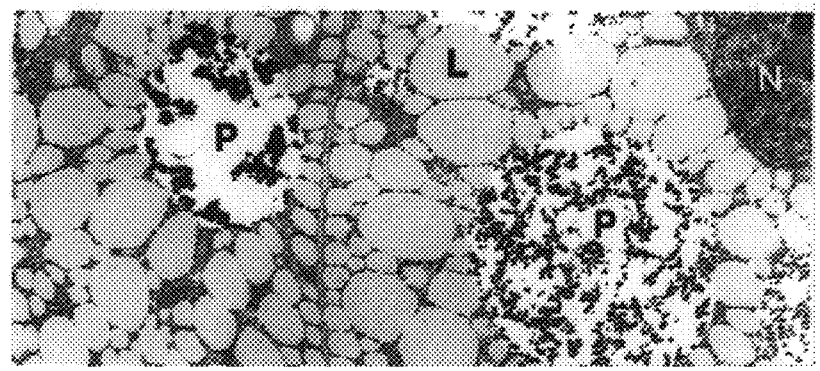

FIG. 10B is an electron micrograph of cells in the somatic embryo of FIG. 10A.

Figure 11A:
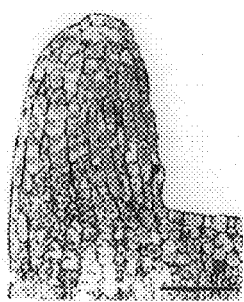

FIG. 11A is a light micrograph showing a median section through a shoot apical meristem of a somatic embryo matured for 4 weeks with 16 $\mu$M ABA but without PEG.

Figure 11B:

FIG. 11B is an electron micrograph of cells in the somatic embryo of FIG. 11A.

Figure 12A:
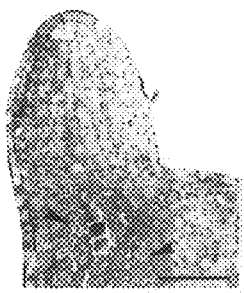

FIG. 12A is a light micrograph showing a median section through a shoot apical meristem of a somatic embryo matured for 4 weeks with 16 $\mu$M ABA and 7.5% PEG.

Figure 12B:
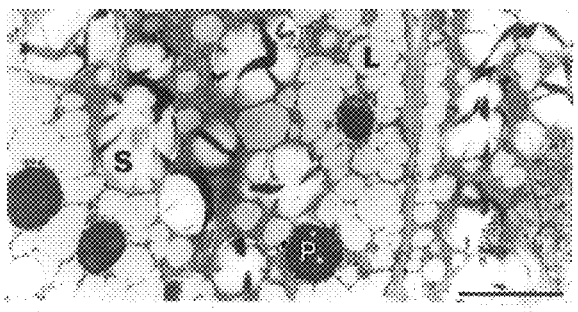

FIG. 12B is an electron micrograph of cells in the somatic embryo of FIG. 12A.

Figure 13A:
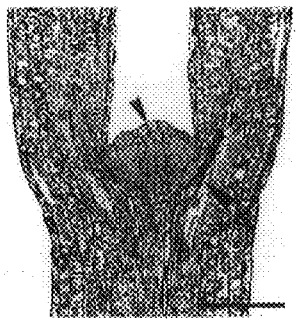

FIG. 13A is a light micrograph showing a median section through the shoot apical meristem of a 4 week old zygotic seedling grown from an isolated embryo.

Figure 13B:
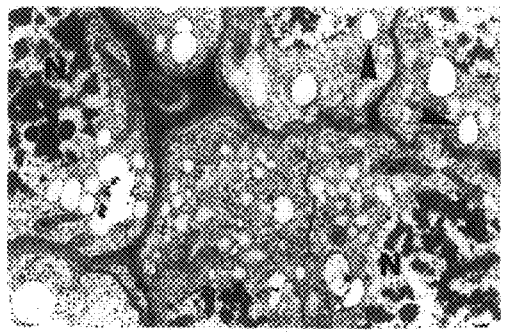

FIG. 13B is an electron micrograph of cells in the zygotic seedling of FIG. 13A.

Figure 14A:
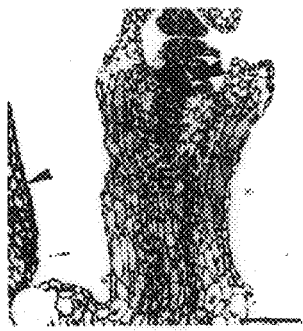

FIG. 14A is a light micrograph showing a median section through the shoot apical meristem (large arrow) of a 4 week old somatic plantlet regenerated from a somatic embryo matured for 8 weeks with 16 $\mu$M ABA and 7.5% PEG, then desiccated.

Figure 14B:
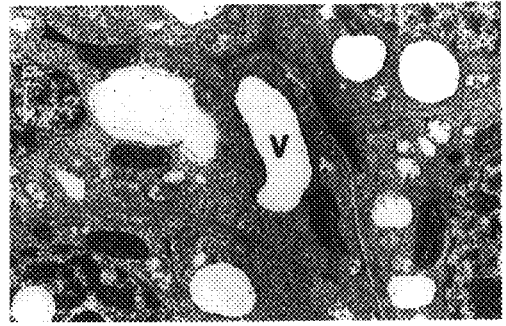

FIG. 14B is an electron micrograph of cells in the somatic plantlet of FIG. 14A.

Figure 15:
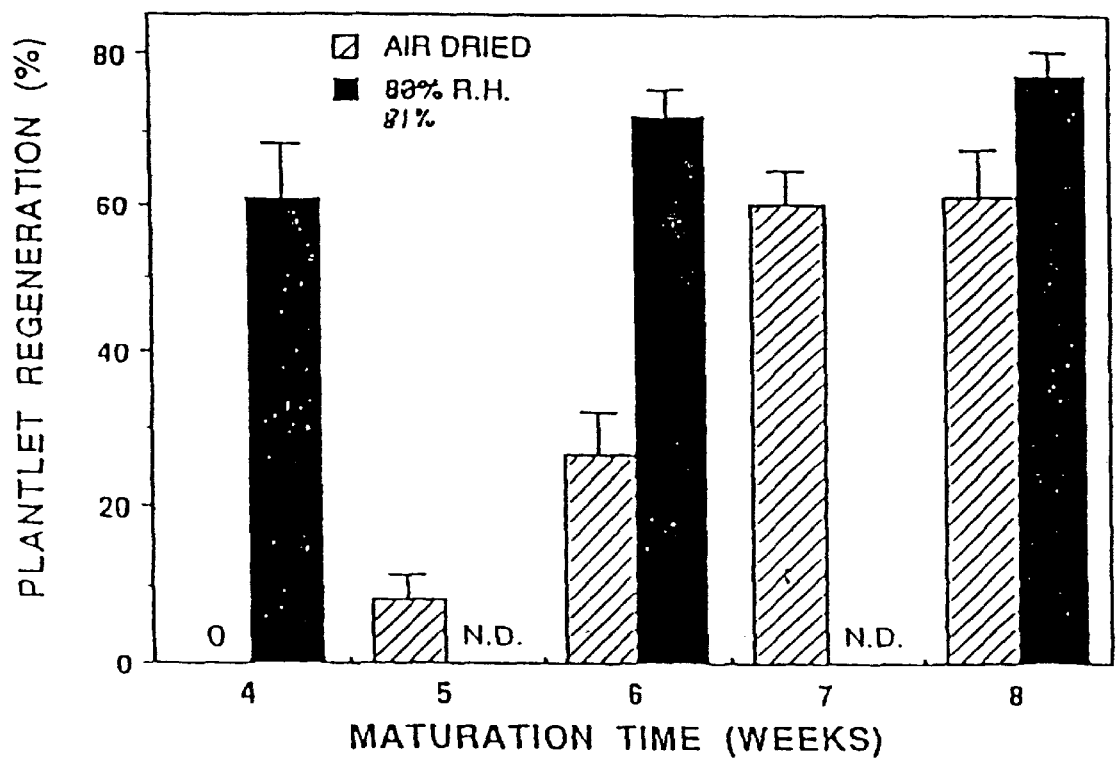

FIG. 15 represents the desiccation tolerance of white spruce somatic embryos as a function of maturation time.

DETAILED DESCRIPTION OF THE INVENTION

The inventions of this application and a companion application relate to desiccated mature gymnosperm somatic embryos and to a method for producing desiccated mature gymnosperm somatic embryos. The preferred method generally comprises developing immature somatic embryos in a medium comprising at least one non-permeating water stress agent, a metabolizable carbon source and a plant growth regulator such as ABA and/or analogs, precursors or derivatives thereof for a period of time sufficient to yield mildly desiccated mature viable somatic embryos tolerant to further desiccation and having a moisture content ranging between 32 and 55%/wt, preferably between 35 and 45%/wt.

If it is desired to obtain further desiccation of the somatic embryos, as for storage, the desiccated mature somatic embryos obtained previously are submitted to continuing desiccation treatment involving further water stress, which can be, for example, either osmotic stress or a controlled environment such as one having a low r.h. for a period of time sufficient to yield severely desiccated somatic embryos having a moisture content ranging between about 10 and about 36%/wt. The resulting desiccated somatic embryos can then optionally be coated in a non-hydrated water-soluble compound and stored either frozen or at room temperature.

There is a striking similarity in design of embryos of all gymnosperm species. Indeed, there is a basal plan of embryo development which is more or less common to all gymnosperms. At first, there is a free nuclear phase of varying derivation. Then there is a wall formation followed by the organization of two tiers of which the upper remains open toward the archegonium. After this usually the cells of the latter divide once more resulting in the upper tier which again remains open and the middle tier which functions as the suspensor. Somatic embryogenesis involves a reactivation of much of the development program of normal embryogeny, and to date, the same range of conditions found to promote induction, proliferation and maturation of white spruce are the same as all other conifers and are distinct from the methods developed for angiosperms. Zygotic embryos of all gymnosperms, the group to which conifers belong, display similarity in their mode of development, which is unique from all other plant groups, particularly the angiosperms. Hence, although the following description refers specifically to methods used to produce desiccated conifer somatic embryos, it is to be understood that these methods have a broader field of application which includes all gymnosperms.

The present invention requires the understanding and control of certain critical factors such as the concentration of ABA and the nature and concentration of the non-permeating water stress agent used in the development of the mildly desiccated mature embryo, the environment and method by which the mildly desiccated mature somatic embryos can be further desiccated and the method by which the desiccated somatic embryos are subsequently encapsulated. Each of these aspects will be discussed separately along with more detailed considerations on the maturation and desiccation methods.

Abscisic Acid

The period during which abscisic acid is supplied in the development stage varies according to plant species. For example, as immature conifer somatic embryos do not develop into functional mature embryos on hormone-free medium, ABA must be supplied at least at the beginning of the maturation period even if the application of ABA can be interrupted for a portion of the development. Preferably, ABA should be initially present in the medium in sufficient concentration so as to have a final concentration of ABA of at least 0.1 $\mu$M at the end of the period during which the embryos are developed. The presence of high levels of ABA throughout most of the maturation period maximizes development while limiting precocious germination. It is generally preferred that a substantially constant ABA concentration be maintained during the majority of the maturation period, but levels may be gradually raised and lowered at the start or end of maturation, particularly if a bioreactor is used as a culture vessel.

Maturation of the somatic embryos can be initiated immediately following transfer from induction or multiplication medium to maturation medium but maturation may be improved if immature embryos are precultured on reduced growth regulator, or growth regulator free multiplication medium, or multiplication medium containing reduced auxin or cytokinin alone. Additional details on preculturing of the embryos is provided further below.

Development of the embryos takes place for a period of time usually ranging from 1 to 15 weeks. Commercial ABA consists of racemic forms but only the (+) form is effective in promoting maturation. The concentrations of (+) ABA that can be used during development, whether for maturation purposes or ultimately for desiccation purposes, range from 0.1 to 100 $\mu$M. Concentrations of ($\pm$) ABA between 12 $\mu$M to 60 $\mu$M are preferred. Optimal results are obtained when maturing conifer somatic embryos for 6 to 8 weeks on a medium containing 16–24 $\mu$M ($\pm$) ABA.

Non-permeating Water Stress Agent

As mentioned previously, two types of osmotic stress can be applied to plant cells. The first type is a permeating osmotic stress usually induced by low molecular weight compounds such as sucrose or mannitol. In this instance the permeating osmotic agent crosses the cell wall and causes water to exit from the symplast (cell cytoplasm) by osmosis. However, the permeating agent is free to enter the symplast of the cell. Over time, sufficient permeating agent may enter to alter the cells osmotic potential which leads to water then reentering the cell by osmosis. Thus, tissue water contents are not necessarily lowered during prolonged incubation with permeating osmotica. Furthermore, the internalized osmotica may directly or indirectly affect cellular metabolism. For example, simple sugars and salts may be absorbed and utilized by the plants cells, resulting in nutritional or osmotic adjustment. Toxic effects on metabolism may also result.

In the case of a non-permeating osmotic stress, compounds such as PEGs or dextrans should have a sufficiently high molecular weight to avoid penetration of the agent through the matrix of the cell wall. Non-permeating osmotica similarly remove water from the cell by osmosis, however, the osmotic agent is not free to enter the cytoplasm. The effects are therefore long lasting and simulates a non-osmotic (e.g., drought) stress at the cellular level. When non-penetrating or less readily penetrating solutes are used, the more negative osmotic potential of the external medium due to these solutes can only be counter-balanced by tissue dehydration, or active uptake of other external solutes and the biosynthesis of organic osmotica. The latter may then be converted to stored product.

As the diameter of pores in the walls of living plant cells through which molecules can freely pass has been determined by a solute exclusion technique to be between 30 and 45 ångstroms, depending on plant species and type of tissue (e.g. root or leaf, etc.), it seems that molecules with diameters larger than these pores would be restricted in their ability to penetrate such a cell wall. It would therefore appear that molecules having a diameter above 30 ångstroms could be used either alone or in combination with other types of osmotica to induce a non-permeating water stress in conifer somatic embryos. Polyethylene glycols having a molecular weight above 1000 and dextrans having a molecular weight above 4000 are preferred non-permeating water stress agents, although it is to be understood that the present invention is not to be restricted to the use of these products. In fact, the class of solutes or compounds that could be used to induce a non-permeating water stress could include any water soluble high molecular weight compound having a molecular size above 30 ångstroms. Suitable alternatives include but are not restricted to: complex carbohydrates such as celluloses, pectins, galactans, polysucrose such as that sold under the trademark Ficoll, polypropylene glycols, agars, gums and oligosaccharides as well as proteins, amino acids (especially polyamino acids), lipoproteins, nucleotides, oligonucleotides and lipopolysaccharides.

The use of non-permeating solutes to cause non-osmotic moisture stress in whole soil grown plants to compensate salt effects or to effect osmotic priming of seeds has been widely documented. High molecular weight compounds have also been suggested as components in hydrated gels to encapsulate previously desiccated meristematic tissue, somatic embryos or tissue cultured plants. However, the specific use of non-permeating solutes such as PEGs or dextrans in combination with ABA for the purpose of reducing moisture contents, enhancing maturation and ultimately permitting severe desiccation of somatic embryos is described for the first time in the context of the present invention.

In the context of the present invention, concentrations of non-permeating compounds ranging between 1 and of 30%/wt have been found useful to promote embryo maturation. The use of polyethylene glycol (PEG) having a molecular weight ranging between 1000 and 35,000, preferably PEG having a molecular weight ranging between 3500 and 10,000 and most preferably PEG 4000 to 8000 in concentrations of 1 to 30%/wt is preferred. Most preferred PEG 4000 and PEG 8000 concentrations are in the range of 2 to 15.0%/wt. A 7.5%/wt concentration of PEG 4000 led to a threefold increase in maturation frequency when compared to controls and was optimal for storage reserve accumulation.

It was observed with PEG that the higher molecular weight varieties needed to be applied in greater amounts to achieve comparable osmotic potentials than lower molecular weight varieties. Thus, very high molecular weight PEGs can occupy a greater proportion of the medium which prevents gelling of the medium. When culturing embryos on agar gelled media, PEG 4000 is preferred for applying a non-permeating water stress while enabling gelling of the medium at appropriate concentrations. A continuous flow bioreactor enables a greater range of high molecular weight compounds to be used.

With regard to dextran, dextran with a molecular weight up to 80,000 has been found suitable with a molecular weight above 6000 being preferred. Dextrans should generally be present in the medium in amounts ranging between 1 and 30%/wt, with 5 to 20%/wt being preferred and 10%/wt being most preferred.

It is required to use a non-permeating compound in such a concentration as to reach the desired osmotic potential in the medium. Generally, the osmotic potential of the medium can vary between −0.3 and −2.0 MPa, with −0.6 to −1.0 MPa being preferred.

Process for the Production of Desiccated Somatic Embryos
Preculturing of Somatic Embryos Pre-culture with multiplication medium containing cytokinin as the sole growth regulator, then transfer to ABA containing maturation medium, promoted maturation of somatic embryos from lines previously found recalcitrant to standard ABA maturation treatments. Similarly, the inclusion of cytokinin with ABA during the first few weeks of maturation, prior to transfer to maturation medium contain ABA alone, prevented precocious germination during the maturation phase. This resulted in improved maturation frequencies, and also led to the recovery of mature embryos from cell lines previously found to be recalcitrant to maturation treatments.

Investigations of white spruce indicate that preculture for one week in plant growth regulator free liquid multiplication medium promoted subsequent maturation frequencies, frequently doubling the recovery of mature embryos. Subsequent embryo development on ABA containing maturation medium was also faster, as early cotyledonary stage embryos were evident up to a week sooner than ABA cultures given no pretreatment. This optimum duration of the pre-culture period seemed to vary with age of the suspension culture. Thus, a newly established suspension culture (<1–3 months) following cryostorage, benefitted from a plant growth regulator free culture of 1–3 days while a one-week pre-culture led to reduced recovery of mature embryos. However, the same cell line recovered from cryostorage 18 months earlier, required a pre-culture of at least 1 week for optimal maturation. The best and most consistent method of pre-culturing was to reduce by at least 1/10 the auxin from the multiplication medium for a 1 week period, prior to plating on medium containing ABA and non permeating osmoticum. An alternative method is to reduce all growth regulator levels without eliminating them entirely. These pre-treatments, plus subsequent ABA/moisture stress had a synergistic effect on somatic embryo maturation frequencies, which were at least doubled compared to no pretreatment.

Thus, even though the pre-culturing of the somatic embryos prior to desiccation remains optional in the process of the present invention, it may, in some instances, be useful to enhance maturation of selected cell lines which are not as responsive as others to direct ABA maturation.

Maturation and Mild Desiccation of Somatic Embryos

Desiccated mature somatic embryos are obtained by developing immature somatic embryos in a medium comprising at least one non-permeating water stress agent, a metabolizable carbon source such as sucrose and ABA and/or analogs, precursors or derivatives thereof for a period ranging from 1 to 15 weeks, with 4 to 10 weeks being preferred and 6 to 8 weeks being most preferred. As mentioned previously, the concentration of (+) or (−) ABA used during the maturation process may range from 0.1 to 100 $\mu$M but (±) ABA should preferably range from 12 to 60 $\mu$M. With regard to the non-permeating water stress agent, PEG 4000 to 8000 is preferred in concentrations of 1 to 30%/wt, with a 1–15%/wt concentration being preferred. It is important to mention that the temperature at which maturation is effected can influence the time required to complete maturation. The process is especially suitable for maturing conifer somatic embryos.

Characteristics of Mildly Desiccated Mature Somatic Embryos

The somatic embryos obtained by the process described above are characterized by having a moisture content ranging between 32 and 55%/wt, preferably between 35 and 45%/wt and a total per embryo lipid content and dry weight which are higher than the per embryo lipid content and dry weight of corresponding zygotic embryos. In fact, the weight of total lipid and triacylglycerols (TAG) per embryo can be up to 5 times higher than in corresponding zygotic embryos.

In the case of mildly desiccated mature conifer somatic embryos, the moisture content usually ranges between 32 and 55%/wt, with a moisture content between 35 and 45%/wt being preferred. With regard to TAG, they can be present in amounts ranging between 70 and 350 $\mu$M, with 70 to 150 $\mu$M being usually obtained.

Dry weights of conifer somatic embryos usually varies between 0.2 and 1.5 mg, with 0.2 to 0.8 mg being usually obtained. Preferred conifer somatic embryos are those from the family Pinaceae.

For example, when comparing white spruce somatic embryos matured with 7.5% PEG and 16 $\mu$M ABA for 4–8 weeks to corresponding zygotic embryos, both have similar TAG fatty acid, and storage polypeptide profiles, similar structure and similar desiccated and imbibed moisture contents. However, somatic embryos after just 4 weeks maturation are larger as demonstrated by their greater dry weights, and by the 6th week of maturation contain considerably more storage reserves such as lipids. Thus, by 6 weeks levels of TAG per embryo have almost doubled compared to zygotic embryos, and by 8 weeks levels have at least tripled, as shown in Table 1 below. Secondary desiccation treatments to achieve lower moisture contents may increase values further.

TABLE 1

| Embryo type | Dry wt mg/embryo | TAG $\mu$g/embryo |
|---|---|---|
| Somatic maturation time (weeks) | | |
| 4 | 0.27 | 36 |
| 6 | 0.4 | 72 |
| 8 | 0.7 | 143 |
| Zygotic | 0.15 | 44 |

Severe Desiccation of Mature Somatic Embryos to Low Moisture Contents

The method for desiccating somatic embryos provided by the present invention is carried out in two major steps. The first step consists in reducing the water content of immature somatic embryos during their development by maturing these embryos in a medium comprising at least one non-permeating water stress agent, a metabolizable carbon source and ABA and/or analogs, precursors or derivatives thereof for a period of time sufficient to yield mildly desiccated mature somatic embryos having a moisture content ranging between 32 and 55%/wt, preferably between 35 and 45%/wt. The second step consists of a late stage desiccation process. The mildly desiccated mature somatic embryos are then submitted to a secondary desiccation treatment which involves either submitting the embryos to further osmotic stress or to at least one environment having a low r.h. to yield severely desiccated somatic embryos having a final moisture content ranging between 10 and 36%/wt, with a 20 to 30%/wt moisture content being the most preferred range.

1° Reduction of the Water Content and Increase of Storage Reserves of Immature Somatic Embryos In order to successfully achieve severe desiccation to low moisture contents of mature somatic embryos and particularly conifer somatic embryos, it is necessary to first reduce the moisture content of the embryos during maturation to a percentage between 32 and 55%/wt, ideally between 35 and 45%/wt. Reducing the water content of the embryos during maturation leads to enhanced tolerance to further severe desiccation for the following reasons. Tolerance to desiccation to low moisture contents appears to be closely related to the level of storage reserves. Treatments that promote storage reserve accumulation, such as ABA, non-plasmolysing moisture stress, and increased maturation time, also promote desiccation tolerance. This is because vacuolate cells containing little reserve material may undergo mechanical disruption and tearing of membranes during severe water loss, while the presence of sufficient reserves limits such changes. Additionally precocious germination is inhibited which further enhances severe desiccation tolerance.

Treatment of the embryos with a non-permeating water stress agent improves the maturation frequencies of the embryos. The promotive effect is considered to be a consequence of the induced non-plasmolysing water stress. As will be demonstrated later, non-permeating water stress agents such as high molecular weight PEGs and dextrans, when used in appropriate concentrations, that is generally in concentrations of 1 to 30%/wt, stimulate substantial increases in maturation frequency when compared to controls. In fact, in one of the preferred features of the present invention, 5 to 7.5% PEG 4000 or 10% dextran 80,000 stimulated a threefold increase in maturation frequency of conifer somatic embryos compared with controls.

The moisture content of mature severely desiccated somatic embryos treated by the process of the present invention is similar to that of mature zygotic embryos. However, regenerated plantlets from non-permeating water stress treated then severely desiccated somatic embryos are of better quality than the non-osmotically treated controls. A possible reason for this is that somatic embryos, matured in the absence of water stress agents, germinate precociously in the first few days of secondary stage desiccation, while moisture contents are still high. It is probable that in these instances subsequent survival of tissues such as root and/or shoot meristems, hypocotyl and cotyledons in somatic embryos was non-uniform, leading to irregular plantlets.

By comparison, somatic embryos matured in the presence of non-permeating water stress agents had a lower moisture content and were therefore already considerably 'drier' prior to further severe desiccation. These embryos remain quiescent following transfer from the ABA medium, and desiccation of each embryo is more uniform, thereby improving plantlet quality. However, somatic embryos remain quiescent under low osmotic conditions only when ABA is present. Thus, for conifer somatic embryos, a combination of both ABA and non-permeating water stress agent is more effective in promoting maturation and preventing precocious germination than when ABA and the non-permeating water stress agent are taken individually. There seems to be a synergistic effect occurring when ABA and PEG are used concurrently.

During prolonged maturation (e.g. 8 weeks maturation) the non-permeating water stress becomes increasingly important in preventing precocious germination, which improves survival following further desiccation. Precocious germination is especially evident for treatments with low ABA concentration, and low water stress, and during secondary desiccation treatments, leading to limited or no survival for all of these treatments. After 8 weeks maturation, the increased tendency for precocious germination during prolonged maturation treatments may be because somatic embryos undergo a reduction in ABA sensitivity during maturation. It was also observed that a reduction in tolerance to rapid severe desiccation (e.g. on the lab bench) occurs late in maturation (i.e. 8 weeks maturation) which corresponds with the time at which somatic embryos display a greater tendency for precocious germination.

Both ABA and osmoticum promote the accumulation of storage reserves in embryos. The trend of increasing dry weight and decreasing moisture content of osmotically treated white spruce somatic embryos indicates that storage reserves are deposited within cells while water is displaced. As mentioned previously, the osmotically treated somatic embryos accumulate more storage reserves (e.g. proteins and lipids) when compared to the untreated controls.

Embryos of many plant species germinate normally only if desiccated first, suggesting activation of new genes. In the case of conifer somatic embryos, it has been shown that further severe desiccation of somatic embryos is necessary to promote subsequent plantlet development only when the somatic embryos are matured using elevated osmotic concentrations. Embryos matured under low osmotic conditions subsequently develop without the need for further desiccation, but show a tendency towards precocious germination.

The effect of PEG concentration on osmotic potential is different from that of solutions of permeating water stress agents such as salts and sugars. For instance, a negatively curvilinear decrease in osmotic potential occurs with increasing PEG concentration and is apparently related to structural changes in the PEG polymer. The application of sucrose at similar osmotic potentials to 5.0–7.5% PEG 4000 does not readily promote the maturation of conifer somatic embryos, possibly because absorption of this solute by the tissues leads to an altered metabolism.

Thus, the application of a non-permeating water stress agent to the maturation medium leads to somatic embryos that resemble zygotic counterparts, in terms of low moisture content, and high degree of quiescence. In addition, the non-permeating water stress agent stimulates maturation frequencies, and improves storage product accumulation.

In order to maximize water loss (mild desiccation) and maturation during the development stage of the somatic embryos, various experiments have been set up to observe the effects of different culture conditions on maturation and water loss. It seems that the embryo should be maintained for a minimal period of 1 week and a maximal period of 15 weeks, preferably for 4 to 8 weeks and most preferably for 6 to 8 weeks on a medium containing preferably between 12 and 60 $\mu$M ABA and preferably between 1 and 30%/wt of non-permeating water stress agent. The concentration of the non-permeating water stress agent may vary depending upon its nature.

For example, in the case of PEG, having an average molecular weight of 4000, concentrations of 7.5% with an osmotic potential of −0.7 MPa were determined to be optimal for maturation on agar gelled medium. Once the desired water content has been achieved through maturation of the somatic embryos, severe desiccation is effected to further reduce moisture levels, thereby enhancing long term storage, enhancing resistance of the embryos to frost damages and improving subsequent plantlet vigor.

Maturation of Somatic Embryos Using a Continuous-flow, Solid-support Bioreactor

Experiments to date usually involve maturation of somatic embryos on semi-solidified medium, or on supports over liquid media, within petri dishes. This is labor-intensive for large scale propagation, particularly when frequent media changes are required. Recovery of mature embryos directly from submerged liquid suspensions permits easier handling of large quantities of material; however, to date, there have been no reports of successful maturation in submerged culture. It seems that in all reports where embryos are submerged in liquid or agar, or merely enclosed within surrounding embryogenic tissues, maturation is inhibited. Conifer somatic embryos have been cultured in liquid suspensions during initial maturation stages, but they then required transfer onto solid supports over media to complete the maturation process. Thus, it is likely that good gas transfer to and from the developing embryos, in addition to a moisture stressing environment, is important. These parameters are, however, difficult to achieve in a liquid environment. An alternative method for yielding large numbers of mature conifer embryos requiring minimal handling, is the use of continuous-flow solid-support bioreactors. Such a system was described in JP 87123756, hereby incorporated by reference. The bioreactor comprises a culture chamber having medium inlet and outlet means for continuous supply of fresh medium in the culture chamber. It also comprises a support for maintaining the immature embryos above the surface of the medium and means for providing and controlling air flow in the chamber. Thus, conifer somatic embryos may be matured within a large chamber supported above liquid medium. Fresh liquid culture medium is pumped into one end of the vessel, while spent medium exits from the opposite end. Also, growth regulator and osmotic changes can be applied gradually as the liquid medium is added, and the air space in the chamber may also be controlled to provide the optimal gaseous environment. The large culture chamber enables large numbers of somatic embryos to be cultured per run, which reduces the costs of using petri dishes.

2° Secondary Desiccation Treatment of Mature Somatic Embryos to Low Moisture Contents It was initially believed that the desiccation tolerance of somatic embryos to severe desiccation to low moisture content, particularly conifer somatic embryos, was influenced by the rate of desiccation. Hence, it was thought that slow desiccation rates increased survival under all osmotic treatments, especially for incompletely matured embryos. However, it has been demonstrated that optimally matured conifer embryos obtained according to the method of the present invention can be desiccated further either using rapid or slow drying. Other desiccation methods using controlled humidity cabinets providing air circulation can also be employed and when doing so, the treatment times outlined below may vary. Severe desiccation can also be achieved by prolonging exposure of the embryos to high concentrations of osmoticum. When used herein, the term "low moisture content" is intended to designate somatic embryos having a moisture content ranging between 10 and 36% following maturation and subsequent desiccation.

a) Gradual Secondary Desiccation Treatment

Embryos are matured on filter paper supports. Gradual desiccation of the embryos to low moisture contents may be accomplished by transferring mature somatic embryos on their filter paper supports through a series of environments of progressively lower r.h. This technique is described by Senaratna et al. in 1989, Plant Science 65, 253–259 which is hereby incorporated by reference. It was initially believed that a gradual water loss allowed sufficient time for the protective changes to occur in cells and hence increased the embryos' resistance to severe dehydration. Further investigations have shown that gradual desiccation is not an absolute requirement even though the technique can be successfully used.

The rate at which gradual desiccation is to be conducted may vary substantially. For example, embryos on moist filter paper supports placed in 81% r.h. chambers usually cause an initial increase in r.h. The r.h. then declines over the next few days to the desired value, thereby producing a very gradual desiccation. If desiccation at a lower r.h. is desired, the rate at which cultures should be transferred to successively lower relative humidity environments may vary substantially, but generally speaking, the matured embryos should be transferred successively to lower r.h. desiccators at 1 to 7 day intervals. The time left at the final required humidity depends on the rate at which the embryos were previously transferred to the lower r.h. Hence, the cultures can be maintained for a minimum of 1 to 7 days at the final required r.h. It is to be noted that r.h. can range between 30 and 95% at a temperature ranging from 20 to 30° C. Total secondary desiccation treatment times can range between 7 and 21 days.

The r.h. can be visually checked within the desiccation chambers by meter. Following stabilization of the meter, a period of 1 to 7 days is allowed at the desired r.h. A visual inspection of the embryos can readily confirm that they are desiccated to low moisture contents as they change from swollen embryos of a pale cream colour, to a shrunken and distorted outline and a yellowish, waxy translucent appearance.

b) Rapid Secondary Desiccation

Experiments have demonstrated that conifer somatic embryos survive slow secondary desiccation at high frequency, preferably when retained with the callus upon the filter paper support. Those removed from the callus and placed horizontally upon the support led to recovered plantlets that were abnormal (the embryos did not elongate normally, but remained stunted). It seems that during slow secondary desiccation treatment, conifer somatic embryos need to be retained within the whole callus in order to subsequently develop normally. Somatic embryos can also survive rapid secondary desiccation which may, in some instances, be more practical than gradual secondary desiccation.

In the case of rapid secondary drying, the technique involves an ambient r.h. ranging between 5 and 95%. An ambient r.h. ranging between 20 and 63% at an ambient temperature ranging between 20 and 25° C. is preferred. An ambient r.h. ranging between 30 and 40%, at a temperature of 25° C. has been found to be suitable. Matured somatic embryos from mild desiccation treatments retained upon filter paper supports and submitted to rapid secondary drying usually desiccate to low water contents within a period of time ranging from 24 to 48 hours but should be maintained at ambient r.h. for a period of at least 3 days, which can extend to 1 week or more if prolonged storage is desired. The tendency seems to be that somatic embryos must be matured in mild desiccation treatment for at least 6 to 8 weeks in order to survive rapid secondary drying. This will be demonstrated in further detail later on.

Characteristics of Low Moisture Content Severely Desiccated Somatic Embryos

First, severely desiccated somatic embryos exhibit a moisture content that is lower than the moisture content of corresponding zygotic embryos from dried seed. Hence, the moisture content of desiccated somatic embryos obtained according to the present invention usually ranges between 10 and 36%/wt %. In fact, the important moisture content that removes all free water is that which permits freezing without injury, that is preferably below about 36%. The level of desiccation achieved depends on the method of secondary desiccation used. Bench dried embryos may have much lower moisture, preferably between 10 and 30/wt %, depending on ambient r.h. and temperature. Furthermore, the dry weight of conifer somatic embryos following secondary desiccation is usually 30 to 600% higher than the weight of corresponding zygotic embryos. Also, the amount of storage lipids found in severely desiccated somatic embryos is 50 to 700% higher than that of corresponding zygotic embryos while demonstrating fatty acids and polypeptide storage reserves which are similar to those of corresponding zygotic embryos. Also, the secondary desiccated somatic embryos have large protein bodies as well as abundant lipid bodies.

Freezing Tolerance of Severely Desiccated Embryos

An analogy exists between tolerance to desiccation and tolerance to freezing. Tissues able to survive freezing in liquid nitrogen are considered to be capable of survival following storage for indefinite periods. For example, somatic embryos matured for 8 weeks with 7.5% PEG and 16 $\mu$M ABA were placed in 81% or 63% r.h. environments to achieve severe desiccation. Somatic embryos from the 63% environment were first given 1 week at 81%. Total secondary desiccation treatment times were 2–3 weeks. Following these treatments, somatic embryos on their filter paper supports were imbibed with ½ strength culture medium, stored overnight in a −20° C. freezer, or plunged into liquid nitrogen then removed and immediately transferred to the freezer overnight. Frozen embryos were imbibed the next day.

Survival frequencies have been used to determine the effectiveness of some of the treatments referred to in the present application. Hence, the term survival, when used herein, is defined as: embryos that became green or commenced elongation within the first week of culture. Embryos matured for 8 weeks survived severe desiccation in the 81% and 63% environments at similar high frequencies (e.g. 70–100%). Embryos also survived freezing at −20° C., but frequencies were better for embryos desiccated in the 63% r.h. environment (96%) compared to 44% for embryos desiccated only in the 81% r.h. environment. Embryos frozen in liquid nitrogen survived at slightly lower frequencies, as about 1–4% of the embryos split or shattered during the rapid freezing process. This problem may be overcome by transferring embryos to liquid nitrogen after initially freezing them to −20° C. Normal plantlets were recovered following all freezing methods.

Characteristics of Imbibed Somatic Embryos

Imbibed somatic embryos have a moisture content usually ranging between 59 and 65%.

Encapsulation of Desiccated Somatic Embryos in a Non-hydrated Colder

One of the novel elements of the present invention resides in the fact that PEG is not to be used as a hydrated gel for encapsulation, but is to be molten and used to encapsulate mature somatic embryos, zygotic embryos or desiccated somatic or zygotic embryos without causing re-hydration. Mature conifer somatic embryos, conifer zygotic embryos as well as desiccated somatic or zygotic embryos, preferably from the family Pinaceae and most preferably from the genus Picea can be encapsulated using the method of the present invention. Other compounds having properties similar to PEG can be used. It is required that the compound used for encapsulation be a non-hydrated water soluble compound having a melting point ranging between 20 and 70° C., although polymers such as PEG are preferred.

PEG is a water-soluble wax-like polymer which is non-toxic, poorly metabolized and highly resistant to attack by organisms (e.g. fungi, bacteria, animal pests, etc.). It is currently used to promote seedling vigor by osmotic priming of seeds, so should be ideal as an encapsulation agent.

Before testing PEG as a suitable agent for encapsulation, the effect of high concentrations of PEG on embryo germination was first tested. This was done using the technique of osmotic priming. Osmotic priming is a method of controlled hydration in which the physiological process of germination is initiated but stopped before radicle emergence. Natural seeds lose vigor during storage, and cell deaths may occur as a result of rapid water uptake during the first minutes of imbibition. PEG and other osmotica have been used to osmotically prime whole seeds to synchronize germination and improve seedling vigor. The method involves soaking seeds in osmotic solutions of sufficient osmotic strength to allow seeds to take up water and metabolism to be restored, but germination is prevented. Imbibition injury may be reduced or prevented, and any cellular damage repaired. Thus, full vigor is restored upon removal of osmoticum (Powell and Mathews 1978; Bodsworth and Bewley 1979; Woodstock and Tao 1981).

A study of sectioned white spruce somatic and zygotic embryos using transmission electron microscopy showed that desiccated zygotic embryos take up to several days to fully imbibe, as they are enclosed within seed coats and other structures. Imbibition of somatic embryos desiccated to low moisture contents, by contrast, occurs within 1–2 h. Such rapid imbibition may lead to injury. Severely desiccated somatic embryos were osmotically primed by imbibing them in liquid medium containing 30% PEG for 3 days prior to transfer to PEG-free medium. Survival frequencies were similar to non-primed treatments, showing the absence of toxicity of high PEG levels on germination; furthermore, root elongation of the PEG treated embryos appeared to be improved.

PEG of different molecular ranges vary in melting point. Highest is only about 66° C. PEG was considered suitable as an encapsulation agent as it could be molten and applied to desiccated embryos without causing embryo re-hydration. PEG of different molecular weights were used singly or mixed to achieve desired properties, or different types applied in different layers (e.g. an embryo coated in a soft wax surrounded by a hard wax layer).

TABLE 2

| PEG mol wt | melt pt | wax type | viscosity |
|---|---|---|---|
| <1000 | <23° C. | soft or liquid | very low |
| =1000 | =37° C. | soft | low |
| =4000 | =59° C. | hard | medium |
| >6000 | 60–66° C. | very hard | high |

Therefore, PEG with molecular weights over 1000 and preferably between 1000 and 3000 may be used. Embryos desiccated to low moisture contents are considered to be tolerant to temperature extremes so should not be harmed by brief exposure to molten PEG; however, the PEG types with lower temperature melting points may be preferable, and are less viscous so flow and coat embryos more readily. PEG 1000–4000 and mixtures thereof are ideal. PEG 1000 is soft and pliable. PEG 4000 is harder and more brittle. Embryos encapsulated in PEG should also be protected from imbibition injury similar to osmotic priming. Thus, as the PEG capsule dissolves into solution around the embryo it creates an osmotic pressure. This pressure would approach zero as the PEG becomes fully dispersed, and would have the effect of preventing the more rapid imbibition, that would otherwise occur in the absence of PEG encapsulation. Capsules take up to 8 hours to dissolve when placed on agar gelled medium.

Various adjuvants may be added to the PEG to assist in seedling establishment. Such adjuvants may include a carbon source such as sucrose or glucose, etc., (myo-inositol was found to be least resistant to caramelizing during prolonged heating with higher melting point PEG), activated charcoal, Psilium seed powder to bind water after re-hydration, fungicides and insecticides added in powder form, microorganisms, organic energy reserves and enzymes such as starch and α-amylase (capsules may be surrounded by other polymers, such as gelatin, or mixed with insoluble waxes, both of which would perhaps give a slow timed release of embryos from the capsules), amino acids (e.g., glycine), plant growth regulators. An example of the encapsulation method of the present invention is outlined below.

Moulds were prepared by drilling shallow wells into a 4 mm thick sheet of silicone rubber (other types of mould may be suitable). Prior to use for encapsulation, the rubber mould was sterilized with alcohol, then evaporated dry.

PEG 6000, 4000, and 1000 and an equal mixture of 4000:1000 have been tested, PEG 1000 being preferred. PEG was heated to above melting point. The molten PEG was heat sterilized by maintaining it at its boiling point, or just below, for at least ½ h. PEG should be cooled to just above its melting point prior to embryo encapsulation. One of the key elements of the encapsulation method is to assure that the embryos are encapsulated with the non-hydrated water soluble compound at a temperature slightly above the melting point of the non-hydrated water soluble compound so as to provide rapid solidifying of the coating to yield hardened capsules containing the embryos.

A small drop of PEG was first added to the wells of the mould. Somatic embryos, desiccated slowly to low moisture content at a r.h. of 63%, were removed from the filter paper supports and placed singly in the wells, and a drop of molten PEG added to enclose the embryo. The volume of the synthetic seeds was approximately 30 μl. After the PEG had solidified the encapsulated desiccated embryos were removed from the mould and stored at room temperature, or in the freezer. For germination, the synthetic seeds were placed on filter papers placed on solidified plantlet regeneration medium. Survival following encapsulation is 93%. After one week in the freezer, the same batch had survived at frequency 83%. Normal plantlets have been recovered. Recovery of plantlets after planting the capsules directly in soil has not yet been tested.

Description of Preferred Embodiments

Study of the Effects of a Non-plasmolysing Induced Moisture Stress on the Maturation and Desiccation Survival of White Spruce Somatic Embryos and Determination of Lipid Composition of Matured and Desiccated Embryos A. Maturation and Desiccation Source of Material and Culture Media The white spruce (line WS1) liquid culture was initiated and maintained on basal medium (BM) as reported previously (Attree, Dunstan and Fowke, 1989; Attree et al., 1990).

The BM used for maintenance was that of von Arnold and Eriksson (1981), and also contained 1% sucrose, 9 $\mu$M 2,4-dichlorophenoxyacetic acid (2,4-D) and 4.5 $\mu$M benzyladenine (BA). The maturation medium consisted of half-strength BM containing 90 mM sucrose and 16 $\mu$M ($\pm$) ABA (Sigma, product number A 2784) solidified with 0.8% agar (Difco Bitek). A stock solution of ABA was filter sterilized and added to cooled medium after autoclaving. The plantlet regeneration medium consisted of half-strength BM with 60 mM sucrose 0.6% agar and lacked plant growth regulators (PGRs). All of the above media were adjusted to pH 5.7. Plastic petri dishes (10 cm) containing 15–20 ml medium were used. Dishes were sealed with Parafilm (American Can Co.) and cultures were incubated at 25° C. Osmotic potentials of media were determined using a vapour pressure psychrometer (model no. 5130, Wescor Inc., Logan, Utah) due to its greater accuracy with PEG solutions (Michel and Kaufmann, 1973).

Somatic Embryo Maturation and Mild Desiccation

Maturation of somatic embryos was carried out using methods modified from Attree et al. (1990). Suspension cultured somatic embryos were washed and resuspended (20% w/v) in half-strength PGR-free BM containing 3% sucrose, to remove the previous PGRs, then 0.75 ml aliquots were pipetted onto filter paper supports (Whatman no. 2) on the surface of maturation medium. The supports facilitated subsequent transfers to fresh media. To determine the mean number of somatic embryos plated, 10 $\mu$l samples of the 20% suspension were stained with acetocarmine (B.D.H.) and counted (repeated 15 times). The plated somatic embryos were maintained on the maturation medium for 4 weeks in the dark. To test the effect of increased osmoticum, the following concentrations of PEG-4000 (Fluka AG) were included in the maturation medium; 0, 2.5, 5.0, 7.5 and 10% (w/v) (25 replicates per treatment). Maturation frequencies per treatment were calculated as the percent mean number of somatic embryos that matured to normal-looking cotyledonary embryos. Maturation frequency results are shown in FIG. 1 ($\pm$confidence limits, P=0.05)

Figure 1:
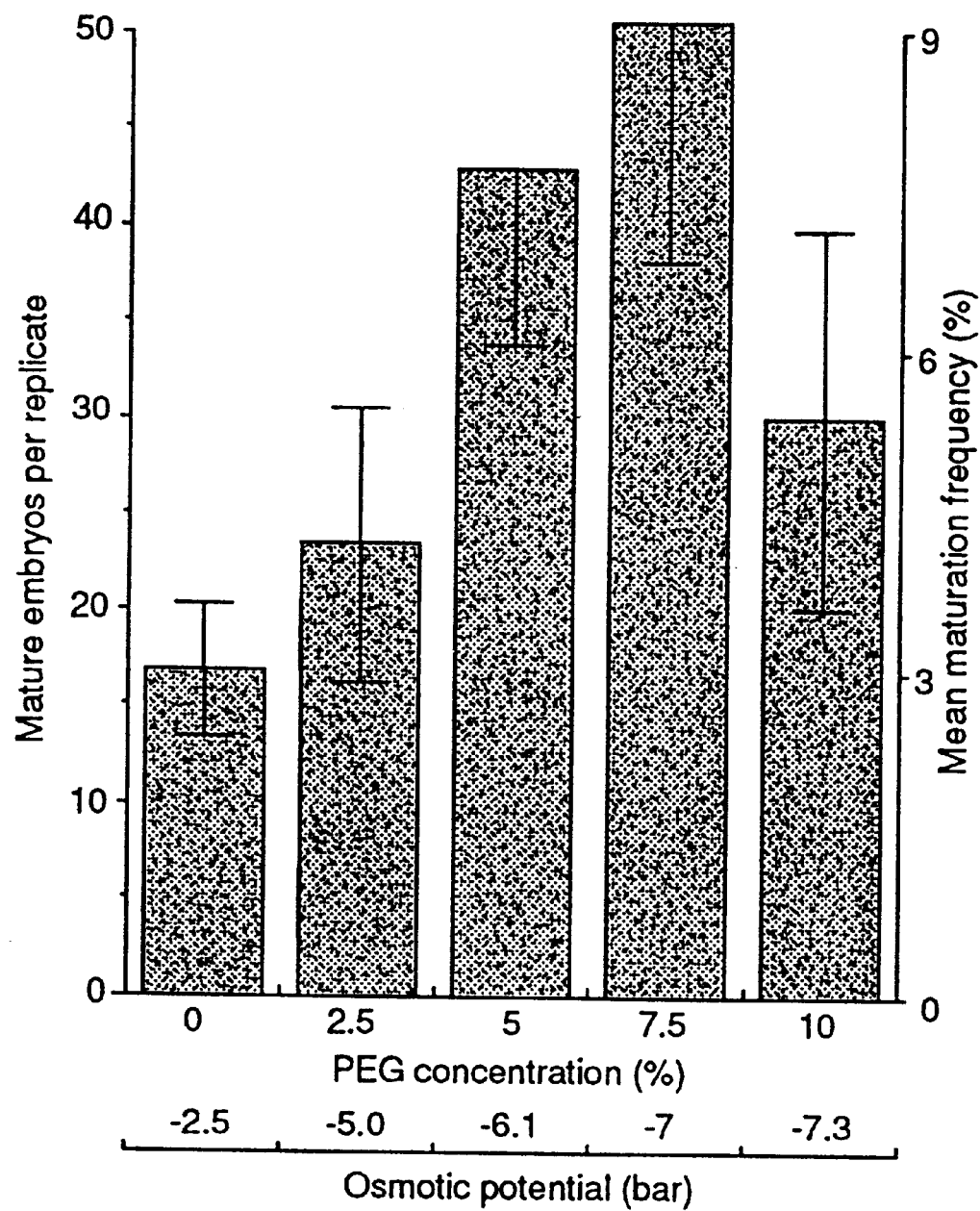
FIG. 1 represents the influence of PEG concentration and osmotic potential on the number of mature white spruce somatic embryos recovered per replicate and on the percentage of maturation frequency.

The application of PEG-4000 in the presence of 16 $\mu$M ABA for 28 d promoted the maturation of white spruce somatic embryos (FIG. 1). The mean number of immature somatic embryos plated per replicate was 560, and maturation results are based upon a total of 4087 mature embryos recovered. The optimal PEG concentration was within the range of 5.0–7.5l. PEG at 7.5% led to a threefold increase in the maturation frequency, compared to the control, giving an overall mean maturation frequency of 9%. In addition, maturation in the presence of 5% PEG or greater led to the absence of sustained embryogenic callus proliferation, which occurred in the 0 and 2.5% PEG treatments despite the presence of ABA.

In preliminary experiments sucrose was tested at 6 and 9%. Visual comparisons showed that 6% sucrose yielded lower maturation frequencies than at sucrose alone, while 9% sucrose led to no growth; therefore, elevated sucrose was not tested further. The osmotic potential of the PEG media decreased non-linearly, falling less sharply at the higher concentrations tested (FIG. 1). The osmotic potential of the 7.5% PEG maturation medium (which also contained media salts and 3% sucrose) was –0.7 MPa; equivalent to the osmotic potential of maturation medium containing 9% sucrose. The osmotic potential of –0.61 MPa for maturation medium containing 5% PEG was approximately equivalent to that containing 7% sucrose.

Determination of Moisture Content and Dry Weight of Mildly Desiccated Mature Somatic Embryos Somatic embryos from various PEG treatments were weighed (hydrated weight), dried in an oven at 60° C. for 3–4 d then their dry weights recorded. The dry weights were used to determine the moisture contents of the mildly desiccated somatic embryos. Measurements were repeated 6 to 12 times depending on the availability of somatic embryos, and 20 somatic embryos were used per replicate. Zygotic embryos were also dissected from unimbibed mature seed, weighed, imbibed in distilled water, then weighed again (repeated three times with 40 embryos per replicate). The hydrated (somatic) unimbibed (zygotic) and dry weights were used to determine the moisture contents of the zygotic and somatic embryos.

Figure 2A:
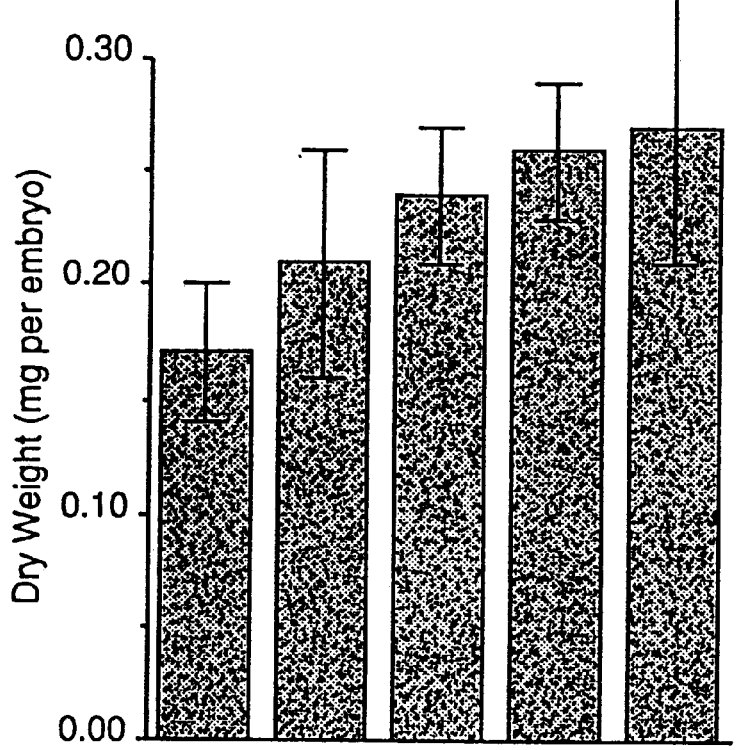
FIG. 2A represents the dry weight of white spruce somatic embryos directly following maturation in the presence of different PEG concentrations (all with 16 $\mu$M ABA).
Figure 2B:
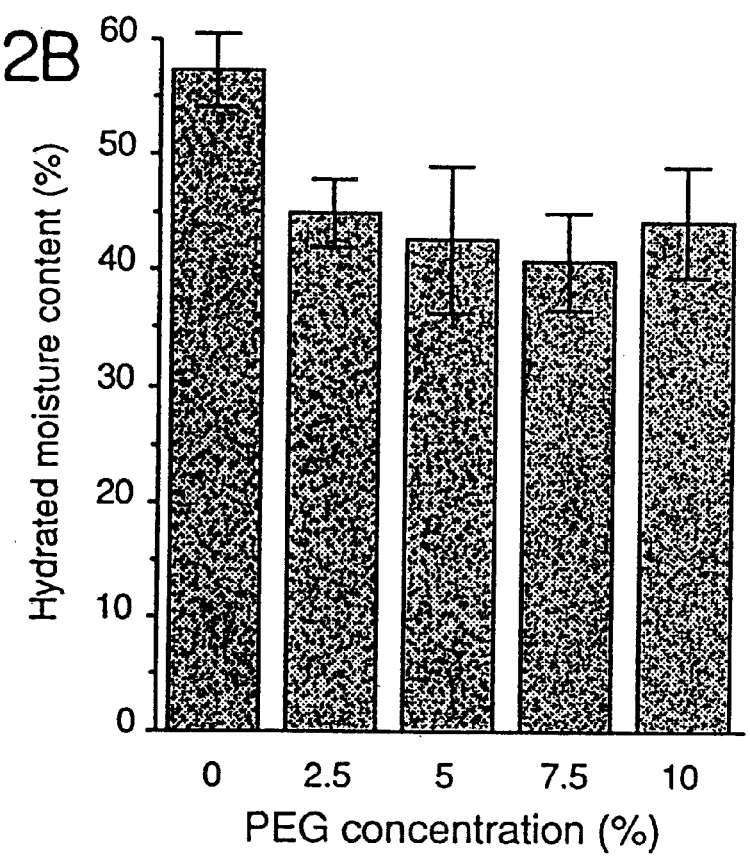
FIG. 2B represents the moisture content of white spruce somatic embryos directly following maturation in the presence of different PEG concentrations (all with 16 $\mu$M ABA).
Figure 3A:
FIG. 3A shows shrunken dry somatic embryos immediately following desiccation for 14 d in an environment of 81% relative humidity.
Figure 3B:
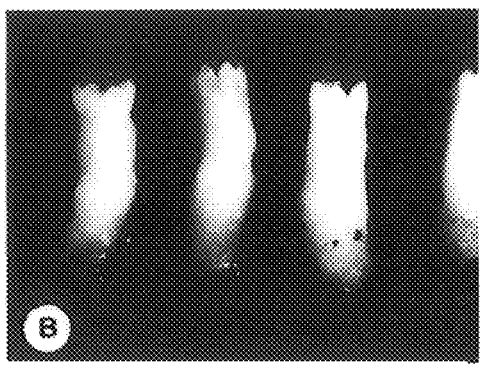
FIG. 3B shows the somatic embryo photographed after 2 hours of imbibition.
Figure 3C:
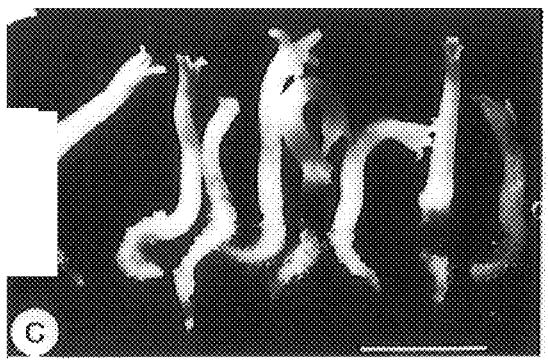
FIG. 3C shows regenerating plantlets 7 d after rehydration following desiccation in an environment of 81% relative humidity.
Figure 3D:
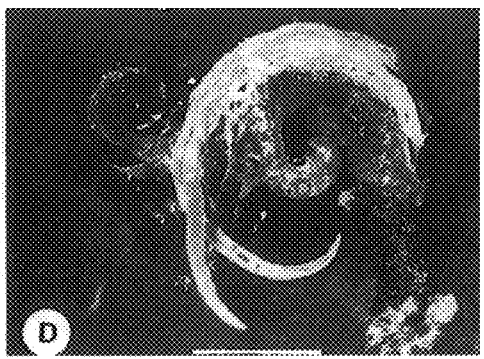
FIG. 3D shows an aberrant typical plantlet matured in the presence of polyethylene glycol (PEG), then germinated for 28 days without a prior desiccation treatment.

As it can be seen in FIG. 2, the dry weights of mature, mildly desiccated somatic embryos increased with increasing PEG concentration, while moisture contents decreased ($\pm$confidence limits, P=0.05). Dry weights of PEG treated somatic embryos increased from 0.17 to 0.27 mg per embryo. Zygotic embryos possessed dry weights of 0.15$\pm$0.01 mg per embryo. Hydrated somatic embryos matured with PEG had mean moisture contents prior to further desiccation of 41–45%. The controls by comparison, possessed mean moisture contents of 57%.

Post-maturation, Secondary Desiccation to Low Moisture Content, and Plantlet Regeneration To determine the effects of PEG, ABA, and secondary desiccation to low moisture content on somatic embryo survival and plantlet regeneration, i.e. desiccation tolerance, somatic embryos matured with or without 7.5% PEG were treated as follows (repeated five times per treatment): directly germinated; given a post-maturation treatment (no ABA, see below) and then germinated; given a post-maturation treatment, secondary desiccated at 81% r.h. (see below), then germinated; or secondary desiccated directly (i.e. no post-maturation) then germinated (see Table 3).

Post-maturation

Post-maturation was achieved by transferring whole somatic embryo cultures, by their filter-paper supports, onto plantlet regeneration medium (which contains no ABA) for 14 d in the dark, as described previously (Attree et al., 1990). Post-maturation of cultures matured with PEG was carried out using plantlet regeneration medium containing the same PEG concentration as that for maturation.

Slow Secondary Desiccation

The effect of PEG on desiccation tolerance was tested by subjecting 4-week matured somatic embryos from all PEG concentrations to the 81, 63, and 43% r.h. environments (repeated 7 to 15 times per treatment).

Secondary desiccation to different degrees of moisture content was accomplished by transferring matured somatic embryos through a series of environments of progressively lower r.h. as described by Senaratna et al. (1989). The following saturated salt solutions contained in desiccators were used to generate the respective r.h. $(NH_4)_2SO_4$, r.h. 81%; $NH_4NO_3$, r.h. 63%; $K_2CO_3$, r.h. 43%. Matured mildly desiccated somatic embryos were transferred on their filter paper supports to unsealed petri dishes which were then placed within the 81% r.h. desiccator. For r.h. below 81%, petri dishes containing the cultures were transferred successively to the lower r.h. desiccators at 3–4 d intervals to reduce the desiccation rate. All cultures were maintained for a minimum of 7–10 d at the final required r.h. Total secondary desiccation treatment times were 14 d.

Following secondary desiccation, unimbibed and imbibed somatic embryos had moisture contents in the range 20–31% and 56–65%, respectively (Table 3). Mean moisture contents directly following the 81% r.h. treatment were marginally higher than those following the 43% r.h. treatment, and closely approximated those for unimbibed zygotic embryos. Somatic embryos from the different osmotic treatments had similar moisture contents after secondary desiccation. The controls matured without PEG underwent the greatest moisture loss during secondary desiccation. Imbibed zygotic embryos had moisture contents of 62% and imbibed somatic embryos had moisture contents of 56–65%.

TABLE 3

Moisture content (% ± confidence limits, P = 0.05) of desiccated unimbibed, and desiccated imbibed white spruce somatic and zygotic embryos. The somatic embryos were matured in different PEG concentrations (%) then given a 43 or 81% relative humidity desiccation treatment.

| | | | Somatic PEG concentration (%) | |
| --- | --- | --- | --- | --- |
| | Zygotic | r.h. (%) | 0 | 5 | 7.5 |
| Unimbibed | 32.5 ± 3.0 | 81 | 25.7 ± 9.9 | 29.4 ± 3.0 | 31.2 ± 6.9 |
| | | 43 | 21.9 ± 10.5 | 20.1 ± 3.7 | 27.8 ± 8.7 |
| Imbibed | 61.9 ± 3.1 | 81 | 58.0 ± 10.8 | 64.7 ± 4.1 | 61.5 ± 4.9 |
| | | 43 | 59.1 ± 9.1 | 56.6 ± 5.0 | 59.1 ± 2.4 |

Plantlet Regeneration Following Slow Secondary Desiccation

Plantlet generation was studied from white spruce somatic embryos matured for 28 days with 16 µM and 5.0% PEG. Somatic embryos desiccated to low moisture contents were imbibed in the Petri dishes by flooding the filter paper supports with liquid plantlet regeneration medium. The dishes were then sealed with Parafilm and placed under low light [2 W m$^{-2}$, 12 h photoperiod, 20 W cool-white fluorescent lamps (Westinghouse)]. Those that survived and commenced development to plantlets were scored and transferred to fresh solidified plantlet regeneration medium 7–14 d after re-hydration.

Somatic embryos that were not given a secondary desiccation treatment were separated individually from the cultures following the maturation/postmaturation treatments. They were placed horizontally on fresh plantlet regeneration medium, and maintained at low light intensity (as above).

0, 5.0 and 7.5% PEG matured somatic embryos from the 81 and 43% r.h. treatments were weighed (unimbibed weight), imbibed for 5 h with germination medium, then gently blotted and weighed again (imbibed weight), prior to determining the dry weights. These measurements were repeated three to six times per treatment with 20 somatic embryos per replicate.

Post-maturation and Slow Secondary Desiccation

The appearance of mature somatic embryos and regenerated plantlets is shown in FIG. 3. All secondary desiccation treatments led to somatic embryos of a dry and shrunken appearance as shown in FIG. 3A (bar: 2 mm). After the application of liquid medium, somatic embryos imbibed water, and within 2 h had regained a swollen appearance (FIG. 3B). Survivors placed under low light developed into plantlets within 7 d as seen in FIG. 3C (bar: 5 mm). The timing of the slow secondary desiccation treatment was critical (Table 4).

TABLE 4

Overall effects of maturation treatment (16 µM ABA ± 7.5% PEG for 28 d), ABA-free post-maturation (14 d), and 81% relative humidity secondary desiccation treatment (14 d) on white spruce somatic embryo survival and plantlet regeneration.

| ABA 1° mild desiccation maturation treatment | ABA-free post-maturation | Fresh (F) or severely desiccated (D) | Plantlet regeneration |
| --- | --- | --- | --- |
| PEG absent | No | D | Poor |
| | No | F | + |
| | Yes | D | − |
| | Yes | F | + |
| 7.5% PEG | No | D | + |
| | No | F | − |
| | Yes | D | − |
| | Yes | F | Poor |

(+) Plantlets regenerated; (−) no embryo survival.

Somatic embryos initially survived the 81% r.h. treatment only if the treatment was applied directly following transfer of the somatic embryos from the ABA maturation media (with or without PEG). Hence, when somatic embryos matured with 7.5% PEG were further desiccated directly, somatic embryos developed to plantlets. PEG-matured somatic embryos did not develop further in the absence of secondary desiccation treatment but swelled and became vitrified. As it can be seen in FIG. 3D, the axes of the somatic embryos have failed to elongate normally, the plantlet is vitrified, and the root is necrotic (bar: 3 mm). Those PEG matured embryos given post-maturation instead of secondary desiccation developed to plantlets with swollen bases and no roots. Thus, normal regeneration of PEG matured embryos occurred only if the embryos were subsequently desiccated to low moisture contents. Furthermore, secondary desiccation following post-maturation in the absence of ABA (with or without PEG) was lethal to all embryos.

Effect of Slow Secondary Desiccation Upon Filter Paper Supports

Somatic embryos survived secondary desiccation at high frequency when the embryos were desiccated while retained as whole callus on the filter paper supports and placed in an unsealed petri dish in an 81% r.h. environment. Also, it was noted that somatic embryos did not survive secondary desiccation in an unsealed petri dish placed in an 81% r.h. environment, if they were removed from the main callus and filter paper supports. As slower desiccation occurred in the former, then these experiments suggested that somatic embryos were intolerant to rapid desiccation to low moisture contents. However, it was subsequently found that somatic embryos can survive rapid secondary desiccation to low moisture contents; furthermore, when somatic embryos matured for 8 weeks with 16 µM ABA and 7.5% PEG were separated from the main callus but placed on the same filter paper beside the whole callus, somatic embryos survived slow secondary desiccation (81% r.h.) at high frequency, but recovered plantlets were abnormal—the embryos did not elongate normally, but remained stunted. This was overcome if the mature somatic embryos were removed from the callus and washed in culture medium containing ABA and PEG, then placed on filter paper moistened with the same medium, prior to further desiccation.

Survival and Plantlet Regeneration Following Secondary Slow Desiccation to Low Moisture Contents Table 5 shows that somatic embryo survival and plantlet regeneration generally diminished with increasing severity of the secondary desiccation treatments for—somatic embryos matured for only 4 weeks.

TABLE 5

Regeneration (% ± s.e.) Of plantlets from white spruce somatic embryos that were matured in the presence of different % concentrations of PEG (all with 16 μM ABA), then further desiccated in climates of different % relative humidity (r.h.)

| r.h. (%) | PEG concentration (%) | | | | |
|---|---|---|---|---|---|
| | 0 | 2.5 | 5 | 7.5 | 10 |
| 81 | 44.3 ± 7.8 | 61.9 ± 10.2 | 35.2 ± 7.2 | 33.9 ± 6.6 | 37.6 ± 10.1 |
| 63 | 34.5 ± 11.6 | 21.9 ± 7.4 | 28.3 ± 8.1 | 17.3 ± 4.1 | 12.6 ± 4.8 |
| 43 | 8.3 ± 8.2 | 9.9 ± 8.9 | 7.9 ± 4.5 | 8.6 ± 4.6 | 0.2 ± 0.2 |

Controls (no PEG treatment or secondary desiccation) developed to plantlets at a frequency of 43% (s.e. ±12%). The inclusion of PEG during the maturation phase did not greatly influence the desiccation survival of the somatic embryos; however, results within treatments were very variable. Highest mean survival and plantlet regeneration at 81% r.h. occurred with the 2.5% PEG matured somatic embryos (62%). Survival of the other osmotic treatments was within the range 34–44%. Following the 43% r.h. treatment, survival was less than 10% for all osmotic treatments, and less than 1% for the 10%-PEG matured embryos. Although somatic embryos matured without PEG regenerated to plantlets, often these were aberrant, especially following the more severe secondary desiccation treatments of low r.h. For example, rooting was retarded, not all cotyledons elongated, and hypocotyls were often curled following elongation. It was also observed that the somatic embryos matured without PEG did not remain quiescent after transfer from the ABA media, but greened and underwent precocious germination during the first few days of the secondary desiccation treatment. Somatic embryos from the other osmotic treatments remained quiescent throughout secondary desiccation.

Effect of Culture Time on Tolerance to Slow and Rapid Secondary Desiccation

It was of interest to examine whether these somatic embryos were tolerant to rapid secondary desiccation, such as drying on the lab bench at ambient r.h. Bench drying is simpler to perform than drying in controlled environments. It was also of interest to determine if there was a particular maturation period that was optimal for survival. Therefore, somatic embryos matured for 4, 5, 6, 7 and 8 weeks on medium containing 16 μM ABA and 7.5% PEG, were each transferred on their filter paper supports either to sterile petri dishes, which were left unsealed on the lab bench for three days or 50 to 81% r.h. desiccator for slow drying for 2 weeks. The ambient r.h. was about 35% during the time of the air drying experiments, and the laboratory temperature was 20–25° C. 10–17 replicates were prepared per treatment. After secondary desiccation, the somatic embryos were hard and dry. Somatic embryos were then imbibed as before with half-strength PGR-free medium and scored for plantlet regeneration after 2–3 weeks. Results (±standard errors) are shown in FIG. 15.

It can be seen from FIG. 15 that somatic embryos survived slow secondary drying treatments after 4 weeks of maturation, and regenerated to plantlets at a frequency of about 60%. This frequency improved slightly further following 6, then 8 weeks maturation, achieving in the order of 80% plantlet regeneration. Somatic embryos matured for just 4 weeks then further dried more rapidly at ambient r.h., did not regenerate to plantlets. Often with these embryos, the root meristem survived and developed a root, but the shoot apex had died, so remained white and did not elongate. Rapidly air dried somatic embryos were capable of regenerating to plantlets after 5 and 6 weeks maturation, but at low frequency (less than 10 and 25% respectively). By the 7th week of maturation these somatic embryos survived and regenerated to plantlets at a frequency of just over 60%. Thus, from this graph it is clear that optimal desiccation tolerance to drying to low moisture levels is achieved after a minimum of 7 weeks of maturation in the presence of ABA and non-permeating osmoticum. The quality of the regenerated plantlets following the rapid secondary drying treatment was good, and it appeared that root elongation often appeared earlier and was more vigorous following rapid drying.

Evaluation of the Molecular Size Threshold of Solutes for Promoting Maturation of White Spruce Somatic Embryos During Primary Treatment of Mild Desiccation and Maturation In order to determine the effective molecular weight and size range of solutes that promote the maturation of immature white spruce somatic embryos, they were matured in half-strength LP maturation medium containing a range of different solutes of differing molecular weight. Five replicates were prepared per treatment, and treatments were repeated twice. All media contained 20 μM ABA and a base level of 3% sucrose. The supplemented solutes were included at 7.5% (w/v), which supplemented solutes constituted an addition to the 3% base level of sucrose. The treatment time was 9 weeks. The sucrose, mannitol, and PEGs 200, and 400 treatments were also tested at 2.5 and 5% (w/v), but as these concentrations did not result in recovery of any mature embryos, results for these concentrations are not presented. Similarly, PEG 8000 led to poor maturation as this solute prevented effective gelling of the medium. The somatic embryos remained wet throughout the maturation treatment which led to poorly formed embryos at low frequency. Therefore, results for PEG 8000 are excluded here; however, PEG 8000 was tested in a liquid flow bioreactor where it effectively promoted maturation (see later). For all treatments, only normal looking cotyledonary stage opaque white embryos were scored and used for lipid analyses. Levels of lipid triacylglycerols (TAGs) were analyzed as described later and results provided are means of two replicates.

A low recovery of mature control (no PEG) somatic embryos was recorded. Many more mature embryos were initiated in this treatment but the majority underwent precocious germination during later phases of the treatment, so were not scored or used for lipid determinations. It can be seen from Table 6 that the molecular weight of PEGs capable of promoting maturation is initiated at the 600–1000 molecular weight range. PEGs of 200 and 400 were toxic and no callus growth was observed throughout the maturation treatments, similar to the mannitol and sucrose treatments. PEG 600 was somewhat toxic; the mean number of mature embryos recovered was similar to the control in the absence of any precocious germination, and lipid levels were lower than control levels. PEGs of greater than 1000 were the more effective at promoting maturation. PEG 1000 led to recovery of a large number of mature somatic embryos. Visual comparison showed these embryos were smaller than other effective treatments, giving a high % DW of TAG, but lower total lipid content. Visual comparisons of their tolerance to further desiccation to lower moisture levels (at 81% r.h.) and development to plantlets, showed a variable response among replicates; furthermore the quality of regenerated plantlets was more variable than with the higher molecular weight osmotica. Thus, it is likely that PEG 600 and to a lesser extent PEG 1000, do slowly penetrate the cell walls of the somatic embryos. It therefore appears that the threshold molecular size of osmotica that effectively promotes maturation is in the region of 30–35Å, and it is considered that this is achieved due to their exclusion from entering the cell through pores in the cell walls, so exerting a non-toxic moisture stress.

TABLE 6

Comparison of the effect of molecular weights and molecular sizes of solutes, at 7.5% concentration with 20 μM ABA, on maturation response (mature embryos per replicate ± SE, and lipid contents) of white spruce somatic embryos.

| Solute | Molecular weight | Molecular size (Å) | Mature embryos per replicate | TAG (% embryo DW) | TAG (mg) per embryo |
|---|---|---|---|---|---|
| Control (3% sucrose) | 342 | 10 | 6 ± 1.0 | 24.4 | 201 |
| Sucrose | 342 | 10 | 0 | — | — |
| Mannitol | 182 | 8 | 0 | — | — |
| PEG 2000 | –200 | <30 | 0 | — | — |
| PEG 400 | –400 | <30 | 0 | | |
| PEG 600 | –600 | <30 | 8.2 ± 2.6 | 22.3 | 123.8 |
| PEG 1000 | >950 | >30 | 44.6 ± 5.5 | 34.8 | 201 |
| PEG 4000 | >3000 | >30 | 31.5 ± 2.6 | 31.1 | 250.5 |
| Dextran 6000 | –6000 | >30 | 17.0 ± 2.6 | 28.8 | 260 |
| Dextran 80,000 | –80000 | >30 | 16.2 ± 1.9 | 25.9 | 213.2 |

Maturation of Cultured White Spruce Somatic Embryos

A one-week-old white spruce suspension culture, previously grown in liquid medium containing 10 μM 2,4-D and 5 μM BA, was collected by filtration. The somatic embryos were rinsed in growth regulator free liquid medium, 3–6 g of somatic embryos were transferred to a fresh 250 ml flask containing 50 ml of half-strength liquid medium (1% sucrose) containing 5 μM BA with or without auxin reduced by ¹⁄₁₀. The somatic embryos were then cultured for 1 week. After this time they were again collected by filtration, and a 20% suspension (w/v) of somatic embryos was prepared in fresh BA containing medium. This was inoculated (0.75 ml aliquots) onto filter paper supports overlying maturation medium. The embryos were then cultured following the description above. Both the pre-treatments enhanced maturation substantially and can be said to have a synergistic effect with PEG/ABA treatments on maturation frequencies. Inclusion of low auxin was beneficial.

Maturation of White Spruce Somatic Embryos Using a Continuous Flow, Solid-support Bioreactor A bioreactor was fabricated out of a high density plastic container 15×21×6 cm, with air tight lid. One entrance and one exit port were situated at opposite corners of the chamber base. The inside base on the chamber was overlaid with a cotton-wool pad, on which was placed a filter paper support (Whatman no 1; cut to 15×21 cm). Liquid maturation medium (half strength LP medium with 7.5% PEG 8000, 3% sucrose and 20 μM ABA) was supplied from an 8 L vessel containing 4 L of culture medium. The whole apparatus was autoclaved. The bioreactor retained approximately 450 ml of liquid medium within the cotton pad. Culture medium was pumped through the bioreactor chamber at a flow rate of 20 ml per h., for 3 h per day. This provided the equivalent to approximately one full medium change per week. Suspension-cultured immature somatic embryos were inoculated onto the filter paper support as a 20% suspension (w/v) in growth-regulator-free medium. Approximately 10–15 ml of suspension was distributed over the filter-support surface. The system was run for 7 weeks. The filter paper supporting the mature mildly desiccated somatic embryos was then removed, and cut into smaller pieces for easier handling. The mature embryos were then further desiccated to low moisture contents either on the supports in an environment of 63% r.h. for two weeks then imbibed in half strength hormone free medium, or air dried and analyzed for storage lipid (TAG). Lipid analyses were conducted as described in section B of preferred embodiments, using two replicates of 100 embryos each.

Somatic embryos underwent maturation within the bioreactor chamber yielded high quality mature embryos. The embryos had well developed cotyledons. The bioreactor yielded approximately 500 mature embryos of this quality. It is expected that this number can be improved with optimizing of the conditions within the bioreactor, and the size of the bioreactor itself can be increased if desired. The lipid levels are shown in Table 7 and these levels compare favourably to the levels observed in 6–8 week somatic embryos matured on agar medium. The somatic embryos survived further desiccation at high frequency and germinated vigorously into normal looking plantlets. Thus, using this method, large numbers of embryos of excellent quality have been produced with minimal cost and manipulation. Using this method it is possible to slowly increase ABA and/or osmotic concentrations over the first few days of maturation, and similarly to modify their concentrations prior to conclusion of the production run. However, it is envisaged that levels of ABA will be maintained at a substantially constant level throughout the majority of the maturation period. As the medium is supplied regularly while spent medium is removed, it may also be possible to provide a modified culture medium with more suitable levels of nutrients than are presently provided by agar cultures. Additionally osmotic and ABA concentrations may need to be re-optimized. It is to be noted that other combinations of flow ratio and flow times of the medium can be used efficiently.

TABLE 7

Characteristics of white spruce somatic embryos matured for 7 weeks in a continuous flow, solid support bioreactor.

| DW(mg) | % DW of TAG (FAMES) | TAG (FAMES) (μg per embryo) | TAG/TL % | Plantlet regeneration frequency (%) |
|---|---|---|---|---|
| 0.56 | 25.2 | 140 | 75.95 | 84.4 |

Desiccation of Black and Norway Spruce Somatic Embryos

Somatic embryos of white spruce, Norway spruce and black spruce have been matured and desiccated to a low moisture contents and regenerated to plantlets using these methods. The conditions found suitable for white spruce were tested on Norway and black spruce. Thus, suspension cultured black and Norway spruce somatic embryos were washed in growth-regulator-free medium, and a 20% suspension (w/v) was prepared in fresh growth-regulator-free medium. Aliquots (0.75 ml) were pipetted onto half strength culture medium containing 7.5% PEG 4000 and 16 (±) $\mu$M ABA. The somatic embryos were matured for 4 weeks then further desiccated on their filter paper supports in an environment of 81% r.h. for 2 weeks. The Norway and black spruce somatic embryos survived and regenerated to plantlets at frequencies of about 35 and 65%, respectively. It is likely that these values could be improved further following optimization of the ABA and osmotic concentrations, and increasing the length of the maturation period to at least 7 weeks. Norway spruce somatic embryos survived at lower frequency, however, the culture was not well established in suspension culture which was only 3 weeks old, so overall maturation was poor. Suspension cultures usually require up to 3 months establishment before embryos undergo effective maturation.

B. Determination of Lipid Composition of Matured and Desiccated White Spruce Somatic Embryos Somatic Embryo Maturation Maturation of the immature suspension cultured white spruce somatic embryos (line WS1) was carried out using the methods described previously in Part A (Maturation and Dessication) of this Description of Preferred Embodiments.

Experiments were set up to observe the effects of different culture conditions on somatic embryo lipid biosynthesis. Control somatic embryos were matured for 4 weeks on maturation medium containing 16 $\mu$M ABA (±racemic, product number A 2784; Sigma, St Louis, USA). To observe the effects of osmoticum, PEG-4000 (Fluka AG) was included in the maturation medium at concentrations of 2.5, 5.0, 7.5, and 10% (w/v), all with 16 $\mu$M ABA. Somatic embryos were maintained on these media for 4 weeks in the dark prior to lipid analysis.

To test the effect of culture time on lipid biosynthesis somatic embryos were maintained on maturation medium which contained 16 $\mu$M ABA and 7.5% PEG, for 2, 4, 6, or 8 weeks prior to lipid analysis. Cultures that were matured for longer than 4 weeks were transferred to fresh medium after this time. The lipid contents of immature somatic embryos from suspension culture were also determined.

Investigations were conducted to observe the effects of different ABA concentrations, in the presence of PEG, on lipid biosynthesis. Somatic embryos were, therefore, maintained on maturation medium containing 7.5% PEG and 12, 16, 24, or 32 $\mu$M ABA for 8 weeks. To observe the effects of slow secondary desiccation on lipid biosynthesis, somatic embryos matured in these treatments were also transferred into an environment of 81% r.h., as described previously to achieve further desiccation to low moisture levels. Matured somatic embryos were transferred on their filter-paper supports to unsealed petri dishes which were then placed within the 81% r.h. desiccator. Total secondary desiccation treatment time was 2 weeks. Somatic embryos were analyzed for lipid after imbibing in liquid medium for 1–2 h, in order to free them from the filter-paper supports. Results were compared to those of somatic embryos matured under the same conditions but not further desiccated.

For comparisons with somatic embryos, zygotic embryos were dissected from the megagametophytes of mature seeds after they had been imbibed for 16 h in distilled water. In addition, whole seed was analyzed for lipid.

Plantlet Regeneration

Following maturation and further desiccation white spruce somatic embryos intended for further culture were imbibed in liquid plantlet regeneration medium, using a method modified slightly from the method described previously in A., in order to reduce the rate of water uptake. Thus, instead of flooding the liquid medium directly onto the somatic embryos, 1–2 ml was added to the petri dishes which were then maintained on a slope with the filter-paper carriers dipped into the liquid. The medium was first absorbed by the filter paper and conveyed to the somatic embryos. After imbibition, somatic embryos were maintained under low light intensity as described before. One week later, regenerating plantlets were separated and cultured individually. They were placed horizontally on fresh plantlet regeneration medium, and maintained at the same low light intensity. Four weeks after imbibing, they were analyzed for storage lipid and the results compared to those of fully expanded zygotic seedlings derived from embryos dissected from the megagametophytes of mature seed and grown in vitro for 4 weeks.

Lipid Analysis

The whole white spruce seeds, isolated zygotic embryos, somatic embryos from the various treatments, and regenerated plantlets and zygotic seedlings were counted, blotted dry, and fresh weights determined. The samples were then placed in an oven at 80° C. for 24 h and dry weights recorded. Lipids were extracted from fresh tissues by the hexane/isopropane method of Hara and Radin (1978), after first placing the samples in boiling isopropane for 10 min. TAGs were separated from total lipid extracts by thin layer chromatography using HPTLC-Fertigplatten Kieselgel 60 plates (Mandel Scientific Co., Toronto, Canada). Plates were developed in a solvent system containing petroleum ether: diethyl ether: acetic acid (82:18:1). TAGs were identified using authentic standards and scraped from the plates using a razor blade. Fatty acid methyl esters (fames) were prepared from TAGs and total lipid extracts, as previously described (Pomeroy et al. 1991). Sample sizes consisted of 50–180 somatic or zygotic embryos, 25 whole seeds, and 5 zygotic seedlings or regenerated somatic plantlets. Each lipid extract sample was divided into 2–3 replicates for analysis, and experiments were repeated three times. Results shown are means of one experiment.

Microscopy

Somatic and zygotic embryos of white spruce were prepared for transmission electron microscopy (TEM) according to previously published methods (Fowke 1984). Mature dry seeds were imbibed in tap water for 16, or 65 h prior to zygotic embryo removal and fixation. Somatic embryos desiccated to low moisture contents were rapidly imbibed by complete immersion in liquid plantlet regeneration medium for 2 h prior to fixation. Somatic embryos were first cut longitudinally to ensure subsequent penetration of fixatives and resin. Thick sections (i.e., 1 $\mu$m) were cut from the same plastic embedded material and stained with toluidine blue (1% w/v in 1% borax solution) for observations by light microscopy.

Results

A. Lipid Composition

Fatty acid compositions were determined for both TL and TAG, but since values were similar throughout, only TAG fatty acid compositions are provided with the exception of the data for zygotic embryos and seeds (Table 8).

TABLE 8

A, TL (fatty acid methyl esters (fames)) and TAG (fames) contents, and B, fatty acid compositions, of white spruce mature whole seed and isolated zygotic embryos.

A

| | TL | | TAG | | TAG/TL |
|---|---|---|---|---|---|
| | μg (individual)$^{-1}$ | % d wt | μg (individual)$^{-1}$ | % d wt | % |
| Seed | 688 | 29 | 372 | 16 | 54 |
| embryo | 62 | 51 | 44 | 36 | 71 |

B

Fatty acid composition of TL and TAG (%)

| | | 0.6666667 | 0.668 | 0.75 | 0.75 | 0.251 | 0.75 | 18:2$^b$ | 0.75 | ΣC-20, 22$^c$ |
|---|---|---|---|---|---|---|---|---|---|---|
| seed | TL | 2.4 | 0.2 | 1.3 | 15.8 | 4.5 | 45.0 | 29.6 | 0.2 | 1.1 |
| | TAG | 2.7 | 0.2 | 1.3 | 16.9 | 4.7 | 42.8 | 28.6 | 0.2 | 2.4 |
| embryo | TL | 5.1 | 1.0 | 1.6 | 18.4 | 3.3 | 48.9 | 20.7 | 0.3 | 0.8 |
| | TAG | 4.9 | 0.9 | 1.6 | 19.5 | 3.0 | 49.1 | 19.4 | 0.60 | 0.9 |

$^a$Double bond in the C-7 position instead of the C-9.
$^b$Double bond at the C-5 and C-9 positions instead of the C-9 and C-12 positions.
$^c$Represents the sum of all identified C-20 and C-22 fatty acids.

Zygotic Embryos and Seeds

A large proportion of the dry weight of zygotic embryos was due to lipid (Table 8A). They consisted of 51% TL by dry weight, 36% of the dry weight (16% imbibed fresh weight; not shown) was attributed to TAG; therefore, the ratio of TAG to TL was 71%. Isolated zygotic embryos contained only about 12% of the TAG present in whole seed. Thus, TAG was distributed between the megagametophyte and the zygotic embryo at a ratio of 7.5:1, respectively. The low % dry weight value of lipid from whole seed compared to isolated zygotic embryos was due in part to the inclusion of the seed coats during analysis. The fatty acid analysis of TL and TAG for isolated zygotic embryos and whole seeds showed that the compositions were similar (Table 8B). The predominant fatty acids in both zygotic embryos and whole seeds of white spruce were two separate molecular species of 18:2, comprising around 70% of total fatty acids. The most abundant species of 18:2 in both embryos and seeds has double bonds at the usual C-9 and C-12 positions (Δ9,12). However, an unusual 18:2 fatty acid with double bonds at the C-5 and C-9 positions (Δ5,9) comprised 20–30% of total fatty acids. The total content of 18:1 was about 20% of total fatty acids, with around 80% of the 18:1 with the double bond at the C-9 position. The 16:2, 18:0, 18:3, and longer chain fatty acids were each present at less than 2%.

Somatic Embryos

The effect of PEG concentration on lipid biosynthesis and fatty acid composition after 4 weeks culture with 16 μM ABA are shown in Table 9.

TABLE 9

Influence of PEG concentrations on A, TL (fames) and TAG (fames) accumulation and B, fatty composition of white spruce somatic embryos. These were matured for 4 weeks with 16 μM ABA.

A

| | TL | | TAG | | TAG/TL |
|---|---|---|---|---|---|
| PEG % | μg (embryo)$^{-1}$ | % d wt | μg (embryo)$^{-1}$ | % d wt | % |
| 0 control | 32 | 21 | 23 | 15 | 72 |
| 2.5 | 33.2 | 30 | 20.8 | 19 | 63 |
| 5 | 44 | 31 | 29 | 21 | 66 |
| 7.5 | 40.6 | 30 | 28 | 21 | 69 |
| 10 | 37 | 27 | 26 | 20 | 70 |

B

Fatty acid composition of TAG (%)

| PEG % | 0.667 | 0.668 | 0.75 | 0.75 | 0.251 | 0.75 | 18:2$^b$ | 0.75 | ΣC-20, 22$^c$ |
|---|---|---|---|---|---|---|---|---|---|
| 0 control | 9 | 1.9 | 2.4 | 23.3 | 2.2 | 45.6 | 11.3 | 1.1 | 3.2 |
| 2.5 | 9.1 | 1.9 | 2.4 | 23.4 | 2.3 | 45.2 | 11.4 | 1.1 | 3.3 |

TABLE 9-continued

Influence of PEG concentrations on A, TL (fames) and TAG (fames) accumulation and B, fatty composition of white spruce somatic embryos. These were matured for 4 weeks with 16 μM ABA.

| 5 | 8.5 | 1.6 | 2.6 | 24 | 2.1 | 46.4 | 11 | 1.1 | 2.7 |
| 7.5 | 8.5 | 1.6 | 2.7 | 24.3 | 2.4 | 45 | 11.1 | 1.2 | 3.2 |
| 10 | 7 | 1.2 | 2.5 | 23.3 | 3.4 | 41 | 16.6 | 0.9 | 4.3 |

[a] Double bond in the C-7 position instead of the C-9.
[b] Double bond at the C-5 and C-9 positions instead of the C-9 and C-12 positions.
[c] Represents the sum of all identified C-20 and C-22 fatty acids.

PEG increased the quantity of TAG in somatic embryos (Table 9A), but they did not achieve levels as high as those recorded for zygotic embryos (c.f., Table 8A), either on a per embryo, or % dry weight basis. In the absence of PEG somatic embryos contained about 50% of the amount of TL and TAG present in the zygotic embryos. TL and TAG per somatic embryo increased with 5.0 and 7.5% PEG compared to the control, and reached close to 70% of the amount of TAG observed in zygotic embryos. The % dry weight TAG increased by 40% with 5 and 7.5% PEG, achieving 58% of the dry weight value observed in zygotic embryos. TAG fatty acid composition was not influenced to any great extent by different concentrations of osmoticum after 4 weeks of culture (Table 9B). Furthermore, at all PEG concentrations, the somatic embryos contained the same predominant fatty acids as zygotic embryos (Table 8B), although the proportion of 18:1 was higher and that of 18:2 (Δ5,9) was lower in the somatic embryos.

The effect of culture time and 7.5% PEG on lipid biosynthesis and fatty acid composition is shown in Table 10.

Somatic embryos continued to accumulate TL and TAGs throughout the 8-week culture period (Table 10A). For example, during 4–6 weeks with PEG the weight of TL and TAG per embryo increased to levels greater than those recorded for zygotic embryos and by 8 weeks the somatic embryos had four times more TAG compared to zygotic embryos. The increase was more modest when expressed as % dry weight, achieving 72% of the level recorded for zygotic embryos; even so, somatic embryos contained 45% more TAG at 8 weeks compared to those at 4 weeks. The TAG component of the somatic embryos was 26% dry weight (11% fresh weight; not shown) by the 8th week of culture. The effect of PEG on TAG accumulation was clearly evident after 8 weeks' culture. At this time somatic embryos matured with 7.5% PEG had accumulated 50% more TAG per embryo compared to non-PEG-treated somatic embryos, and contained almost twice as much TAG on a % dry weight basis. The % of TAG to TL increased during maturation with PEG, and resulted in a higher ratio of TAG to TL compared to somatic embryos matured without PEG. The TAG fatty

TABLE 10

Influence of culture time on A, TL (fames) and TAG (fames) accumulation and B, fatty acid composition of white spruce somatic embryos. These were matured with 16 μM ABA, and 0% or 7.5% PEG.

A

| Time (Weeks) | TL μg (embryo)$^{-1}$ | % d wt | TAG μg (embryo)$^{-1}$ | % d wt | TAG/TL % |
|---|---|---|---|---|---|
| 0 | ND | 6 | ND | 2 | 38 |
| 2 + PEG | ND | 8 | ND | 3 | 30 |
| 4 + PEG | 57.2 | 28 | 36.1 | 18 | 63 |
| 6 + PEG | 128.7 | 30 | 72.7 | 17 | 57 |
| 8 + PEG | 238.6 | 36 | 172.7 | 26 | 72 |
| 8 − PEG | 173.3 | 21 | 113.3 | 14 | 65 |

B

| Time (Weeks) | Fatty acid composition of TAG (%) | | | | | | | | |
|---|---|---|---|---|---|---|---|---|---|
| | 0.667 | 0.668 | 0.75 | 0.75 | 0.251 | 0.75 | 18:2[b] | 0.75 | ΣC-20, 22[c] |
| 0 | 8.8 | 2.4 | 2.8 | 29.1 | 6.4 | 31.5 | 7.8 | 5.1 | 6.1 |
| 2 + PEG | 9 | 2.4 | 2.9 | 29.4 | 6.2 | 31.5 | 7.8 | 4.5 | 6.3 |
| 4 + PEG | 7.9 | 1.5 | 3.2 | 25.2 | 2.3 | 45 | 11.3 | 1.2 | 2.4 |
| 6 + PEG | 6.2 | 1.2 | 2.2 | 23.3 | 3.1 | 46 | 13.8 | 0.9 | 3.2 |
| 8 + PEG | 4.3 | 0.7 | 1.3 | 24.6 | 3.9 | 47.2 | 15.8 | 0.4 | 1.7 |
| 8 − PEG | 6.3 | 0.1 | 1.8 | 23.9 | 2.7 | 48.9 | 14 | 0.9 | 1.4 |

ND, not determined.
[a] Double bond in the C-7 position instead of the C-9.
[b] Double bond at the C-5 and C-9 positions instead of the C-9 and C-12 positions.
[c] Represents the sum of all identified C-20 and C-22 fatty acids.

acid composition of somatic embryos changed with culture time (Table 9B) and by 8 weeks had reached ratios that closely approximated zygotic levels (c.f., Table 8B). The most abundant fatty acids present in immature suspension cultured somatic embryos were 18:1 (Δ9) and 18:2 (Δ9,12). The 7.5% and 0% PEG treated somatic embryos had similar fatty acid composition values, which again showed that the PEG osmoticum had little effect on fatty acid composition even after 8 weeks culture. During the 8-week study period, the trend was for the 18:2 (Δ9,12 and Δ5,9) fatty acids to increase while the other fatty acids decreased proportionately, resulting in fatty acid compositions similar to mature zygotic embryos (Table 7B).

The effects of ABA concentration and secondary desiccation treatments on lipid biosynthesis and fatty acid composition after 8 weeks with 7.5% PEG are shown in Table 11.

more—showing that lipid accumulation continued during the secondary desiccation treatment. On a per embryo basis, 16 μM ABA yielded the most TAG per embryo (214 μg). This is five times the zygotic value (Table 7A), and about a nine fold increase over the original controls (Table 9A). On a % dry weight basis 24 μM ABA was optimal producing somatic embryos containing 30% TAG. This is 83% of the zygotic value, and twice the value of the initial control somatic embryos. On a % fresh weight basis all ABA treatments led to somatic embryos containing approximately 11% TAG (not shown), which is about 70% of the zygotic level. The TAG fatty acid composition was not modified appreciably by ABA at the concentrations tested (Table 4B), however, following desiccation the proportion of 18:1 (Δ9) consistently decreased slightly, while the proportion of 18:2 (Δ9,12) underwent a slight increase, resulting in values that

TABLE 11

Influence of ABA concentration and slow secondary desiccation (81% r.h.)
On A, TL (fames) and TAG (fames) accumulation and B, fatty acid composition
of white spruce embryos. These were matured for 8 weeks with 7.5%
PEG, then either assayed for lipid in the mildly desiccated
hydrated state (H) directly following maturation, or subsequently
further desiccated (D) for 2 weeks at 81% relative humidity.

A

| ABA (μM) | Hydrated (H) or Desiccated (D) | TL μg (embryo)$^{-1}$ | % d wt | TAG μg (embryo)$^{-1}$ | % d wt | TAG/TL % |
|---|---|---|---|---|---|---|
| 12 | H | 146 | 18 | 116 | 14 | 79 |
|  | D | 220 | 31 | 186.6 | 26 | 85 |
| 16 | H | 179 | 22 | 143 | 17 | 80 |
|  | D | 260 | 35 | 214 | 28 | 82 |
| 24 | H | 170 | 26 | 131 | 20 | 77 |
|  | D | 232.5 | 37 | 186.2 | 30 | 80 |
| 32 | H | 193 | 26 | 130 | 17 | 67 |
|  | D | 264 | 31 | 170 | 20 | 64 |

B

| ABA (μM) | Hydrated (H) or Desiccated (D) | Fatty acid composition of TAG (%) | | | | | | | | |
|---|---|---|---|---|---|---|---|---|---|---|
|  |  | 0.6667 | 0.668 | 0.75 | 0.751 | 0.251 | 0.751 | 18:2[b] | 0.75 | ΣC-20, 22[c] |
| 12 | H | 6.4 | 1.1 | 1.9 | 26.9 | 3.7 | 44.4 | 13.2 | 0.9 | 1.4 |
|  | D | 5.2 | 0.1 | 1.3 | 22.5 | 3.6 | 50 | 15.4 | 0.5 | 1.4 |
| 16 | H | 6.8 | 1.2 | 1.8 | 26.1 | 3.5 | 45.4 | 13.5 | 0.6 | 1 |
|  | D | 5 | 0.1 | 1.4 | 22.3 | 3.8 | 50 | 15.4 | 0.5 | 1.5 |
| 24 | H | 7.2 | 1.2 | 1.5 | 23.7 | 3.5 | 46.4 | 14.7 | 0.5 | 1.2 |
|  | D | 5.3 | 0.1 | 1.4 | 23 | 3.8 | 49.5 | 15 | 0.5 | 1.5 |
| 32 | H | 6.8 | 1.1 | 1.7 | 24.5 | 3.5 | 45.8 | 14.6 | 0.4 | 1.6 |
|  | D | 5.6 | 0.1 | 1.4 | 22.9 | 3.8 | 48.4 | 14.9 | 0.4 | 2.5 |

[A]Double bond in the C-7 position instead of the C-9.
[B]Double bond at the C-5 and C-9 positions instead of the C-9 and C-12 positions.
[C]Represents the sum of all identified C-20 and C-22 fatty acids.

In somatic embryos not subjected to secondary desiccation, TL increased with increasing ABA concentration (Table 11A). ABA at 16 μM, however, yielded the highest accumulation of TAG per embryo (143 μg), but on a % dry weight basis 24 μM ABA was higher (20%). Following secondary desiccation somatic embryos from all ABA concentrations displayed higher TL and TAG—those from the 16 and 24 μM ABA treatments contained over 30% more closely approximated zygotic values compared to somatic embryos not desiccated to low moisture contents.

Somatic Plantlets and Narcotic Seedlings

The TL and TAG content for regenerated somatic plantlets matured for 6 weeks with 16 μM ABA, 7.5% PEG, then further desiccated, and expanded zygotic seedlings grown from isolated zygotic embryos are compared in Table 12.

TABLE 12

A, TL (fames) and TAG (fames) contents, and
B, fatty acid compositions, of white spruce
expanded seedling and somatic plantlet following maturation
for 6 weeks on medium containing 16 µM ABA and 7.5% PEG
then further desiccated. The somatic plantlet and
zygotic seedling were both 4 weeks old.

A

| Time | TL | | TAG | | TAG/TL % |
|---|---|---|---|---|---|
| | µg (embryo)$^{-1}$ | % d wt | µg (embryo)$^{-1}$ | d % wt | |
| somatic plantlet | 26 | 2.3 | 8 | 0.7 | 31 |
| zygotic seedling | 20 | 2.1 | 6 | 0.63 | 30 |

B

| | Fatty acid composition of TAG (%) | | | | | | | | | |
|---|---|---|---|---|---|---|---|---|---|---|
| | 0.667 | 0.668 | 0.75 | 0.75 | 0.251 | 0.75 | 18:2$^b$ | 0.75 | ΣC-20, 22$^c$ | |
| somatic plantlet | 9.3 | 1 | 4.1 | 23.1 | 4.9 | 34.9 | 12.9 | 3.2 | 6.8 | |
| zygotic seedling | 14.8 | 0.6 | 6 | 37.9 | 2.9 | 23 | 7.8 | 3.2 | 3.8 | |

ND, not determined
$^a$Double bond in the C-7 position instead of the C-9
$^b$Double bonds at the C-5 and C-9 positions instead of the C-9 and C-12 positions
$^c$Represents the sum of all identified C-20 and C-22 fatty acids After 4 weeks' growth, the TL and TAG contents were similar (Table 12A). Low levels of lipid were present in both plant types, confirming the storage function of the TAGs, and their utilization for post-germinative growth. The data for the TAG fatty acid compositions showed similar trends (Table 12B). Thus, with both plant types the 18:2 (Δ9,12 and Δ5,9) decreased, while the proportions of the other fatty acids increased, in comparison to mature zygotic embryo levels (c.f., Table 8B). The somatic plantlets which were matured with 16 µM ABA had not achieved the degree of change observed for the zygotic seedlings. However, these results were inconsistent, and, furthermore, the level to which these changes occurred for zygotic seedlings varied greatly among experiments. Thus, it appears that the synthesis of 16:0, 18:0, and longer chain fatty acids in the seedlings and plantlets occurs at the expense of 18:2 (Δ9,12 and Δ5,9), which is the reverse of events observed during maturation (c.f., Table 10B).

B. Plantlet Conversion

During culture for 4–8 weeks with 7.5% PEG and 12–32 µM ABA, white spruce somatic embryos matured without germinating precociously. Somatic embryos desiccated to low moisture contents were dry and shrunken and had a translucent appearance. During secondary desiccation, however, many somatic embryos matured for 8 weeks with 12 pH ABA had undergone slight greening prior to drying. Precocious germination during the secondary desiccation treatment was more pronounced with somatic embryos matured for 8 weeks with 0 and 2.5' PEG, especially the former where considerable greening and hypocotyl elongation approached loot and survival did not occur. Thus, following prolonged maturation treatments, the higher ABA and PEG concentrations prevented the onset of precocious germination that otherwise occurred once ABA was removed for secondary desiccation. As shown in FIG. 4, fully imbibed, normal somatic embryos regained their pre-desiccated swollen opaque-white appearance, and converted to plantlets at high frequency. Embryos at this stage are light green and have commenced elongation (X 3.0 bar: 0.5 cm). For example, after 4, 6 or 8 weeks treatment with 16 µM ABA, a total of 700–800 normal-looking cotyledonary somatic embryos matured per treatment. As seen in FIG. 5, somatic plantlets regenerated from the 16–24 µM ABA treatments underwent root and hypocotyl elongation (X 2.7, bar 0.5 cm). Elongation is comparable in extent to zygotic seedlings grown in vitro from isolated embryos (see FIG. 6). The zygotic seedlings shown in FIG. 6 were obtained from mature embryos separated from the megagametophyte of mature seed and grown in vitro for 3 weeks under the same conditions as the somatic embryos of FIG. 5 (X 2.7, bar: 0.5 cm).

C. Microscopy

Mature white spruce zygotic embryos had distinct cotyledon and apical meristem regions, and procambium was evident as shown in FIG. 7A (X 76, bar: 0.2 mm). Lipid bodies (L) were abundant within the cells of the root, hypocotyl and areas adjacent to the shoot apical meristem, some apparently fusing together (arrow) as seen in FIG. 7B. Zygotic embryos dissected from mature dry seeds imbibed for 16 h also had numerous mature protein bodies (FIG. 7B (X 6500, bar: 3 µm)). However, the protein bodies within cells of zygotic embryos dissected from seeds imbibed for 65 h had enlarged, and the protein deposits had dispersed as seen in FIG. 8. The cells shown in FIG. 8 also contain numerous tightly packed lipid bodies (L) some apparently fusing together (arrow) (N: nucleus, X 6500, bar: 3 µm).

Somatic embryos matured for 8 weeks with 16 µM ABA and 7.5% PEG as seen in FIG. 9 contained large amounts of lipid (L) and compact protein bodies (P) similar to zygotic embryos from 16 h imbibed seed (X 6500, bar: 3 µm). After secondary desiccation and rapid imbibition for 2 h, the somatic embryos shown in FIG. 9 contained abundant lipid bodies comparable in distribution and frequency to the mature zygotic embryos from 65 h imbibed seed as seen in FIG. 10A. The cells are densely cytoplasmic and storage reserves are evident (small arrows). Note the rather flat meristem (large arrow) and procambial cells (white arrow) (X 80, bar: 2 mm). FIG. 10B shows that the cells are packed with lipid bodies (L). Also, the severely desiccated and imbibed somatic embryos exhibited enlarged protein bodies (P) containing dispersed protein deposits after just 2 h imbibation, similar to the zygotic embryos from 65 h imbibed seed (N: nucleus, X 6000, bar: 3 μm). Somatic embryos had a distinct apical meristem, procambium and well developed cotyledons, and were generally larger than zygotic embryos.

In contrast, somatic embryos matured for only 4 weeks without PEG (FIG. 11) or with 7.5% PEG (FIG. 12), contained considerably fewer lipid bodies than observed in 8-week treated somatic embryos (FIG. 9). The level of lipid accumulation was also distinctly lower than in zygotic embryos (c.f. FIG. 7b). Cells of somatic embryos matured for 4 weeks with PEG were more densely cytoplasmic when compared to somatic embryos matured without PEG (for which most cells of the hypocotyl and cotyledons are vacuolate so are not mildly desiccated) which are shown in FIG. 11A (X 135, bar: 0.1 mm).

As shown in FIG. 11B (N: nucleus, X 7500, bar 3 μm), the cytoplasm of cells from somatic embryos matured for 4 weeks with 16 μM but without PEG contain fewer and smaller lipid bodies (L) than in cells from somatic embryos matured for 8 weeks with both ABA and PEG (c.f. FIG. 10B). The cells shown in FIG. 12A (X 130, bar: 0.1 mm) are not vacuolate, but are more densely cytoplasmic and contain more storage reserves (arrows) than cells in embryos matured for the same time in the absence of PEG (c.f. FIG. 11A). The inclusion of PEG during maturation has increased the size and number of lipid bodies (L), starch (S) deposits and mature protein bodies (P) as shown in FIG. 12B (X 6500, bar: 3 μm). However, lipids are not as abundant as in somatic matured for 8 weeks with ABA and PEG as seen in FIG. 9.

Following germination and 4 weeks' growth of zygotic seedlings, most cells had enlarged and undergone vacuolation. As seen in FIG. 13A, vascular traces (large arrow), apical meristems (small arrow) and vacuolate cells were well defined (X 72, bar: 0.2 mm). The electron macrograph shown in FIG. 13B illustrates that lipid bodies were infrequent throughout the seedling and appeared almost empty (arrows) due to utilization of the contents. Protein bodies are absent (N: nucleus, X 6000, bar: 3 μm). This pattern of development also occurred in similarly aged somatic plantlets, regenerated from somatic embryos matured for 8 weeks with 7.5% PEG then further desiccated. However, in some instances plantlets regenerated from the latter treatment had undergone epicotyl (E) elongation and needle development around the apical-meristem by 4 weeks as seen in FIG. 14A (X 54, bar: 0.2 mm). The small arrow indicates the original cotyledon. This degree of development was not observed in the zygotic seedlings of equivalent age. In FIG. 14B, the lipid bodies and protein bodies were not observed. The cells are characterized by many small vacuoles and differentiated chloroplasts (arrows) (N: nucleus, V=vacuole, X 6000, bar: 3 μm).

Discussion

By manipulation of the culture conditions for white spruce somatic embryos it was possible to attain storage lipid levels and fatty acid compositions higher than those observed in zygotic embryos. Such manipulations produced somatic embryos that survived desiccation to low moisture contents then regenerated to plantlets at high frequency. The maturation conditions that resulted in somatic embryos with a fatty acid composition which most closely approximated the mature zygotic embryos were 6–8 weeks with 16–24 μM ABA and 7.5% PEG, followed by further desiccation. These concentrations also led to optimal storage protein deposition in white spruce somatic embryos. The latter 5 study also showed that 5.0–7.5% PEG afforded protection to storage proteins which were otherwise degraded during further desiccation. In addition, this PEG concentration stimulated a doubling of lipid levels and a threefold increase in the maturation frequency of white spruce somatic embryos, and the somatic embryos also possessed lower moisture levels than zygotic embryos from mature dry seed.

Synchronous maturation of the immature white spruce somatic embryos occurred following their transfer from proliferation medium containing 2,4-D acid and BA, to the moisture stressing medium containing PEG and ABA. No maturation occurred in the absence of PEG and ABA. The concentration of ABA and PEG, and maturation period, had an effect on TAG accumulation, whilst fatty acid composition was mostly modified by the latter. More minor modifications to fatty acid composition occurred following further desiccation. TAG levels—as % dry weight—increased from 42% of zygotic levels in the original controls (4 weeks with 0% PEG) to 83% after 8 weeks maturation with 7.5% PEG and 16–24 μM ABA followed by further desiccation, while TAG levels per somatic embryo increased from half that observed in zygotic embryos to almost five times the zygotic levels. This led to somatic embryos with roughly 9 times the level of TAG observed in the controls, and 6 times the fresh weight level recorded by Feirer et al. (1989) for Norway spruce somatic embryos. Vigorous root and shoot elongation was evident in the regenerated somatic plantlets. These results show that although the total amount of TAG for somatic embryos was greater than for zygotic embryos, a lower lipid density resulted from the larger size of the somatic embryos. The increase in dry weight and decrease in moisture content in the presence of PEG as observed in A was, therefore, indicative of increased storage reserves.

The results for lipid accumulation, fatty acid composition, and the TEM and Regeneration studies, together indicate that a 4 week treatment with ABA—as is often used for maturation of conifer somatic embryos, did not allow sufficient time for optimal accumulation of TAG by white spruce somatic embryos, resulting in somatic embryos that were not of comparable maturity to zygotic embryos. A large amount of TAG was synthesized during the $4^{th}$ to $8^{th}$ week of culture. The TEM study provided further evidence for stimulated lipid biosynthesis with 7.5% PEG and extended maturation time, illustrating the well developed structure of the somatic embryos. Storage reserves were previously shown to accumulate initially in the root regions of white spruce somatic embryos, and then subsequently in the later developing shoot meristem and cotyledon regions. The cotyledonary and shoot meristem regions of the somatic embryos appeared after the third week of culture, so additional development of these regions would be necessary before lipid could be deposited.

In order to achieve slow secondary desiccation to low moisture contents somatic embryos were transferred to the 81% r.h. desiccators. The filter-paper supports on which they were transferred were saturated with culture medium, therefore, the moisture stressing environment and initial availability of nutrients appears to have enabled further lipid accumulation, prior to the supply of nutrients drying and the moisture contents of the somatic embryos becoming too low to support metabolism.

A non-plasmolysing moisture stress was influential in preventing precocious germination of white spruce somatic embryos during prolonged maturation and desiccation treatments thereby promoting survival following further desiccation. Optimal TAG accumulated using 7.5% PEG and 16–24 μM ABA. Maturing embryos underwent an increased tendency for precocious germination with increased maturation time leading to poor survival following further desiccation to low moisture content. The increasing tendency for precocious germination suggests a decreased sensitivity to ABA with increased maturation time. Precocious germination was prevented by PEG treatments. In the absence of high moisture stressing treatments, concentrations of up to 60 μM applied throughout the maturation period have been used to inhibit precocious germination during maturation of conifer somatic embryos. However, such concentrations increased the incidence of abnormal somatic embryos.

The plantlet conversion frequencies of 72–81% reported here for somatic embryos matured for 6–8 weeks, may be because they have entered a more desiccation tolerant phase. Desiccation tolerance appears closely related to levels of storage reserves. Thus, treatments that promoted storage reserve accumulation, such as PEG, ABA and increased maturation time, also promoted desiccation tolerance. This is because vacuolate cells containing little reserve material may undergo mechanical disruption and tearing of membranes during severe water loss, while the presence of sufficient reserves limits such changes.

Severely desiccated somatic embryos appear to undergo very rapid imbibition and hence sustain injury, unlike zygotic embryos which are protected within seeds. Protein bodies within the cells of dry seeds swell and take up water during imbibition; thus, as evidenced by protein body ultrastructure, rapidly imbibing somatic embryos by immersing them in liquid medium for just 2 h, was comparable to 65 h of seed imbibition. Therefore, the alternative slower imbibition method used probably reduced injury, so promoted plantlet conversion.

High osmoticum stimulates TAG biosynthesis and influences the quantity and/or composition of the fatty acids; sucrose being the customary osmoticum of choice (e.g. Pence et al. 1981; Janick et al. 1982; Avjioglu and Knox 1989; Dutta and Appelqvist 1989). Fatty acids are formed by converting sucrose into acetyl-Coenzyme A, from which palmitic (16:0) and oleic (18:0) acids are formed and used in the synthesis of unsaturated and longer chain fatty acids (Stymne and Stobart 1987). It has been suggested that sucrose stimulates lipid biosynthesis either by influencing the chemical intermediates of the tricarboxylic acid cycle, or by eliciting osmotic alterations in the cell in response to the low water potential of the culture medium (Pence et al. 1981). The stimulation of lipid biosynthesis in the white spruce somatic embryos using PEG shows that the effect was due to the induced moisture stress and not to a limiting sucrose substrate. Consequently, for maturation of white spruce somatic embryos the optimal osmoticum concentration was higher for PEG than for sucrose. For maturation of white spruce somatic embryos the optimal osmotic potential of the culture medium, which contained 7.5% PEG and 3% sucrose, was −0.7 Mpa.

The oil reserves of seeds are rapidly mobilized back to sucrose following germination to provide energy and carbon skeletons for the post-germinative embryo growth. Lipid reserves are depleted during growth of the white spruce somatic embryos to plantlets in a manner similar to in vitro cultured zygotic seedlings.

REFERENCES

Ammirato, P.V., 1983. Embryogenesis, eds. D. A. Evans, W. R. Sharp, P. V. Ammirato and Y. Yamada, In Handbook of Plant Cell Culture, Vol. 1, pp. 82–123, Macmillan, New York.

Anandarajah, K. and McKersie, B. D., 1990. Enhanced vigor of dry somatic embryos of *Medicago Sativa* L. with increased sucrose. Plant Science 71, 261–266.

Anandarajah, K. and McKersie, B. D., 1990. Manipulating the desiccation tolerance and vigor of dry somatic embryos of *Medicago Sativa* L. with sucrose, heat shock and abscisic acid. Plant Cell Reports 9, 451–455.

Arnold, R. L. B., Fenner, M., Edwards, P. J. (1991) Changes in Germinability, ABA content and ABA embryonic sensitivity in developing seeds of *Sorghum bicolor* (L.) Moench. induced by water stress during grain filling. New Phytol. 118, 339–347.

Attree, S. M., Dunstan, D. I., and Fowke, L. C., 1989. Initiation of embryogenic callus and suspension cultures, and improved embryo regeneration from protoplasts of white spruce (*Picea glauca*). Canadian Journal of Botany 67, 1790–1795.

Attree, S. N., Tautorus, T. E., Dunstan, D. I., Fowke, L. C. (1990) Somatic embryo maturation, germination, and soil establishment of plants of black and white spruce (*Picea mariana* and *Picea glauca*). Can J. Bot. 68, 2583–2589.

Attree, S. N., Fowke, L. C. (1991) Micropropagation through somatic embryogenesis in conifers. In: *Biotechnology in agriculture and forestry, "High-tech and Micropropgaation"*, vol 17, pp. 53–70, Bajaj Y.P.S. ed. Springer-Verlag, Berlin.

Attree, S. M., Dunstan, D. I., Fowke, L. C. (1991 a) White spruce [*Picea glauca* (Moench) Voss] and black spruce [*Picea mariana* (Mill) B.S.P.]. In: Trees III. *Biotechnology in agriculture and forestry*, vol 16, pp. 423–445, Bajaj Y.P.S. ed. Springer-Verlag, Berlin.

Avjioglu, A., Knox, R. B. (1989) Storage lipid accumulation by zygotic and somatic embryos in culture. Ann. Bot. 63, 409–420.

Barratt, D. H. P., Whitford, P. N., Cook, S. K., Butcher, G. and Wang, T. L., 1989, Analysis of seed developments in *Pisum sativam* L. VIII. Does abscisic acid prevent precocious germination and control storage protein synthesis? Journal of Experimental Botany 40, 1990–1014.

Becwar, M. R., Noland, T. L., Wyckoff, J. L. (1989) Maturation germination, and conversion of Norway spruce (*Picea abies* L.) somatic embryos to plants. In Vitro Cell. Devel. Biol. 25, 575–580.

Becwar, H. R., Nagmani, R., Wann, S. R. (1990) Initiation of embryogenic cultures and somatic embryo development in loblolly pine (*Pinus taeda*). Can. J. For. Res. 20, 810–817.

Bewley, J. D., Black, M. (1984) *Seeds: Physiology of development and germination* 367 pp. Plenum press, New York.

Bodsworth, S. and Bewley, J. D., 1981. Osmotic priming of seeds of crop species with polyethylene glycol as a means of enhancing early and synchronous germination at cool temperatures. Can. J. Bot. 59, 672–676.

Brown, C., Brooks, F. J., Pearson, D. and Mathias R. J., 1989. Control of embryogenesis and organogenesis in immature wheat embryo callus using increased medium osmolarity and abscisic acid. J. Plant. Physiol., Vol. 133, pp. 727–733.

Boulay, M. P., Gupta, P. K., Krogstrup, P. and Durzan, D. J., }988. Development of somatic embryos from cell suspension cultures of Norway spruce (*Picea abies* Karst.). Plant Cell Reports 7, 134–137.

Carpita, N., Sabularse, D., Montezinos, D. and Delmer, D., 1979. Determination of the pore size of cell walls of living plant cells. Science 205, 1144–1147.

Ching, T. M. (1963) Fat utilization in germinating Douglas fir seed. Plant Physiol 38, 722–728.

Ching, T. M. (1966) Compositional changes of Douglas fir seed during germination. Plant Physiol. 41, 1313–1319.

Cress, W. A. and Johnson, G. V., 1987. The effect of three osmotic agents on free proline and amino acid pools in *Atriplex canescens* and *Hilaria james* II. Canadian Journal of Botany 65, 799–80.

Dunstan, D. I., Bethune, T. D., Abrams, S. R. (1991) Racemic abscisic acid and abscisyl alcohol promote maturation of white spruce (*Picea glauca*) somatic embryos. Plant Science 76, 219–228.

Dunstan, D. I., Bekkaoui, F., Pilon, M., Fowke, L. C. and Abrams, S. R., 1988. Effects of abscisic acid and analogues on the maturation of white spruce (*Picea glauca*) somatic embryos. Plant Science 58, 77–84.

Dutta, P. C., Appelqvist, L. A. (1989) The effects of different cultural conditions on the accumulation of depot lipids notably petroselinic acid during somatic embryogenesis in *Daucus carota* L. Plant Science 64, 167–177.

Feirer, R. P., Conkey, J. H., S. A. (1989) Triglycerides in embryogenic conifer calli: a comparison with zygotic embryos. Plant Cell Rep. 8, 207–209.

Finkelstein, R. R., Crouch, M. L. (1986) Rapeseed embryo development in culture on high osmoticum is similar to that in seeds. Plant Physiol. 81, 907–912.

Florin, B. and Petiard, v., Canadian Patent Application 2,020,572.

Florin, B., Lecouteux, C. and Petiard, V., Canadian Patent Application 2,013,821.

Fowke, L. C. (1984) Preparation of cultured cells for transmission electron microscopy. In: Cell culture and somatic cell genetics of plants. vol. 1, *Laboratory Procedures and their applications*, pp. 728–737, Vasil, I.K. ed. Academic Press, Inc. Orlando.

Gates, J. C., Greenwood, M. S. (1991), The physical and chemical environment of the developing embryo of *Pinus resinosa*. AM. J. Bot. 78, 1002–1009.

Gómez, J., Sanchez-Martinez, D., Stiefel, V., Rigau, J., Puigdoménech, P. and Pagés, M., 1988. A gene induced by the plant hormone abscisic acid in response to water stress encodes a glycine-rich protein. Nature 334, 262–264.

Gray, D. J., Conger, B. V. and Songstad, D. D., 1987. Desiccated quiescent somatic embryos of orchardgrass for use as synthetic seeds. In Vitro Cellular and Developmental Biology 23, 29–33.

Gray, D. J. and Conger, B. V., PCT Application WO88/03934.

Gray, D. J. and Purohit, A., 1991. Somatic embryogenesis and development of synthetic seed technology. Critical Review in Plant sciences 10(1), 33–61.

Gupta, P. K. and Pullman, G., U.S. Pat. No. 4,957,866.

Gupta, P. K. and Pullman, G., U.S. Pat. No. 5,036,007.

Gupta, P. K. and Pullman, G., U.S. Pat. No. 5,041,382.

Hakman, I., and Fowke, L. C., 1987. Somatic embryogenesis in *Picea glauca* (white spruce) and *Picea mariana* (black spruce). Canadian Journal of Botany 65, 656–659.

Hakman, I., von Arnold, S. (1988) Somatic embryogenesis and plant regeneration from suspension cultures of *Picea glauca* (white spruce). Physiol. Plant. 72, 579–587.

Hakman, I., von Arnold, S. and Eriksson, T., 1985. The development of somatic embryos in tissue cultures initiated from immature embryos of *Picea abies* (Norway spruce). Plant science 38, 53–59.

Hakman, I., Stabel, P., Engstrom, P., Eriksson, T. (1990) Storage protein accumulation during zygotic and somatic embryo development in *Picea abies* (Norway spruce). Physiol. Plant. 80, 441–445.

Hammatt, N. and Davey, M. R., 1987. Somatic embryogenesis and plant regeneration from cultured zygotic embryos of soybean (*Glycine max* L. Merr.). Journal of Plant Physiology 128, 219–226.

Hara, A., Radin, N. S. (1978) Lipid extraction of tissues with a low toxicity solvent. Anal. Biochem. 90, 420–426.

Heyser, J. W. and Nabors, M. W., 1981. Growth, water content, and solute accumulation of two tobacco cell lines cultured on sodium chloride, dextran, and polyethylene glycol. Plant Physiology 68, 1454–1459.

Hohl, M. and Schopfer, P., 1991. Water relations of growing maize coleoptiles. Plant Physiology 95, 716–722.

Janick, J., Wright, D. C., Hasegawa, P. M. (1982) in vitro production of cacao seed lipids. J. Amer. Soc. Hort. Sci. 107, 919–922.

Janick, J. and Kitto, S. L., U.S. Pat. No. 4,615,141.

Joy, R. W., Yeung, E. C., Kong, L., Thorpe, T. (1991) Development of white spruce somatic embryos: 1. Storage product deposition. In vitro Cell. Devel. Biol. 27P, 32–41.

Kartha, K. K., Fowke, L. C., Leung, N. L., Caswell, K. L. and Hakman, I., 1988. Induction of somatic embryos and plantlets from cryopreserved cell cultures of white spruce (*Picea glauca*) J. Plant Physiol. 132, 529–539.

Kermode, A. R. (1990) Regulatory mechanisms involved in the transition from seed development to germination. CRC Crit. Rev. Plant Sci. 9, 155–195.

Kermode, A. R. and Bewley, D. J., 1985. The role of maturation drying in the transition from seed development to germination. Journal of Experimental Botany 36, 1916–1927.

Kermode, A. R. and Bewley, 1989. Developing seeds of *Riccinus communis* L., when detached and maintained in an atmosphere of high relative humidity, switch to a germinative mode without the requirement for complete desiccation. Plant Physiology 90, 702–707.

Kim, Y-H , Janick, J. (1991) Abscisic acid and praline improve desiccation tolerance and increase fatty acid content of celery somatic embryos. Plant Cell Tissue Organ Culture. 24, 83–89.

Kim, Y-H. and Janick, J., 1989. ABA and polyox-encapsulation or high humidity increases survival of desiccated somatic embryos of celery. HortScience 24, 674–676.

Kishor, P.B.K., 1987. Energy and osmotic requirement for high frequency regeneration of rice plants from long-term cultures. Plant Science 48, 189–194.

Kitto, S. L., Pill, W. G. and Molloy, D. M., 1991. Fluid drilling as a delivery system for somatic embryo-derived plantlets of carrot (*Daucus carota* L.). Scientia Horticulturae 47, 209–220.

Konar, R. N. (1958) A quantitative survey of some nitrogenous substances and fats in the developing embryos and gametophytes of *Pinus roxburghii* Sar. Phytomorphology 8, 174–176.

Krizec, D. T. , 1985. Methods of inducing water stress in plants. HortScience 20, 1028–1038.

Krogstrup, P. (1990) Effect of culture densities on cell proliferation and regeneration from embryogenic cell suspensions of *Picea sitchensis*. Plant Science 72, 115–123.

Laine, E., David, A. (1990) Somatic embryogenesis in immature embryos and protoplasts of *Pinus caribaea*. Plant Science 69, 215–224.

Lawlor, D. W., 1979. Absorption of polyethylene glycols in plants and their effects on plant growth. New Phytologist 69, 914–916.

Lawlor, D. W., 1970. Absorption of polyethylene glycols by plants and their effects on plant growth. New Phytol. 69, 501–513.

Leopold, A. C., 1991. Stress responses in Plants: Adaptation and acclimation mechanisms. Pages 37–56, Wiley-Liss, Inc.

Lott. N. A. (1980) Protein Bodies. In: *The biochemistry of plants, a comprehensive treatise*, vol. 1, pp. 589–623, Tolbert N.E. ed. Academic Press, New York.

Mexal, J., Fisher, J. T., Osteryoung, J. and Reid, C. P. P., 1975. Oxygen availability in polyethylene glycol solutions and its implications in plant-water relations. Plant Physiol. 55, 20–24.

Marsolais, A. A., Wilson, D. P. M., Tsujita, M. J. and Senaratna, T., 1991. Somatic embryogenesis and artificial seed production in Zonal (*Pelargonium x hortorum*) and Regal (*Pelargonium X domesticum*) geranium. Can. J. Bot. 69, 1188–1193.

Misra, S., Green, M. J. (1990) Developmental gene expression in conifer embryogenesis and germination. 1. Seed proteins and protein composition of mature embryo and the megagametophyte of white spruce (*Picea glauca* [Moench] Voss.). Plant Science 68, 163–173.

Misra, S., Kermode, A. and Bewley, D. J., 1985. Maturation drying as the 'switch' that terminates seed development and promotes germination. eds. L. van Vloten-Doting, G. S. P. Groot and T. C. Hall, In Molecular form and Function of the Plant Genome, pp. 113–128.

Nato ASI series, Plenum Press, New York, London.

Oertli, J. J., 1985. The response of plant cells to different forms of moisture stress, Journal of Plant Physiology 121, 295–300.

Parrott, W. A., Dryden G., Wogt, S., Hilderbrand, D. F., Collins, G. B. and Williams, E. G., 1988. Optimization of somatic embryogenesis and embryo germination in soybean. In Vitro Cellular and Development Biology 24, 817–820.

Pence, V. C., Hasegawa, P. M., Janick, J. (1981) Sucrose mediated regulation of fatty acid composition in asexual embryos of *Theabroma cacao*. Physiol. Plant. 53, 378–384.

Pomeroy, M. K., Kramer, J. K. D., Hunt, D. J., Keller, W. A. (1991) Fatty acid changes during development of zygotic and microspore derived embryos of *Brassica napus*. Physiol. Plant. 81, 447–454.

Pullman, G. S. and Gupta, P. K., U.S. Pat. No. 5,034,326.

Redenbaugh, K, Viss, P., Slade, D. and Fujii, J. A., 1987. Scale-up: artificial seeds. Plant Tissue and Cell Culture. 473–493.

Redenbaugh, K., Slade, D. and Fujii, J. A., U.S. Pat. No. 4,777,762.

Roberts, D. R., 1991. Abscisic acid and mannitol promote early development maturation and storage protein accumulation in somatic embryos of interior spruce. Physiologia plantarum 83, 247–254.

Roberts, D. R., Lazaroff, N. R. and Webster, F. B., 1991. Interaction between maturation and high relative humidity treatments and their effects on germination of sitka spruce somatic embryos. J. Plant Physiol. 138, 1–6.

Roberts, D R., Flinn, B. S., Webb, D. T., Webster, F. B., Sutton, B. C. S. (1990) Abscisic acid and indole-3-butyric acid regulation of maturation and accumulation of storage proteins in somatic embryos of interior spruce. Physiol. Plant. 78, 355–360.

Roberts, D. R., Sutton, B. C. S. and Flinn, B. S., 1990b. Synchronous and high-frequency germination of interior spruce somatic embryos following partial drying at high relative humidity. Canadian Journal of Botany 68, 1086–1090.

Roberts, D. R., PCT Application CA90/00241.

Saranga, Y. and Janick, J., 1991. Celery somatic embryo production and regeneration: improved protocols. HortScience 26(10), 1335.

Senaratna, T., McKersie, B. D., Bowley, S., Bewley, J. D. and Brown, D., European Patent Application 0 300 730.

Senaratna, T., McKersie, B. D. and Bowley, S. R., 1989. Desiccation tolerance of alfalfa (*Medicago sativa* L.) somatic embryos. Influence of Abscisic acid, stress pretreatments and drying rates. Plant Science 65, 253–259.

Senaratna, T., McKersie B. D. and Bowley, S. R., 1989. Desiccation tolerance of alfalfa (*Medicago sativa* L.) somatic embryos. Influence of abscisic acid, stress pretreatments and drying rates. Plant Science 65, 253 259.

Senaratna, T., Kott, L., Beversdorf, W. D., McKersie, B. D., 1–991. Desiccation of microspore derived embryos of oilseed rape (*Brassica napus* L.). Plant Cell Reports 10, 342–344.

Shimonishi, K., Ishikawa, M., Suzuki, S. and Oosawa, K., 1991. Cryopreservation of melon somatic embryos by desiccation method. Japan. J. Breed. 41, 347–351.

Stymne, S., Stobart, A. K. (1987) Triacylglycerol biosynthesis. In: *The biochemistry of Plants, a comprehensive treatise*, vol. 9, pp. 175–214, Stumpf P.K. ed. Academic Press, New York.

Taylor, D. C., Weber, N., Underhill, E. W., Pomeroy, M. K., Keller, W. A., Scowcroft, W. R., Wilen, R. W., Maloney, M. M., Holbrook, L. A. (1990) Storage protein regulation and lipid accumulation in microspore embryos of *Brassica napus* L. Planta 181, 18–26.

Von Arnold, S., Eriksson, T. (1981) in vitro studies of adventitious shoot formation in *Pinus contorta*. Can. J. Bat. 59, 870–874.

Von Arnold, S. and Hakman, I., 1988. Regulation of somatic embryo development in *Picea abies* by abscisic acid (ABA). Journal of Plant Physiology 132, 164–169.

Webster, F. B., Roberts, D. R., McInnis, S. N., Sutton, B. C. S. (1990) Propagation of interior spruce by somatic embryogenesis. Can. J. Res. 20, 1759–1765.

Woodstock, L. W. and Tao, K. -L. J., 1981. Prevention of imhibitional injury in low vigor soybean embryonic axes by osmotic control of water uptake. Physiol. Plant 51, 133–139.

Xu, N., Bewley, D. J. (1991) Sensitivity to abscisic acid and osmoticum changes during embryogenesis in alfalfa (*Medicago sativa*) J. Exp. Bot. 42, 821–826.

Xu, N., Coulter, K. M. and Bewley, D. J., 1990. Abscisic acid and osmoticum prevent germination of developing alfalfa embryos, but only osmoticum maintains the synthesis of developmental proteins. Planta 182, 382–390.

Zeevaart, J. A. D. and Creelman, R. A., 1988. Metabolism and physiology of abscisic acid. Annual Review of Plant Physiology and Plant Molecular Biology 39, 439–473.

All the above references are herein incorporated by reference.

We claim:

1. A method of producing viable mature desiccation-tolerant gymnosperm somatic embryos, comprising water stressing immature gymnosperm somatic embryos the presence of (i) a metabolisable carbon source suitable for nourishing the mature embryos, and (ii) a growth regulator influencing embryo development; wherein rate of water loss of the embryos, the type and intensity of the water stressing, the length of time during which the water stressing occurs, and the type and concentration the metabolizable carbon source and growth regulator are selected to obtain viable mature desiccation-tolerant gymnosperm embryos tolerant of desiccation to a moisture content of less than about 55%.

2. The method of claim 1, wherein the gymnosperm is a conifer.

3. The method of claim 2, wherein the water stressing is applied to the embryos by an osmotic agent, and simulates non-osmotic water stressing.

4. The method of claim 2, wherein the water stressing is applied by means of a selected suitable environmental effect.

5. The method of claim 2, wherein the water stressing is applied by means of a selected suitable water stressing agent.

6. The method of claim 5, wherein the water stress agent is selected from the group consisting of sucrose, mannitol, polyalkylene glycols, dextrans, celluloses, pectins, galactans, polysucroses, proteins, amino acids, lipoproteins, nucleotides, oligonucleotides, and lipopolysaccharides.

7. The method of claim 6 wherein the polyalkylene glycol is polyethylene glycol.

8. The method of claim 5, wherein the water stressing agent is a selected gel or gelling agent.

9. The method of claim 5, wherein the water stressing agent is agar.

10. The method of claim 5, wherein the water stressing agent is selected from the group comprising gums.

11. The method of claim 5, wherein the water stressing agent is a suitable osmoticum having a molecular size of at least about 30 Angstrom units (Å).

12. The method of claim 5, wherein the water stressing agent is selected from the group comprising non-permeating water stressing agents.

13. The method of claim 2, wherein the water stressing is applied by means of a combination of a selected suitable water stressing agent and a selected suitable environmental effect, and simulates non-osmotic water stressing.

14. The method of claim 3, comprising water stressing the somatic embryos to reach a moisture content of less than about 45%.

15. The method of claim 3, comprising water stressing the somatic embryos to reach a moisture content of less than about 36%.

16. The method of claim 3, further comprising, as a step preceding the water stressing, culturing the immature embryos in a medium containing at least one of:
   (i) auxin, or a functional equivalent thereof, in the amount of 0 $\mu$M to about 9 $\mu$M;
   (ii) cytokinin, or a functional equivalent thereof, in the amount of 0 $\mu$M to about 4.5 $\mu$M.

17. The method of claim 3, wherein the water stressing is substantially non-plasmolysing.

18. The method of claim 3, wherein the embryos are in contact with a culture medium including the metabolisable carbon source and the selected growth regulator and are exposed to atmosphere during at least part of the duration of the water stress.

19. The method of claim 3, wherein the somatic embryos are water stressed in a bioreactor vessel.

20. The method of claim 3, wherein the somatic embryos are water stressed in a continuous-flow, solid-support bioreactor vessel.

21. The method of claim 3, wherein the somatic embryos are water stressed while supported on the surface of a medium in a continuous-flow, solid-support bioreactor vessel comprising a culture chamber having a medium inlet and outlet means for continuous supply of fresh medium in the chamber.

22. The method of claim 3, wherein the somatic embryos are water stressed in a continuous-flow, solid-support bioreactor vessel having means for providing and controlling air flow in the vessel.

23. The method of claim 3, wherein the somatic embryos are water stressed in a controlled gaseous environment.

24. The method of claim 3, wherein the somatic embryos are water stressed in a bioreactor vessel having means for controlling the gaseous environment in the vessel.

25. The method of claim 3, wherein the growth regulator is selected from the group that comprise stress hormones.

26. The method of claim 3, wherein the growth regulator is selected from the group that promote embryonic development.

27. The method of claim 3, wherein the growth regulator is selected from the class comprised of abscisic acid, its precursors, derivatives, and analogs.

28. The method of claim 27, wherein the growth regulator is supplemented with one or more suitable additional growth regulators selected from the group comprising auxin, cytokinin, growth regulators functionally equivalent to auxin, and growth regulators functionally equivalent to cytokinin.

29. The method of claim 27, wherein the application of the growth regulator to the somatic embryos commences when the embryos are in the pre-globular stage.

30. The method of claim 3, wherein the growth regulator is selected from the class comprised of abscisyl alcohol, acetylenic aldehyde, dihydroacetylenic alcohol, phaseic acid (PA), dihydro-phaseic acid (DPA), 6'-hydroxymethyl abscisic acid (HM-ABA), beta-hydroxy abscisic acid, beta-methylglutaryl abscisic acid, beta-hydroxy-beta-methylglutarylhydroxy abscisic acid, 4'-desoxy abscisic acid, abscisic acid, beta-D-glucose ester 2-2(2-p-chlorophenyl-trans-ethyl)cyclopropane carboxylic acid and jasmonic acid and functional derivatives thereof.

31. The method of claim 3, wherein the growth regulator is abscisic acid.

32. The method of claim 3, wherein the growth regulator is maintained at a substantially constant concentration during the greater part of the duration of the water stressing.

33. The method of claim 3, wherein the growth regulator is maintained at a changing concentration during the greater part of the duration of the water stressing.

34. The method of claim 3, wherein the concentration of the growth regulator is slowly increased during the early part of the duration of the water stressing.

35. A method of producing viable mature desiccation-tolerant gymnosperm somatic embryos, comprising water stressing immature gymnosperm somatic embryos in the presence of (i) a metabolisable carbon source suitable for nourishing the immature embryos, (ii) a selected growth regulator influencing embryo development, and (iii) an embryo cell-permeating osmoticum for applying at least a portion of the water stressing; wherein the rate of water loss of the embryos, the type and intensity of the water stressing, the length of time during which the water stressing occurs, and the type and concentration of the osmoticum, metabolizable carbon source and growth regulator are selected to reduce the moisture content of the embryos to a level of less than about 55%.

36. The method of claim 35, wherein the gymnosperm is a conifer.

37. The method of claim 36, wherein the water stressing is substantially non-plasmolysing.

38. The method of claim 36, wherein the water stressing simulates non-osmotic water stressing.

39. The method of claim 36, wherein the water stressing is applied at least in part by a concentration of the metabolisable carbon source in excess of that required to be a limiting substrate for nutrition of the embryo.

40. The method of claim 36, further comprising, as a step preceding the water stressing, a proliferation step comprising culturing the immature embryos in a medium containing an embryo nutrient and optionally:

(i) auxin, or a functional equivalent thereof, in the amount of 0 μM to about 9 μM;

(ii) cytokinin, or a functional equivalent thereof, in the amount of 0 μM to about 4.5 μM.

41. The method of claim 36, comprising water stressing the somatic embryos to reach a moisture content of less than about 45%.

42. The method of claim 36, comprising water stressing the somatic embryos to reach a moisture content of less than about 36%.

43. A method of producing viable mature desiccation-tolerant gymnosperm somatic embryos, comprising water stressing immature gymnosperm somatic embryos in the presence of (i) a metabolisable carbon source suitable for nourishing the immature embryos, (ii) a selected growth regulator influencing embryo development, and (iii) a selected non-permeating osmoticum for applying at least a portion of the water stressing; wherein the rate of water loss of the embryos, the type and intensity of the water stressing, the length of time during which the water stressing occurs, and the type and concentration of the osmoticum, metabolizable carbon source and growth regulator are selected to reduce the moisture content of the embryos to a level of less than about 55%.

44. The method of claim 43, wherein the gymnosperm is a conifer.

45. The method of claim 44, wherein the water stressing simulates non-osmotic water stressing.

46. The method of claim 45, wherein the water stressing is substantially non-plasmolysing.

47. The method of claim 45, wherein the embryos are in contact with a culture medium including the metabolisable carbon source and the selected growth regulator and are exposed to atmosphere during at least part of the duration of the water stress.

48. The method of claim 45, comprising water stressing the somatic embryos to reach a moisture content of less than about 45%.

49. The method of claim 45, comprising water stressing the somatic embryos to reach a moisture content of less than about 36%.

50. The method of claim 45, wherein the growth regulator is selected from the group that promote embryonic development.

51. The method of claim 45, wherein the growth regulator is selected from the group that comprise stress hormones.

52. The method of claim 45, wherein the growth regulator is selected from the class comprised of abscisic acid, its precursors, derivatives, and analogs.

53. The method of claim 52, wherein the growth regulator is applied to the somatic embryos commencing at the pre-globular stage.

54. The method of claim 53, comprising water stressing the somatic embryos to reach a moisture content of less than about 45%.

55. The method of claim 53, comprising water stressing the somatic embryos to reach a moisture content of less than about 36%.

56. The method of claim 45, wherein the growth regulator is selected from the class comprised of abscisyl alcohol, acetylenic aldehyde, dihydroacetylenic alcohol, phaseic acid (PA), dihydro-phaseic acid (DPA), 6'-hydroxymethyl abscisic acid (HM-ABA), beta-hydroxy abscisic acid, beta-methylglutaryl abscisic acid, beta-hydroxy-beta-methylglutarylhydroxy abscisic acid, 4'-desoxy abscisic acid, abscisic acid beta-D-glucose ester 2-2(2-p-chlorophenyl-trans-ethyl)cyclopropane carboxylic acid and jasmonic acid and functional derivatives thereof.

57. The method of claim 45, wherein the growth regulator is abscisic acid.

58. The method of claim 45, wherein the growth regulator is maintained at a substantially constant concentration during the greater part of the duration of the water stressing.

59. The method of claim 45, wherein the growth regulator is maintained at a changing concentration during the greater part of the duration of the water stressing.

60. The method of claim 45, wherein the concentration of the growth regulator is slowly increased during the early part of the duration of the water stressing.

61. The method of claim 45, wherein the non-permeating osmoticum is present in sufficient concentration to create an osmotic potential of between −0.3 and −2.0 Mpa.

62. The method of claim 61, comprising water stressing the somatic embryos to reach a moisture content of less than about 45%.

63. The method of claim 45, wherein the non-permeating osmoticum is present in a concentration up to 30%/wt/vol.

64. The method of claim 45, wherein the non-permeating osmoticum is maintained at a substantially constant concentration during the greater part of the duration of the water stressing.

65. The method of claim 45, wherein the non-permeating osmoticum is maintained at a changing concentration during the greater part of the duration of the water stressing.

66. The method of claim 45, wherein the concentration of the non-permeating osmoticum is slowly increased during at least part of the duration of the water stressing.

67. The method of claim 45, wherein the non-permeating osmoticum has a molecular size of at least about 30 Angstrom units (Å).

68. The method of claim 67, comprising water stressing the somatic embryos to reach a moisture content of less than about 45%.

69. The method of claim 67, comprising water stressing the somatic embryos to reach a moisture content of less than about 36%.

70. The method of claim 45, wherein the non-permeating osmoticum is selected from the group consisting of polyalkylene glycols, dextrans, celluloses, pectins, galactans, polysucroses, oligosac-charides, proteins, lipoproteins, oligonucleotides, and lipopoly-saccharides.

71. The method of claim 45, wherein the non-permeating osmoticum is selected from the group comprising polyalkylene glycols.

72. The method of claim 45, wherein the non-permeating osmoticum is comprised of one or more polyalkylene glycols having a minimum molecular weight of about 1,000.

73. The method of claim 72, comprising water stressing the somatic embryos to reach a moisture content of less than about 45%.

74. The method of claim 72, comprising water stressing the somatic embryos to reach a moisture content of less than about 36%.

75. The method of claim 45, wherein the non-permeating osmoticum is comprised of one or more polyalkylene glycols having a molecular weight ranging between about 1,000 and about 35,000.

76. The method of claim 45, wherein the non-permeating osmoticum is comprised of one or more polyalkylene glycols having a molecular weight ranging between about 1,000 and about 35,000, and wherein the non-permeating osmoticum is present in a concentration ranging between 1 and 30%/wt/vol.

77. The method of claim 76, comprising water stressing the somatic embryos to reach a moisture content of less than about 45%.

78. The method of claim 76, comprising water stressing the somatic embryos to reach a moisture content of less than about 36%.

79. The method of claim 52, wherein the non-permeating osmoticum is selected from the group comprising polyethylene glycols.

80. The method of claim 52, wherein the non-permeating osmoticum is comprised of one or more polyethylene glycols a minimum molecular weight of about 1,000.

81. The method of claim 80, comprising water stressing the somatic embryos to reach a moisture content of less than about 45%.

82. The method of claim 80, comprising water stressing the somatic embryos to reach a moisture content of less than about 36%.

83. The method of claim 52, wherein the non-permeating osmoticum is comprised of one or more polyethylene glycols having a molecular weight ranging between about 1,000 and about 35,000.

84. The method of claim 52, wherein the non-permeating osmoticum is comprised of one or more polyethylene glycols having a molecular weight ranging between about 1,000 and about 35,000, and wherein the non-permeating osmoticum is present in a concentration ranging between 1 and 30%/wt/vol.

85. The method of claim 45, wherein the non-permeating osmoticum is selected from the class of dextrans.

86. The method of claim 45, wherein the non-permeating osmoticum is comprised of one or more dextrans having a minimum molecular weight of about 4000.

87. The method of claim 45, wherein the non-permeating osmoticum is one or more dextrans having a minimum molecular weight of about 4,000 and present in a concentration ranging from 1 to 30%/wt/vol.

88. The method of claim 87, comprising water stressing the somatic embryos to reach a moisture content of less than about 45%.

89. The method of claim 87, comprising water stressing the somatic embryos to reach a moisture content of less than about 36% .

90. The method of claim 45, wherein the water stressing is applied at least in part by a permeating osmoticum.

91. The method of claim 45, wherein the water stressing is applied at least in part by a controlled environment.

92. The method of claim 45, wherein the water stressing is applied at least in part by a concentration of the metabolisable carbon source in excess of that required to be a limiting substrate for nutrition of the embryos.

93. The method of claim 45, wherein the embryos are from the family Pinaceae.

94. The method of claim 45, wherein the embryos are from the family Pinaceae and from the genus Picea.

95. The method of claim 45, wherein the embryos are selected from the group comprising white spruce, black spruce, and Norway spruce.

96. The method of claim 53, wherein the somatic embryos are water stressed to reach a moisture content of less than about 36%, and the non-permeating osmoticum is a selected polyethylene glycol of a molecular size of at least about 30 Angstroms.

97. The method of claim 96, wherein the somatic embryos are frozen following desiccation.

98. The method of claim 96, wherein the somatic embryos are subsequently osmotically primed in the presence of a selected suitable osmoticum.

99. The method of claim 96, wherein the somatic embryos are subsequently osmotically primed and rehydrated in the presence of a selected suitable osmoticum.

100. The method of claim 96, wherein the somatic embryos are subsequently osmotically primed and germinated in the presence of a selected suitable osmoticum.

101. The method of claim 96, wherein the somatic embryos are subsequently osmotically primed and rehydrated and germinated in the presence of a selected suitable osmoticum.

102. The method of claim 96, wherein the somatic embryos are subsequently rehydrated in the presence of a selected suitable osmoticum.

103. The method of claim 96, wherein the somatic embryos are subsequently rehydrated and germinated in the presence of a selected suitable osmoticum.

104. The method of claim 96, wherein the somatic embryos are subsequently germinated in the presence of a selected suitable osmoticum.

105. The method of claim 96, wherein the somatic embryos are subsequently rehydrated in the presence of a selected suitable osmoticum and wherein the concentration of the last-mentioned osmoticum is no more than about 30%.

106. The method of claim 96, wherein the somatic embryos are subsequently germinated in the presence of a selected suitable osmoticum and wherein the concentration of the last-mentioned osmoticum is no more than about 30%.

107. The method of claim 96, wherein the somatic embryos are subsequently rehydrated and germinated in the presence of a selected suitable osmoticum and wherein the concentration of the last-mentioned osmoticum is no more than about 30%.

108. A method of producing viable mature desiccation-tolerant coniferous somatic embryos, comprising applying a substantially non-plasmolysing water stress simulating a non-osmotic water stress to immature coniferous somatic embryos in the presence of (i) a metabolisable carbon source suitable for nourishing the immature embryos;

(ii) a growth regulator influencing embryo development and selected from the class comprised of abscisic acid, its precursors, derivatives, and analogs; and (iii) a suitable non-permeating osmoticum having a molecular size of at least about 30 Angstrom units (Å);

wherein the rate of water loss of the embryos, the intensity of the water stressing, the length of time during which the water stressing occurs, and the concentration of the osmoticum, metabolizable carbon source and growth regulator are selected to reduce the moisture content of the embryos to a level of less than about 55%.

109. The method of claim 108, comprising water stressing the somatic embryos to reach a moisture content of less than about 45%.

110. The method of claim 108, comprising water stressing the somatic embryos to reach a moisture content of less than about 36%.

111. The method of claim 108, wherein the non-permeating osmoticum is selected from the group comprising polyalkylene glycols, dextrans, celluloses, pectins, galactans, polysucroses, oligosaccharides, proteins, lipoproteins, oligonucleotides, and lipopolysaccharides.

112. The method of claim 108, wherein the non-permeating osmoticum is selected from the group comprising polyethylene glycols.

113. The method of claim 112, comprising water stressing the somatic embryos to reach a moisture content of less than about 45%.

114. The method of claim 112, comprising water stressing the somatic embryos to reach a moisture content of less than about 36%.

115. The method of claim 108, further comprising, as a step preceding the water stressing, a proliferation step comprising culturing the immature embryos in a medium containing an embryo nutrient and optionally:
  (i) auxin, or a functional equivalent thereof, in the amount of 0 $\mu$M to about 9 $\mu$M;
  (ii) cytokinin, or a functional equivalent thereof, in the amount of 0 $\mu$M to about 4.5 $\mu$M.

116. The method of claim 115, wherein the growth regulator is applied to the somatic embryos commencing at the pre-globular stage.

117. The method of claim 116, comprising water stressing the somatic embryos to reach a moisture content of less than about 45%.

118. The method of claim 116, comprising water stressing the somatic embryos to reach a moisture content of less than about 36%.

119. The method of claim 108, wherein the embryos are in contact with a culture medium including the metabolisable carbon source and the selected growth regulator and are exposed to atmosphere during at least part of the duration of the water stress.

120. The method of claim 108, wherein the somatic embryos are water stressed in a bioreactor vessel.

121. The method of claim 108, wherein the somatic embryos are water stressed in a continuous-flow, solid-support bioreactor vessel.

122. The method of claim 108, wherein the somatic embryos are water stressed while supported on the surface of a medium in a continuous-flow, solid-support bioreactor vessel comprising a culture chamber having a medium inlet and outlet means for continuous supply of fresh medium in the chamber.

123. The method of claim 108, wherein the somatic embryos are water stressed in a continuous-flow, solid-support bioreactor vessel having means for providing and controlling air flow in the vessel.

124. The method of claim 108, wherein the somatic embryos are water stressed in a controlled gaseous environment.

125. The method of claim 108, wherein the somatic embryos are water stressed in a bioreactor vessel having means for controlling the gaseous environment in the vessel.

126. The method of claim 108, wherein the growth regulator is selected from the class comprised of abscisyl alcohol, acetylenic aldehyde, dihydroacetylenic alcohol, phaseic acid (PA), dihydrophaseic acid (DPA), 6'-hydroxymethyl abscisic acid (HM-ABA), beta-hydroxy abscisic acid, beta-methylglutaryl abscisic acid, beta-hydroxy-beta-methylglutarylhydroxy abscisic acid, and 4'-desoxy abscisic acid.

127. The method of claim 108, wherein the non-permeating osmoticum is comprised of one or more polyethylene glycols having a minimum molecular weight of about 1,000.

128. The method of claim 127, comprising water stressing the somatic embryos to reach a moisture content of less than about 45%.

129. The method of claim 127, comprising water stressing the somatic embryos to reach a moisture content of less than about 36%.

130. The method of claim 127, further comprising, as a step preceding the water stressing, a proliferation step comprising culturing the immature embryos in a medium containing an embryo nutrient and optionally:
  (i) auxin, or a functional equivalent thereof, in the amount of 0 $\mu$M to about 9 $\mu$M;
  (ii) cytokinin, or a functional equivalent thereof, in the amount of 0 $\mu$M to about 4.5 $\mu$M.

131. The method of claim 130, wherein the growth regulator is applied to the somatic embryos commencing at the pre-globular stage.

132. The method of claim 108, wherein the non-permeating osmoticum is comprised of one or more polyethylene glycols having a molecular weight ranging between about 1,000 and about 35,000.

133. The method of claim 108, wherein the non-permeating osmoticum is comprised of one or more polyethylene glycols having a molecular weight ranging between about 1,000 and about 35,000, and wherein the non-permeating osmoticum is present in a concentration ranging between 1 and 30%/wt/vol.

134. The method of claim 108, wherein the non-permeating osmoticum is present in sufficient concentration to create an osmotic potential of between −0.3 and −2.0 Mpa.

135. The method of claim 133, further comprising, as a step preceding the water stressing, a proliferation step comprising culturing the immature embryos in a medium containing an embryo nutrient and optionally:
  (i) auxin, or a functional equivalent thereof, in the amount of 0 $\mu$M to about 9 $\mu$M;
  (ii) cytokinin, or a functional equivalent thereof, in the amount of 0 $\mu$M to about 4.5 $\mu$M.

136. The method of claim 135, wherein the embryos are in contact with a culture medium including the metabolisable carbon source and the selected growth regulator and are exposed to atmosphere during at least part of the duration of the water stress.

137. The method of claim 108, wherein the non-permeating osmoticum is comprised of one or more polyethylene glycols each having a molecular weight of at least about 1,000, wherein the non-permeating osmoticum is present in a concentration ranging between 1 and 30%/wt/vol., and wherein the growth regulator is applied to the somatic embryos commencing at the pre-globular stage.

138. The method of claim 137, wherein the somatic embryos are water stressed while supported on the surface of the medium in a continuous-flow, solid-support bioreactor vessel comprising a culture chamber having a medium inlet and outlet means for continuous supply of fresh medium in the chamber, and means for providing and controlling air flow in the vessel.

139. The method of claim 138, wherein the growth regulator is selected from the class comprised of abscisyl alcohol, acetylenic aldehyde, dihydroacetylenic alcohol, phaseic acid (PA), dihydrophaseic acid (DPA), 6'-hydroxymethyl abscisic acid (HM-ABA), beta-hydroxy abscisic acid, beta-methylglutaryl abscisic acid, beta-hydroxy-beta-methylglutarylhydroxy abscisic acid, and 4'-desoxy abscisic acid.

140. The method of claim 139, wherein the non-permeating osmoticum is present in sufficient concentration to create an osmotic potential of between −0.3 and −2.0 Mpa.

141. The method of claim 136, wherein the growth regulator is selected from the class comprised of abscisyl alcohol, acetylenic aldehyde, dihydroacetylenic alcohol, phaseic acid (PA), dihydrophaseic acid (DPA), 6'-hydroxymethyl abscisic acid (HM-ABA), beta-hydroxy abscisic acid, beta-methylglutaryl abscisic acid, beta-hydroxy-beta-methylglutarylhydroxy abscisic acid, and 4'-desoxy abscisic acid.

142. A method of producing viable mature desiccation-tolerant coniferous somatic embryos, comprising applying a substantially non-plasmolysing water stress to immature coniferous somatic embryos in the presence of
(i) a metabolisable carbon source suitable for nourishing the immature embryos; and
(ii) a growth regulator influencing embryo development selected from the class comprised of abscisic acid, its precursors, derivatives, and analogs;
wherein the rate of water loss of the embryos, the type and intensity of the water stressing, the length of time during which the water stressing occurs, and the type and concentration of the metabolizable carbon source and growth regulator are selected to reduce the moisture content of the embryos to a level of less than about 55%.

143. The method of claim 142, further comprising, as a step preceding the water stressing, a proliferation step comprising culturing the immature embryos in a medium containing an embryo nutrient and optionally:
(i) auxin, or a functional equivalent thereof, in the amount of 0 $\mu$M to about 9 $\mu$M;
(ii) cytokinin, or a functional equivalent thereof, in the amount of 0 $\mu$M to about 4.5 $\mu$M.

144. The method of claim 142, wherein the water stressing is applied by means of a selected non-osmotic agent.

145. The method of claim 144, wherein the non-osmotic agent is a selected gel or gelling agent.

146. The method of claim 144, wherein the non-osmotic agent is agar.

147. The method of claim 144, wherein the non-osmotic agent is a substance whose molecules have a molecular size of at least about 30 Angstrom units (Å).

148. The method of claim 142, wherein the embryos are in contact with a culture medium including the metabolisable carbon source and the selected growth regulator and are exposed to atmosphere during at least part of the duration of the water stress.

149. The method of claim 142, comprising water stressing the somatic embryos to reach a moisture content of less than about 45%.

150. The method of claim 142, comprising water stressing the somatic embryos to reach a moisture content of less than about 36%.

151. The method of claim 147, comprising water stressing the somatic embryos to reach a moisture content of less than about 45%.

152. The method of claim 147, comprising water stressing the somatic embryos to reach a moisture content of less than about 36%.

153. The method of claim 142, wherein the water stress is applied at least in part by a controlled environment.

154. The method of claim 153, wherein the water stress constitutes or simulates a non-osmotic water stress.

155. The method of claim 153, wherein the water stressing is applied at least in part by a controlled decrease in relative humidity.

156. The method of claim 155, comprising water stressing the somatic embryos to reach a moisture content of less than about 45%.

157. The method of claim 155, comprising water stressing the somatic embryos to reach a moisture content of less than about 36%.

158. The method of claim 153, wherein the environmental water stressing is applied at least in part by a controlled decrease in relative humidity in the range 5%–100%.

159. The method of claim 153, wherein the environmental water stressing is applied at least in part by rapid drying of the embryos.

160. The method of claim 153, wherein the environmental water stressing is applied at least in part by slow drying of the embryos.

161. The method of claim 142, wherein the growth regulator is applied to the somatic embryos from the pre-globular stage thereof.

162. The method of claim 2, comprising water stressing the somatic embryos to reach a moisture content of less than about 45%.

163. The method of claim 2, comprising water stressing the somatic embryos to reach a moisture content of less than about 36%.

164. The method of claim 2, further comprising, as a step preceding the water stressing, a proliferation step comprising culturing the immature embryos in a medium containing an embryo nutrient and optionally:
(i) auxin, or a functional equivalent thereof, in the amount of 0 $\mu$M to about 9 $\mu$M;
(ii) cytokinin, or a functional equivalent thereof, in the amount of 0 $\mu$M to about 4.5 $\mu$M.

165. The method of claim 2, wherein the water stressing is substantially non-plasmolysing.

166. The method of claim 2, wherein the embryos are in contact with a culture medium including the metabolisable carbon source and the selected growth regulator and are exposed to atmosphere during at least part of the duration of the water stress.

167. The method of claim 2, wherein the somatic embryos are water stressed while supported on the surface of a medium in a continuous-flow, solid-support bioreactor vessel comprising a culture chamber having a medium inlet and outlet means for continuous supply of fresh medium in the chamber.

168. The method of claim 167, wherein the bioreactor vessel has means for providing and controlling air flow in the vessel.

169. The method of claim 2, wherein the somatic embryos are water stressed in a controlled gaseous environment.

170. The method of claim 2, wherein the growth regulator is selected from the group that comprise stress hormones.

171. The method of claim 2, wherein the growth regulator is selected from the group that promote embryonic development.

172. The method of claim 2, wherein the growth regulator is selected from the class comprised of abscisic acid, its precursors, derivatives, and analogs.

173. The method of claim 172, wherein the growth regulator is supplemented with one or more suitable additional growth regulators selected from the group comprising auxin, cytokinin, growth regulators functionally equivalent to auxin, and growth regulators functionally equivalent to cytokinin.

174. The method of claim 2, wherein the growth regulator is selected from the class comprised of abscisyl alcohol, acetylenic aldehyde, dihydroacetylenic alcohol, phaseic acid (PA), dihydrophaseic acid (DPA), 6'-hydroxymethyl abscisic acid (HM-ABA), beta-hydroxy abscisic acid, beta-methylglutaryl abscisic acid, beta-hydroxy-betamethylglutarylhydroxy abscisic acid, 4'-desoxy abscisic acid, abscisic acid, beta-D-glucose ester 2-2(2-p-chlorophenyl-trans-ethyl)cyclopropane carboxylic acid and jasmonic acid and functional derivatives thereof.

175. The method of claim 172, wherein the application of the growth regulator to the somatic embryos commences when the embryos are in the pre-globular stage.

176. The method of claim 3, wherein the water stressing agent is a suitable osmoticum having a molecular size of at least about 30 Angstrom units (Å).

177. The method of claim 15, wherein the viable mature desiccation-tolerant somatic embryos are encapsulated.

178. The method of claim 15, further comprising coating the viable mature desiccation-tolerant somatic embryos with a suitable liquid non-hydrated substance having a melting point ranging between about 20 and 70° C.

179. The method of claim 3, wherein the growth regulator is initially present in sufficient concentration to achieve a final concentration of at least about 10 $\mu$M at the end of the development of the somatic embryos.

180. The method of claim 31 wherein the concentration of abscisic acid ranges from 0.1 $\mu$M to 100 $\mu$M.

181. The method of claim 31, wherein the concentration of abscisic acid ranges from 12 $\mu$M to 60 $\mu$M.

182. The method of claim 31, wherein the concentration of abscisic acid is at least about 16 $\mu$M.

183. The method of claim 45, wherein the concentration of abscisic acid is at least about 16 $\mu$M.

184. The method of claim 108, wherein the concentration of abscisic acid is at least about 16 $\mu$M.

185. The method of claim 31, wherein abscisic acid is present at a concentration of at least about 10 $\mu$M at the end of the development of the somatic embryos.

186. The method of claim 46, wherein the growth regulator is initially present in sufficient concentration to achieve a final concentration of at least about 10 $\mu$M at the end of the development of the somatic embryos.

187. The method of claim 108, wherein said non-plasmolysing water stress in the presence of a suitable non-permeating osmoticum is followed by an environmental water stress once the embryos are mature.

188. The method of claim 57, wherein abscisic acid is present at a concentration of at least about 10 $\mu$M at the end of the development of the somatic embryos.

189. The method of claim 43, wherein the growth regulator is selected from the class comprised of abscisic acid, its precursors, derivatives, and analogs, and wherein at the completion of the said water stress, the growth regulator is present in a concentration of at least about 10 $\mu$M.

190. The method of claim 189, additionally comprising further water stressing the embryos to reduce their moisture content below about 36%.

191. The method of claim 190, wherein the further water stressing is predominantly a drought stress.

192. The method of claim 3, wherein the growth regulator is initially present in sufficient concentration to achieve a final concentration of at least 0.1 $\mu$M at the end of the development of the somatic embryos.

193. The method of claim 31, wherein abscisic acid is present at a concentration of at least 0.1 $\mu$M at the end of the development of the somatic embryos.

194. The method of claim 31, wherein abscisic acid is present at a concentration of at least 16 $\mu$M at the end of the development of the somatic embryos.

195. The method of claim 46, wherein the growth regulator is initially present in sufficient concentration to achieve a final concentration of at least 0.1 $\mu$M at the end of the development of the somatic embryos.

196. The method of claim 57, wherein abscisic acid is present at a concentration of at least 0.1 $\mu$M at the end of the development of the somatic embryos.

197. The method of claim 57, wherein abscisic acid is present at a concentration of at least 16 $\mu$M at the end of the development of the somatic embryos.

198. The method of claim 43, followed by an environmental water stress to reduce the moisture content of the embryos below 45%.

199. The method of claim 43, wherein at the completion of the said water stress, the growth regulator is present in a concentration of at least about 0.1 $\mu$M, and additionally comprising further water stressing the embryos to reduce their moisture content below 45%.

200. The method of claim 198, wherein the further water stressing is predominantly a drought stress.

201. The method of claim 199, wherein the further water stressing reduces the moisture content of the embryos to 36% or less.

202. The method of claim 200, wherein the growth regulator is selected from the class comprised of abscisic acid, its precursors, derivatives, and analogs.

203. The method of claim 43, wherein at the completion of the said water stress, the growth regulator is present in a concentration of at least about 16 $\mu$M, and additionally comprising further water stressing the embryos to reduce their moisture content below 45%.

204. The method of claim 202, wherein the further water stressing is predominantly a drought stress.

205. The method of claim 203, wherein the further water stressing reduces the moisture content of the embryos to 36% or less.

206. The method claim of 204, wherein the growth regulator is selected from the class comprised of abscisic acid, its precursors, derivatives, and analogs.

207. The method of claim 43, wherein the said water stress is followed by an environmental water stress once the embryos are mature.

208. The method of claim 46, wherein the water stress occurs in two stages, viz a first stage in which the water stress is applied to the embryos primarily by a non-permeating osmoticum, and a second stage in which the water stress is applied to the embryos primarily by a reduction in ambient relative humidity.

209. The method of claim 207, wherein the embryos are supported by medium-permeable support means in contact with a growth/maturation medium during the first stage, and following maturation, the medium is removed.

210. The method of claim 207, wherein the first stage reduces the moisture content of the embryos below about 55%, and the second stage reduces the moisture content of the embryos below about 45%.

211. The method of claim 207, wherein the first stage reduces the moisture content of the embryos below about 55%, and the second stage reduces the moisture content of the embryos below about 36%.

212. The method of claim 207, wherein the first stage reduces the moisture content of the embryos below about 45%, and the second stage reduces the moisture content of the embryos below about 36%.

213. The method of claim 209, wherein at the end of the first stage, the growth regulator is present in a concentration of at least about 0.1 $\mu$M.

214. The method of claim 209, wherein at the end of the first stage, the growth regulator is present in a concentration of at least about 16 $\mu$M.

215. The method of claim 212, wherein the growth regulator is selected from the class comprised of abscisic acid, its precursors, derivatives, and analogs.

216. The method of claim 213, wherein the growth regulator is selected from the class comprised of abscisic acid, its precursors, derivatives, and analogs.

217. The method of claim 210, wherein at the end of the first stage, the growth regulator is present in a concentration of at least about 0.1 μM.

218. The method of claim 216, wherein at the end of the first stage, the growth regulator is present in a concentration of at least about 16 μM.

219. The method of claim 216, wherein the growth regulator is selected from the class comprised of abscisic acid, its precursors, derivatives, and analogs.

220. The method of claim 217, wherein the growth regulator is selected from the class comprised of abscisic acid, its precursors, derivatives, and analogs.

221. The method of claim 211, wherein at the end of the first stage, the growth regulator is present in a concentration of at least about 0.1 μM.

222. The method of claim 220, wherein at the end of the first stage, the growth regulator is present in a concentration of at least about 16 μM.

223. The method of claim 220, wherein the growth regulator is selected from the class comprised of abscisic acid, its precursors, derivatives, and analogs.

224. The method of claim 221, wherein the growth regulator is selected from the class comprised of abscisic acid, its precursors, derivatives, and analogs.

225. The method of claim 186, wherein at the completion of the said non-plasmolysing water stress, the growth regulator is present in a concentration of at least about 0.1 μM.

226. The method of claim 186, wherein the completion of the said non-plasmolysing water stress, the growth regulator is present in a concentration of at least about 16 μM.

227. The method of claim 52, wherein the concentration of abscisic acid ranges from 0.1 μM to 100 μM.

228. The method of claim 52, wherein the concentration of abscisic acid ranges from 12 μM to 60 μM.

229. The method of claim 108, wherein the concentration of abscisic acid ranges from 0.1 μM to 100 μM.

230. The method of claim 108, wherein the concentration of abscisic acid ranges from 12 μM to 60 μM.

231. A method of producing viable mature desiccated conifer somatic embryos, comprising
   a) water stressing immature conifer somatic embryos in the presence of (i) a metabolisable carbon source suitable for nourishing the immature embryos, (ii) a selected growth regulator influencing embryo development, and (iii) a selected non-permeating osmoticum for applying at least a portion of the water stressing; wherein the rate of water loss of the embryos, the type and intensity of the water stressing, the length of time during which the water stressing occurs, and the type and concentration of the osmoticum, metabolizable carbon source and growth regulator are selected to reduce the moisture content of the embryos to a level of less than about 55% wherein the water stressing is substantially non-plasmo-lysing and simulates non-osmotic water stressing; and
   b) further desiccating the embryo s following the water stressing step (a).

232. The method of claim 231, wherein the osmoticum is polyethylene glycol of molecular weight at least about 1000, and the growth regulator is selected from the group comprising abscisic acid, its precursors, derivatives, and analogs.

233. A method of producing viable mature desiccated conifer somatic embryos, comprising
   a) water stressing immature conifer somatic embryos in a medium containing (i) a metabolisable carbon source suitable for nourishing the immature embryos, (ii) a selected growth regulator influencing embryo development, and (iii) a selected non-permeating osmoticum for applying at least a portion of the water stressing; wherein the rate of water loss of the embryos, the type an d intensity of the water stressing, the length of time during which the water stressing occurs, and the type and concentration of the osmoticum, metabolizable carbon source and growth regulator are selected to reduce the moisture content of the embryos to a level of less than about 55%; wherein the water stressing is substantially non-plasmo-lysing and simulates non-osmotic water stressing; and
   b) removing the medium and further desiccating the embryos following the water stressing step (a).

234. The method of claim 233, wherein the osmoticum is polyethylene glycol of molecular weight at least about 1000, and the growth regulator is selected from the group comprising abscisic acid, its precursors, derivatives, and analogs.

235. A method of producing viable mature desiccated conifer somatic embryos, comprising
   a) water stressing immature conifer somatic embryos in the presence of (i) a metabolisable carbon source suitable for nourishing the immature embryos, (ii) a selected growth regulator influencing embryo development, and (iii) a selected non-permeating osmoticum for applying at least a portion of the water stressing; wherein the rate of water loss of the embryos, the type and intensity of the water stressing, the length of time during which the water stressing occurs, and the type and concentration of the osmoticum, metabolizable carbon source and growth regulator are selected to reduce the moisture content of the embryos to a level of less than about 55%; wherein the water stressing is substantially non-plasmo-lysing and simulates non-osmotic water stressing; and
   b) following the water stressing step (a), further desiccating the embryos to a moisture level of less than about 36%, thereby to produce said viable mature desiccated conifer somatic embryos.

236. The method of claim 235, wherein the osmoticum is polyethylene glycol of molecular weight at least about 1000, and the growth regulator is selected from the group comprising abscisic acid, its precursors, derivatives, and analogs.

237. A method of producing viable mature desiccation-tolerant conifer somatic embryos, comprising applying to immature conifer somatic embryos a substantially non-plasmolysing water stressing and growth regulating treatment in the presence of (i) a metabolisable carbon source suitable for nourishing the immature embryos, and (ii) a selected growth regulator influencing embryo development, selected from the group comprising abscisic acid, its precursors, derivatives, and analogs; wherein the rate of water loss of the embryos, the type and intensity of the water stressing, the length of time during which the water stressing occurs, and the type and concentration of the metabolizable carbon source and concentration of the growth regulator are selected to reduce the moisture content of the embryos to a level of less than about 55%; and wherein the concentration of growth regulator present at the completion of the water stressing and growth regulating treatment of the embryos is at least about 10 μM.

238. The method of claim 237, wherein the water stressing occurs in the presence of a selected non-permeating osmoticum of molecular size at least about 30 Angstrom units (Å) for applying at least a portion of the water stressing.

239. The method of claim 238, wherein the concentration of growth regulator present at the completion of the water stressing and growth regulating treatment of the embryos is in the range about 12 μM to about 100 μM.

240. The method of claim 238, wherein the osmoticum is polyethylene glycol of molecular weight at least about 1000.

241. A method of producing viable mature desiccated conifer somatic embryos, comprising a) applying to immature conifer somatic embryos a substantially non-plasmolysing water stressing and growth regulating treatment in the presence of (i) a metabolisable carbon source suitable for nourishing the immature embryos, and (ii) a selected growth regulator influencing embryo development, selected from the group comprising abscisic acid, its precursors, derivatives, and analogs; wherein the rate of water loss of the embryos, the type and intensity of the water stressing, the length of time during which the water stressing occurs, and the type and concentration of the metabolizable carbon source and concentration of the growth regulator are selected to reduce the moisture content of the embryos to a level of less than about 55%; and wherein the concentration of growth regulator present at the completion of the water stressing and growth regulating treatment of the embryos is at least about 10 μM;

b) following the water stressing and growth regulating step (a), further desiccating the embryos to a moisture level of less than about 36%, thereby to produce said viable mature desiccated conifer somatic embryos.

242. The method of claim 241, wherein the water stressing occurs in the presence of a selected non-permeating osmoticum of molecular size at least about 30 Angstrom units (Å) for applying at least a portion of the water stressing.

243. The method of claim 242, wherein the osmoticum is polyethylene glycol of molecular weight at least about 1000.

244. The method of claim 242, wherein the concentration of growth regulator present at the completion of the water stressing and growth regulating treatment of the embryos is in the range about 12 μM to about 100 μM.

245. The method of claim 244, wherein the osmoticum is polyethylene glycol of molecular weight at least about 1000.

246. The method of claim 241, wherein step (b) comprises further osmotic water stressing the embryos.

247. The method of claim 241, wherein step (b) comprises drying the embryos in a decreasing relative humidity environment.

248. The method of claim 241, wherein step (b) comprises drying the embryos on supports impregnated with medium at the completion of step (a) in a decreasing relative humidity environment that dries the embryos, the supports and the medium impregnated therein.

249. A method of producing viable mature desiccated conifer somatic embryos, comprising a) water stressing immature conifer somatic embryos on suitable supporting substrate material in contact with a medium containing (i) a metabolisable carbon source suitable for nourishing the immature embryos, (ii) a selected growth regulator influencing embryo development, and (iii) a selected non-permeating osmoticum for applying at least a portion of the water stressing; wherein the rate of water loss of the embryos, the type and intensity of the water stressing, the length of time during which the water stressing occurs, and the type and concentration of the osmoticum, metabolizable carbon source and growth regulator are selected to reduce the moisture content of the embryos to a level of less than about 55%; wherein the water stressing is substantially non-plasmo-lysing and simulates non-osmotic water stressing; and b) following the water stressing step (a), removing the substrate material from the medium and further desiccating the embryos to a moisture content of less than about 36%.

\* \* \* \* \*

UNITED STATES PATENT AND TRADEMARK OFFICE
CERTIFICATE OF CORRECTION

PATENT NO. : 6,340,594 B1
DATED : January 22, 2002
INVENTOR(S) : Stephen M. Attree and Lawrence C. Fowke It is certified that error appears in the above-identified patent and that said Letters Patent is hereby corrected as shown below:

Column 59,
Line 27, delete "claim 45" and insert -- claim 52 --

Column 62,
Line 6, delete "an d" and insert -- and --

Signed and Sealed this

Third Day of September, 2002

*Attest:*

JAMES E. ROGAN
*Attesting Officer*  *Director of the United States Patent and Trademark Office*